(12) United States Patent
Wooley et al.

(10) Patent No.: US 6,383,500 B1
(45) Date of Patent: *May 7, 2002

(54) PARTICLES COMPRISING AMPHIPHILIC COPOLYMERS, HAVING A CROSSLINKED SHELL DOMAIN AND AN INTERIOR CORE DOMAIN, USEFUL FOR PHARMACEUTICAL AND OTHER APPLICATIONS

(75) Inventors: Karen L. Wooley; K. Bruce Thurmond, II; Haiyong Huang, all of St. Louis, MO (US)

(73) Assignee: Washington University, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/902,614

(22) Filed: Jun. 27, 1997

Related U.S. Application Data

(60) Provisional application No. 60/020,693, filed on Jun. 27, 1996.

(51) Int. Cl.[7] .............................. A61K 7/00; A61K 9/50; A61K 47/00; A01N 25/34

(52) U.S. Cl. ...................... 424/401; 424/497; 424/408; 424/439; 424/78.13; 428/407

(58) Field of Search ................................ 424/781, 489, 424/401, 497, 490, 439, 408, 78.18; 428/407

(56) References Cited

U.S. PATENT DOCUMENTS

| | | |
|---|---|---|
| 3,489,699 A | 1/1970 | Battaerd et al. |
| 3,565,833 A | 2/1971 | Battaerd |

(List continued on next page.)

FOREIGN PATENT DOCUMENTS

| | | |
|---|---|---|
| CA | 1111453 | 10/1981 |
| CH | 594 444 | 1/1978 |
| EP | 0007895 A1 | 2/1980 |
| EP | 0 320 930 | 6/1989 |
| EP | 0 552 802 | 7/1993 |
| EP | 0577215 A1 | 1/1994 |
| JP | 60195455 * | 3/1984 |
| JP | 22077266 | 1/1990 |
| JP | 0 5178916 | 7/1993 |
| WO | 9322427 | 11/1993 |
| WO | WO 94/1590 | 7/1994 |
| WO | WO 94/17789 | 8/1994 |
| WO | 9421308 | 9/1994 |
| WO | 9620696 | 7/1996 |

OTHER PUBLICATIONS

Photochemical Crosslinking and Isolation of Block Copolymers in Selective Solvent; Ahmed, et al; J. Surf. Sci. Tech., vol. 3(2), 85–89, 1987.

Styrene–terminated poly(vinyl alcohol) macromonomers: 2. Free–radical (co)polymerization studies and application to the functionalization of latex particles; Charleux, et al.; Polymer, 1993, 34(20), pp. 4352–4359.

(List continued on next page.)

*Primary Examiner*—Thurman K. Page
*Assistant Examiner*—Blessing Fubara
(74) *Attorney, Agent, or Firm*—Senniger, Powers, Leavitt & Roedel

(57) ABSTRACT

Provided are particles comprising amphiphilic copolymers, having a crosslinked shell domain and an interior core domain. Also provided are compositions comprising such particles, including pharmaceutical compositions, methods of making the present particles, and methods of using such particles, for example for delivery of pharmaceutically active agents.

98 Claims, 1 Drawing Sheet

U.S. PATENT DOCUMENTS

| | | | |
|---|---|---|---|
| 4,252,793 A | 2/1981 | Altman | 424/199 |
| 4,330,677 A | 5/1982 | Linke et al. | 562/583 |
| 4,359,478 A | 11/1982 | Schmolka | 424/308 |
| 4,593,073 A | 6/1986 | St. Pierre et al. | 525/328.4 |
| 4,600,578 A | 7/1986 | Pircio et al. | 424/78 |
| 4,604,430 A | 8/1986 | Johnson | 525/326.7 |
| 4,649,048 A | 3/1987 | Johnson | 424/81 |
| 4,681,915 A | 7/1987 | Bates et al. | 525/148 |
| 4,769,388 A | 9/1988 | Ferruti et al. | 514/547 |
| 4,844,900 A | 7/1989 | Albornoz et al. | 424/81 |
| 4,851,318 A * | 7/1989 | Hsieh et al. | 430/137 |
| 5,114,709 A | 5/1992 | St. Pierre et al. | 424/78.12 |
| 5,250,294 A | 10/1993 | Hunter et al. | 424/78.31 |
| 5,260,272 A | 11/1993 | Donachy et al. | 524/12 |
| 5,384,333 A | 1/1995 | Davis et al. | 514/772.3 |
| 5,428,112 A | 6/1995 | Ahlers et al. | 525/326.7 |
| 5,429,826 A | 7/1995 | Nair et al. | 424/501 |
| 5,430,110 A | 7/1995 | Ahlers et al. | 525/328.2 |
| 5,453,429 A * | 9/1995 | Bliem et al. | 424/78.12 |
| 5,498,421 A * | 3/1996 | Grinstaff et al. | 424/450 |
| 5,597,810 A | 1/1997 | Hoffman et al. | 514/54 |
| 5,712,346 A | 1/1998 | Lee | |

OTHER PUBLICATIONS

Photopolymerization of Micelle–Forming Monomers. 1. Characterization of the Systems before and after Polymerization; Cochin, et al; Macromolecules 1993, 26, 5755–5764.

Stereocomplex Formation in Blends of Block Copolymers of Syndiotactic Poly(methyl methacrylate) (PMMA)–Poly-(dimethylsiloxane)(PDMS) and Isotactic PMMA. Differential Scanning Calorimetry (DSC) and Dynamic Mechanical Thermal Analysis (DMTA); Deuring, et al; Macromolecules 1995, 28. 1952–1958.

Polyisoprene–block–poly(2–cinnamoylethyl methacrylate) Vesicles and Their Aggregates; Ding, et al; Macromolecules 1997, 30, 655–657.

Polymerized Surfactant Aggregates: Characterization and Utilization; Fendler, et al; Acc. Chem. Res. 1984, 17, 3–8.

Chemical Fixation of Micro Heterogeneous Domains Composed of sequential Copolymers by Crosslinking Reactions; Fukutomi, et al; Polym.–Plast. Technol. Eng., 27(2), 201–236 (1988).

Star Polymers and Nanospheres from Cross–Linkable Diblock Copolymers; Guo, et al; Macromolecules 1996, 29, 2487–2493.

Polymerized Micelles: Fact or Fancy?; Hamid, et al; J. Chem. Soc., Chem. Commun., 1986, 936–938.

Water–Soluble Nanospheres of Poly(2–cinnamoylethyl methacrylate)–block–poly(acrylic acid); Henselwood, et al; Macromolecules 1997, 30, 488–493.

Self–Assembly and Polymerization of Epoxy Resin–Amphipilic Block Copolymer Nanocomposites; Hillmyer, et al; J. Am. Chem. Soc. 1997, 119, 2749–2750.

Water–soluble Shell Cross–linked Knedels (SCK): Amphiphilic Nanospheres Composed of Polystyrene and Polyacrylic Acid Domains; Huang, et al; Polymer Preprints (ACS Division of Polymer Chemistry, Papers presented at the San Francisco, CA meeting, Apr. 1997); 38(1), 119–120.

Hydrogel–Coated Glassy Nanospheres: A Novel Method for the Synthesis of Shell Cross–Linked Knedels; Huang, et al; J. Am. Chem. Soc. 1997, 119, 11653–11659.

Core–Shell Type Polymer Microspheres Prepared from Block Copolymers; Ishizu, et al; Journal of Polymer Science: Part C: Polymer Letters, vol. 26, 281–286, 1988.

Surface changes on block copolymers by crosslinking of spherical microdomains; Koji Ishizu; Polymer, 1989, vol. 30, 793–798.

Shape changes on core–shell type multi–molecular micelles; Koji Ishizu; Polymer Communications 1989, vol. 30, 209–211.

Core–Shell Type Polymer Microspheres Prepared From Diblock Copolymer Films; Ishizu, et al; Polym.–Plast. Technol. Eng., 31(7&8), 607–633, 1992.

Poly(ethylene oxide) Macromonomers. 7. Micellar Polymerization in Water; Ito, et al; Macromolecules, vol. 24, No. 9, 2348–2354, 1991.

Poly(ethylene oxide) Macromonomers. 8. Preparation and Polymerization of w–Hydroxypoly(ethylene oxide) Macromonomers; Macromolecules, vol. 24, No. 14, 3977–3981, 1991.

Biologically erodable microspheres as potential oral drug delivery systems; Mathiowitz, et al; Nature, vol. 386, 410–414, 1997.

Double–walled polymer microspheres for controlled drug release; Pekarek, et al; Nature, vol. 367, 258–260, 1994.

Photochemical Stabilization of Block Copolymer Micelles; Prochazka, et al; Makromol. Chem. 180, 2521–2523, 1979.

Microspheres Deliver DNA; Rebecca Rawls; C&EN, 6. 1997.

Thermal recording material; Ricoh Co., Ltd.; Chem. Abstr., vol. 100, 1984, p. 589, Abstract 100:201044Z.

Synthesis of microspheres with 'hairy–ball' structures from poly(styrene–b–2–vinyl pyridine) diblock copolymers; Saito, et al; Polymer, 1992, vol. 33, No. 5, 1073–1077.

Flower type microgels: 1. Synthesis of the microgels; Saito, et al; Polymer, vol. 38, No. 1, 1997, 225–229.

Synthesis of poly(methacrylic acid) core/polystyrene shell type polymer microspheres; Saito, et al; Polymer, vol. 38, No. 7, 1997, 1725–1729.

A Novel Reactive Polymeric Micelle with Aldehyde Groups on its Surface; Scholz, et al; Macromolecules 1995, 28, 7295–7297.

Water–Soluble Knedel–like Structures: The Preparation of Shell–Cross–Linked Small Particles; Thurmond, II et al; J. Am. Chem. Soc. 1996, 118, 7239–7240.

The Study of Shell Cross–linked Knedels (SCK), Formation and Application; Thurmond, II et al; Polymer Preprints (ACS Division of Polymer Chemistry, Papers presented at the San Francisco, CA meeting, Apr. 1997) 38(1), 62–63.

The Synthesis of Shell Cross–linked Knedels (SCK's): The Ability to Control Size; Thurmond, II et al; Polymer Preprints (ACS Division of Polymer Chemistry, Papers Presented at the Las Vegas, NV meeting, Sep. 1997) 38(2), 592–593.

Shell Cross–Linked Knedels: A Synthetic Study of the Factors Affecting the Dimensions and Properties of Amphiphilic Core–Shell Nanospheres; Thurmond, II et al; J. Am. Chem. Soc., vol. 119, No. 28, 1997, 6656–6665.

From Dendrimers to Knedel–like Structures; Karen L. Wooley; Chem. Eur. J. 1997, 3, No. 9, 1397–1399.

Ion–Induced Morphological Changes in "Crew–Cut" Aggregates of Amphiphilic Block Copolymers; Zhang, et al; Science, vol. 272, 1996, 1777–1779.

D. Lee et al. "The Formation of "Inverted" Core–Shell Latexes" Journal of Polymer Science: Polymer Chemistry Edition, vol. 21 (1982) pp. 147–154.

Kim et al ACS Wash. Meeting 1990 Polymeric Materials Science and Engineering vol. 64, 67.*

K. Ishizu Polymer, 1989, vol. 30 pp. 793–798, May 1989.*

K. Ishizu Polymer Communications 1989, vol. 30 pp. 209–211, Jul. 1989.*

K. Ishizu et al. Poly–Plast. Tech. Eng 31(7 8) 607–633, 1992.*

K. Ishizu et al. Polymer Communications pp. 209–211, Jul. 1989.*

Chem. Ab. 1999:558788.*

Chem. Ab. 1999:238070.*

Chem. Ab. 1999:93622.*

* cited by examiner

PARTICLES COMPRISING AMPHIPHILIC COPOLYMERS, HAVING A CROSSLINKED SHELL DOMAIN AND AN INTERIOR CORE DOMAIN, USEFUL FOR PHARMACEUTICAL AND OTHER APPLICATIONS

This application claims the benefit of priority of U.S. Provisional Application Serial No. 60/020,693, filed Jun. 27, 1996.

STATEMENT REGARDING FEDERALLY SPONSORED RESEARCH

This invention was made with Government support under Grant No. DMR-9458025 awarded by the National Science Foundation. The Government has certain rights in this invention.

BACKGROUND OF THE INVENTION

1. Field of the Invention

The present invention relates to novel globular amphiphilic polymers. More specifically, the present invention relates to low polydispersity particles comprising amphiphilic copolymers, having a crosslinked shell domain, which can be permeable, and an interior core domain. The present invention also relates to methods for producing the particles. The invention particles can be used in a variety of applications, including removal of hydrophobic contaminants from aqueous solutions, recording materials, hydraulic fluids, coatings, chromatography, electrophoresis, drug delivery, catalysis, salvation, fat substitutes, delivery of herbicides and pesticides, combinatorial chemistry, DNA delivery, phase transfer reactions, and as fillers and reinforcement agents for plastics.

2. Description of Related Art

There is an interest in new classes of polymeric materials that have new and advanced physical, chemical, and mechanical properties. For example, Y. H. Kim reported hyperbranched polymers in *Advanced Materials*, 4, 764 (1992). Macrocycles were described by Y. Gan, et al. in *Polymer Preparation*, 34(1), 69 (1993). Rotaxanes were reported by Y. X. Shen, et al. in *Macrocycles*, 25, 2058 (1992). Two dimensional polymeric sheets have also been described (Stupp, S. I., et al., *Science*, 259, 59 (1993)).

Other polymeric materials with new and unusual behavior include dendrimers, described by D. A. Tomalia, et al. in *Angewandte Chemie International Edition English*, 29, 138 (1990). A review article on dendrimers is Ardoin, N., et al., *Bulletin de la Société Chimie*, 132(9), 875 (1995). Another review of dendrimer research is found in *Advances in Dendritic Materials*, Ed. G. R. Newkome, JAI Press, Greenwich, Conn., 1994–95, Vol. 1–2.

Products created from these polymers possess unusual behavior when compared to traditional linear polymers. For example, rigid sphere and micellar dendrimers can encapsulate molecules and act as carriers or pharmaceutical delivery agents (Jansen, J. F. G. A., et al., *Advanced Materials*, 7(6), 561 (1995). Another example of how dendrimers can be used as carriers or pharmaceutical delivery agents is described by Hawker, C. J., et al., *Journal of the Chemical Society, Perkins Transactions*, 1, 1287 (1983)).

However, dendrimers are costly, time-consuming to synthesize, limited in their chemistry, and limited in their size range.

Block copolymers consisting of segments that possess different properties (for example, solubility, polarity, and rigidity) are well known to self-assemble into polymer micelles when placed in an appropriate solvent. Examples are found in Quin, A., et al., *Macromolecules*, 27, 120–26 (1994); Astafieva, I I, et al., *Macromolecules*, 26, 7339–7352 (1993); and Kataoka, K. et al., *Journal of Controlled Release*, 24, 119–132 (1993). However, these assembled structures are most often held together by hydrophobic interactions, which are not as strong as covalent bonds, and can be easily destroyed upon dilution of the solution containing polymer micelles, or by shear forces. Once the hydrophobic interactions are destroyed, the structures disassemble. Also, such structures typically have very short life times, for example less than a second.

Core-shell type polymer nonoparticles having a crosslinked core have been prepared from diblock copolymer films (Ishizu, K., et al., *Polymer-Plastics Technology and Engineering*, 31(7&8), 607 (1992); Saito, R., et al., *Polymer*, 35, 866 (1994)). Another example of core-crosslinked polymer nonoparticles is the stars described by Martin, M. K., et al., "Anionic Polymerization," Ed. J. E. McGrath, ACS Symposium Series 166, American Chemical Society, 1981, pp. 557–590. Stars are limited in having only one polymerizable group per surfactant molecule. Other polymer nonoparticles with cross-linked cores have been prepared from cross-linkable diblock copolymers (Guo, A., et al., *Macromolecules*, 29, 2487 (1996)). The solid, cross-linked cores limit the absorptive properties, rigidity, and structures of these nanoparticles.

Until now, attempts to prepare core-shell type polymer nanoparticles having a crosslinked shell domain and an interior core domain have been unsuccessful. For example, D. Cochin, et al. reported in Macromolecules, 26, 5755 (1993) that attempts to prepare shell-crosslinked micelles failed when using amphiphilic molecules such as N-n-alkyl-N,N-dimethyl-N-(vinylbenzyl)ammonium chlorides.

S. Hamid and D. Sherrington reported in a kinetic analysis of micellar shell crosslinking, "On the contrary these kinetic parameters suggest that rapid exchange of polymerizable amphiphiles during the kinetic lifetime of a propagating radical should allow the possibility of growth to a high polymer (in reacting micelles at the expense of non-reacting ones), and the formation of particles of much bigger dimensions than micelles (i.e., a situation analogous to normal emulsion polymerization)." They suggest that "monomer exchange is too rapid to form a 'polymerized micelle'." (Hamid, S. and Sherrington, D., "Polymerized Micelles: Fact of Fancy?" *Journal of the Chemical Society, Chemical Communications*, p. 936 (1986).)

L. Zhang, et al. reported in *Science*, 272, 1777 (1996) that morphological changes of micelles prepared in aqueous media from highly asymmetric polystyrene-b-poly(acrylic acid) can be obtained by the addition of calcium chloride, sodium chloride, or hydrochloric acid. Such morphological changes included clumping or clustering or bridging between micelles. The morphologically changed micelles are limited in their use because of their propensity to clump and because the stability of this system is highly dependent on pH and ionic strength.

Presently, there has not been a successful synthesis from amphiphilic agents or surfactants of a low polydispersity nanoparticle having a permeable, covalently crosslinked shell domain and an interior core domain. The references discussed above demonstrate continuing efforts to provide such a means of carrying or delivering chemical agents such as pharmaceuticals.

SUMMARY OF THE INVENTION

The present invention furthers the efforts described above by providing novel low polydispersity particles, pharmaceutical, agricultural, and other compositions, and methods of use therefor.

Accordingly, among its various aspects, the present invention provides low polydispersity globular macromolecules, particles, or nanoparticles as shown in FIG. 1, wherein the particles comprise amphiphilic copolymers, having a crosslinked shell domain or peripheral layer, which can be permeable, and an interior core domain.

The particles of the present invention can comprise a hydrophilic, crosslinked, permeable shell domain and a hydrophobic interior core domain. The amphiphilic copolymers of the particles of the present invention can be crosslinked via functional groups within the hydrophilic shell domain. Such crosslinking can be achieved by condensation reactions, addition reactions, or chain polymerization reactions.

In another embodiment of the present invention, the particles comprising amphiphilic copolymers, having a crosslinked shell domain and an interior core domain, comprise a hydrophobic, crosslinked shell domain, which can be permeable, and a hydrophilic interior core domain. The amphiphilic copolymers of these particles can be crosslinked via functional groups within the hydrophobic shell domain by condensation reactions, addition reactions, or chain polymerization reactions.

In yet another embodiment, the present invention provides a composition comprising amphiphilic copolymers, haveing a crosslinked shell domain, which can be permeable, and an interior core domain.

In another aspect, the present invention provides a pharmaceutical composition, comprising particles comprising amphiphilic copolymers having a crosslinked shell domain, which can be permeable, and an interior core domain, or a pharmaceutically acceptable salt thereof, and a pharmaceutically acceptable carrier, excipient, or diluent. The pharmaceutical composition can further comprise a pharmaceutically active agent. The pharmaceutically active agent can be present within the particles.

In a further aspect, the present invention provides an agricultural composition, comprising particles comprising amphiphilic copolymers, having a crosslinked shell domain, which can be permeable, and an interior core domain, or an agronomically acceptable salt thereof, and an agronomically acceptable carrier, excipient, or diluent. The agricultural composition can further comprise a pesticidally/herbicidally active agent. The pesticidally/herbicidally active agent can be contained within the particles.

In yet a further aspect, the present invention also provides compositions suitable for use in foods, comprising particles comprising amphiphilic copolymers, having a crosslinked shell domain, which can be permeable, and an interior core domain, or a salt thereof acceptable for use in foods, and a carrier, excipient, or diluent suitable for use in foods.

In still a further aspect, the present invention also provides a fat substitute composition, comprising particles comprising amphiphilic copolymers, having a crosslinked shell domain, which can be permeable, and an interior core domain, or a gastronomically acceptable salt thereof, and a gastronomically acceptable carrier, excipient, or diluent. Such fat substitute compositions can be used in methods for simulating the presence of fat in food compositions or additives by including such fat substitute compositions in food materials.

The present invention also provides compositions suitable for use in cosmetics, comprising particles comprising amphiphilic copolymers, having a crosslinked shell domain, which can be permeable, and an interior core domain, or a cosmetically salt thereof, and a carrier, excipient, or diluent suitable for use in cosmetics.

In a further aspect, the present invention provides compositions suitable for use in chromatography or electrophoresis, comprising particles comprising amphiphilic copolymers, having a crosslinked shell domain, which can be permeable, and an interior core domain, or a chromatographically or electrophoretically acceptable salt thereof, and a chromatographically or electrophoretically acceptable carrier, continuous phase, mobile phase, or diluent. Such chromatographic or electrophoretic compositions can be used in methods for separating components of mixtures. These methods can comprise introducing a mixture of components to be separated into a column containing particles of the present invention or onto a substrate coated with particles of the present invention, passing an appropriate solvent through the column or over the particle-coated substrate to separate components of the mixture, and recovering or detecting separated components of the mixture. In the case of electrophoretic separations, an electric potential is applied to the column or particle-coated substrate using conditions which are known in the art. In another aspect, the present invention provides a method for delivering a nucleic acid molecule to a cell, tissue, or organ, comprising contacting the cell, tissue, or organ, in vivo or in vitro, with a composition containing a particle of the present invention and the nucleic acid molecule for a period time sufficient to deliver the nucleic acid molecule to the cell, tissue, or organ. The nucleic acid molecule can, for example, be present on the surface of the particle, or within the particle. The nucleic acid molecule can be DNA or RNA, for example, an antisense oligonucleotide, a vector, or any other type of nucleic acid molecule commonly employed in genetic engineering techniques. In still another aspect, the present invention provides a method for separating components of a solvent mixture, comprising contacting the solvent mixture with particles of the present invention for a period of time sufficient for one or more of the components of the solvent mixture to associate with the particles, and separating the particles from the remaining solvent.

In a further aspect, the present invention provides a method of synthesizing a polymer, including biopolymers, for example a nucleic acid, peptide, polypeptide, or protein, comprising associating or affixing a first monomer to an active site present on the surface of a particle of the present invention, and subsequently covalently binding successive monomers to the first monomer to produce a polymer chain. The polymer can remain attached to the particle or can be cleaved from the particle by methods known in the art. In still a further aspect, the present invention provides a method of synthesizing a derivative compound, comprising associating or affixing a substrate molecule to an active site present on the surface of a particle of the present invention, and subsequently performing reactions on the substrate molecule to produce the derivative compound. The derivative compound can remain attached to the particle or it can be cleaved from the particle by methods known in the art. Such a method can be used to prepare a single derivative compound or a mixture of derivative compounds.

In yet a further aspect, the present invention also provides a method of delivering a pharmaceutically active agent to a cell, tissue, or organ, comprising contacting the cell, tissue, or organ, in vivo or in vitro, with a composition containing an effective amount of particles comprising amphiphilic copolymers, having a crosslinked shell domain, which can be permeable, and an interior core domain, and further comprising a pharmaceutically active agent. The pharmaceutically active agent can be contained within the particles. In these methods, the contact is for a period of time sufficient to introduce the pharmaceutically active agent to the locus of the cell, tissue, or organ.

In yet a further aspect, the present invention also provides a method of delivering a pesticidally active agent to a plant or animal, comprising contacting the plant or animal with a composition containing an effective amount of particles comprising amphiphilic polymers, having a crosslinked shell domain, which can be permeable, and an interior core domain, and further comprising a pesticidally active agent. The pesticidally active agent can be contained within the particles. In these methods, the contact is for a period of time sufficient to introduce the pesticidally active agent to the plant or animal.

In yet another aspect, the present invention also provides a method of reducing bile acid uptake in a mammal, comprising administering to the mammal a bile acid uptake-reducing effective amount of particles comprising amphiphilic copolymers, having a crosslinked shell domain, which can be permeable, and an interior core domain, the particles being administered for a period of time effective to reduce bile acid uptake in the mammal.

In still another aspect, the present invention also provides a method of reducing blood serum cholesterol in a mammal, comprising administering to the mammal a blood serum cholesterol-reducing effective amount of particles comprising amphiphilic copolymers, having a crosslinked An shell domain, which can be permeable, and an interior core domain, the particles being administered for a period of time effective to reduce bile acid uptake in the mammal.

Other uses for the particles of this invention include size standards, use in coatings (for example, latex paints), and solvent compatiblizers.

In yet another aspect, the present invention also provides processes for the preparation of particles of the present invention.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent from this detailed description to those skilled in the art.

BRIEF DESCRIPTION OF THE DRAWINGS

The above and other objects, features, and advantages of the present invention will be better understood from the following detailed description taken in conjunction with the accompanying drawing, all of which are given by way of illustration only, and are not limitative of the present invention, in which FIG. 1 is a schematic diagram illustrating the anatomy of particles of the present invention.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Definitions

In order to help the reader understand the following detailed description, the following definitions are provided:

"Alkyl", "alkenyl," and "alkynyl" unless otherwise noted are each straight chain or branched chain hydrocarbons of from one to twenty carbons for alkyl or two to twenty carbons for alkenyl and alkynyl in the present invention and therefore mean, for example, methyl, ethyl, propyl, butyl, pentyl or hexyl and ethenyl, propenyl, butenyl, pentenyl, or hexenyl and ethynyl, propynyl, butynyl, pentynyl, or hexynyl respectively and isomers thereof.

"Aryl" means a fully unsaturated mono- or multi-ring carbocycle, including, but not limited to, substituted or unsubstituted phenyl, naphthyl, or anthracenyl.

"Heterocycle" means a saturated or unsaturated mono- or multi-ring carbocycle wherein one or more carbon atoms can be replaced by N, S, P, or O.

The term "heteroaryl" means an aromatically unsaturated heterocycle.

In either "heterocycle" or "heteroaryl," the point of attachment to the molecule of interest can be at the heteroatom or elsewhere within the ring.

The term "quaternary heterocycle" means a heterocycle in which one or more of the heteroatoms, for example, O, N, S, or P, has such a number of bonds that it is positively charged. The point of attachment of the quaternary heterocycle to the molecule of interest can be at a heteroatom or elsewhere.

The term "quaternary heteroaryl" means a heteroaryl in which one or more of the heteroatoms, for example, O, N, S, or P, has such a number of bonds that it is positively charged. The point of attachment of the quaternary heteroaryl to the molecule of interest can be at a heteroatom or elsewhere.

The term "halogen" means a fluoro, chloro, bromo or iodo group.

The term "haloalkyl" means alkyl substituted with one or more halogens.

The term "cycloalkyl" means a mono- or multi-ringed carbocycle wherein each ring contains three to ten carbon atoms, and wherein any ring can contain one or more double or triple bonds.

The term "diyl" means a diradical moiety wherein said moiety has two points of attachment to molecules of interest.

The term "oxo" means a doubly bonded oxygen.

The term "polyalkyl" means a branched or straight hydrocarbon chain having a molecular weight up to about 20,000, more preferably up to about 10,000, most preferably up to about 5,000.

The term "polyethery" means a polyalkyl wherein one or ore carbons are replaced by oxygen, wherein the polyether as a molecular weight up to about 20,000, more preferably to about 10,000, most preferably up to about 5,000.

The term "polyalkoxy" means a polymer of alkylene oxides, wherein the polyalkoxy has a molecular weight up to about 100,000, more preferably up to about 50,000, most preferably up to about 10,000.

The term "alkylammoniumalkyl" means a $NH_2$ group or a mono-, di- or tri-substituted amino group, any of which is bonded to an alkyl wherein said alkyl is bonded to the molecule of interest.

When used in combination, for example "alkylaryl" or "arylalkyl," the individual terms listed above have the meaning indicated above.

The term "shell domain" means the outermost domain or peripheral layer of a particle of the present invention. When produced in a hydrophilic continuous medium, the peripheral layer of the micelles giving rise to such particles (and the peripheral layer of the particles themselves) is substantially hydrophilic; when produced in a hydrophobic continuous medium, the peripheral layer of the micelles giving rise to such particles (and the peripheral layer of the particles themselves) is substantially hydrophobic.

The term "interior core domain" means the domain of a micelle or particle interior to the shell domain.

The term "amphiphilic copolymer" means a copolymer which contains at least one hydrophilic domain and at least one hydrophobic domain.

The term "block copolymer" means a linear polymer having regions or blocks along its backbone chain which are characterized by similar hydrophilicity, hydrophobicity, or chemistry. The term "diblock copolymer" means a block copolymer comprising two blocks. The term "triblock copolymer" means a block copolymer comprising three blocks. The term "multiblock copolymer" means a block copolymer comprising a plurality of blocks.

The term "graft copolymer" means a linear or ultilinear polymer to which a plurality of side chains have been grafted.

The term "hydrophilic/lipophilic balance" means the ratio of the sum of the formula weights of the hydrophilic regions of a copolymer divided by the sum of the formula weights of the hydrophobic regions of the copolymer.

The term "titrimetric crosslinking reagent" means a crosslinking reagent comprising two or more reactive functional groups, each functional group being capable of reacting with a functionality on an amphiphilic copolymer.

The term "swollen state" means the state of a particle after it has been swollen by solvent. This can include any state of swelling up to the maximum dimensions for that particle. The maximum dimensions for a given particle depend, of course, on the solvent employed.

The term "unswollen state" means the state of a particle after solvent has been removed.

The term "aspect ratio" means the ratio of the length of a micelle divided by its width or diameter, as applicable. The term "degree of crosslinking" means the percent of crosslinking actually accomplished relative to the maximum crosslinking possible.

The term "aggregation number" means the average number of amphiphilic copolymer molecules per micelle or particle.

The term "glass transition temperature" means the temperature at which a polymer changes from a glassy, hard state to a flexible state.

The term "intramicellarly" means within a micelle.

The term "intermicellarly" means between micelles.

The term "micelle" includes without limitation micelles having shapes of spheres, cylinders, discs, needles, cones, vesicles, globules, rods, elipsoids, and any other shape that a micelle can assume under the conditions described herein, or any other shape that can be adopted through aggregation of the amphiphilic copolymers.

The term "particle" includes, but is not limited to, nanoparticles. The shape of the particles can include without limitation spheres, cylinders, discs, needles, cones, vesicles, globules, rods, elipsoids, and any other shape that a micelle can assume under the conditions described herein, or any other shape that can be adopted through aggregation of the amphiphilic copolymers.

The term "nanoparticle" means a particle, the largest dimension of which is less than one micron.

The term "monomer" means a molecule which is capable of combining with a number of like or unlike molecules to form a polymer.

The term "pericyclic reaction" means cycloaddition reactions, electrocyclic reactions, sigmatropic reactions, cheleotropic reactions, and group transfer reactions.

The term "pharmaceutically active agent" means any physiologically or pharmacologically active substance that produces a local or systemic effect in animals, including warm-blooded mammals, humans, and primates; avians; household, sport, and farm animals; laboratory animals; fishes; reptiles; and zoo animals.

The terms "homogeneous" and heterogeneous as they are used herein are each used in two different contexts. With respect to the amphiphilic copolymer blocks per se, the term "homogeneous" pertains to an amphiphilic copolymer block having a uniform composition or structure. In this context, the term "heterogeneous" pertains to an amphiphilic copolymer block having a nonuniform composition or structure. With respect to domains of the particles per se, the term "homogeneous" pertains to a domain having a uniform composition or structure. In this context, the term "heterogeneous" pertains to a domain having a nonuniform composition or structure.

The term "mean particle diameter" means the average value of the various diameters of regularly or irregularly shaped particles.

The term "permeable" pertains to the property of a domain whereby selected atoms or molecules can pass through the domain.

The term "pesticidally active agent" means any agent that destroys pests. Such agents can include, without limitation, herbicides, insecticides, fungicides, nematocides, acaricides, bactericides, biocides, rodenticides, and the like.

Particles of the Invention

The particles of the present invention comprise aamphiphilic copolymers, and have a crosslinked shell domain, which can be permeable, and an interior core domain. Such particles can comprise a hydrophilic, crosslinked, permeable shell domain and a hydrophobic interior core domain. The amphiphilic copolymers of the particles can be crosslinked via functional groups within the hydrophilic shell domain, for example by condensation reactions, addition reactions, or chain polymerization reactions.

In another embodiment of the present invention, the hydrophobic interior core domain of the particles can also be crosslinked via functional groups in their hydrophobic domains.

In another embodiment of the present invention, the particles comprising amphiphilic copolymers having a crosslinked shell domain and an interior core domain can comprise a hydrophobic, crosslinked shell domain, which can be permeable, and a hydrophilic interior core domain. The amphiphilic copolymers of such particles can be crosslinked via functional groups within the hydrophobic shell domain, for example by condensation reactions, addition reactions, or chain polymerization reactions. In another embodiment of the present invention, the hydrophilic interior core domain of such particles can also be crosslinked. In this case, the amphiphilic copolymers can be crosslinked via functional groups in their hydrophilic domains.

In yet another embodiment, the particles of the present invention comprise aliphatic copolymers, comprising an outermost crosslinked domain, which can be permeable, a series of additional crosslinked (permeable) domains, and a domain interior to each of the crosslinked (permeable) domains, producing an "onion-like" structure.

Amhiphilic Copolymers

Amphiphilic copolymers useful in the present invention can be selected from amphiphilic diblock copolymers, amphiphilic triblock copolymers, amphiphilic multiblock copolymers, and amphiphilic graft copolymers.

The hydrophilic blocks of the amphiphilic diblock, triblock, or multiblock copolymers can have formula weights in the range from about 1,000 to about 500,000, preferably from about 2,500 to about 250,000, more preferably from about 5,000 to about 100,000. The hydrophobic blocks of the amphiphilic diblock, triblock, or multiblock copolymers useful in the present invention can have formula weights in the range of from about 1,000 to about 500,000, preferably from about 2,500 to about 250,000, more preferably from about 5,000 to about 100,000.

Amphiphilic graft copolymers useful in the present invention possess rotatable side chain block regions that can rotate or fold to become part of the crosslinked shell domain or the interior core domain of the particles of the present invention. The number of side chains present in each of the amphiphilic graft copolymers can be in the range of from about 10 to about 11000, preferably from about 25 to about 750, more preferably from about 50 to about 250.

The formula weights of the various blocks in the amphiphilic copolymers can be varied independently of each other.

Hydrophilic Monomers and Polymers

Examples of monomer repeat units that can be used in the preparation of hydrophilic blocks are listed in Table 1.

TABLE 1

Monomers Units Useful as Repeat Units in Hydrophilic Blocks

| Polyacrylic acid | Poly(metal acrylate) M = Li, Na, K, Cs |
| --- | --- |
| Polyacrylamide R = H, alkyl | Poly(methacrylic acid) |
| Poly(metal methacrylate) M = Li, Na, K, Cs | Polymethacrylamide R = H, alkyl |
| Polystyrene sulfonic acid | Polystyrene sulfonic acid, metal salt M = Li, Na, K, Cs |
| Polystyrene carboxylic acid | Polystyrene carboxylic acid, metal salt M = Li, Na, K, Cs |
| Poly(vinyl alcohol) | R = H, alkyl Poly(4-vinyl-N-alkyl]pyridinium halide) Percent quaternization 10% to 70% |
| R = H, alkyl Poly(2-vinyl-N-alkyl]pyridinium halide) | |
| Poly(hydroxyethyl methacrylate) | Poly(itaconic acid) |
| Poly(N,N,N-trialkyl-4-vinylphenylammonium halide) | Poly(N,N,N-trialkyl-4-vinylbenzylammonium halide) |

TABLE 1-continued

Poly(N,N,N-trialkyl-4-vinylphenethylammonium halide) — Percent quaternization 10% to 70%

Amino acids which make up hydrophilic block

Serine

Threonine

Tyrosine

Lysine

Arginine

Histidine

Aspartic acid

Glutamic acid

A monomer repeat unit which is particularly useful in the hydrophilic blocks of the present invention is a 4-vinyl-N-(methyl(4'-styrenyl)pyridinium salt and has the formula (I):

(I)

wherein $X^-$ is a pharmaceutically or agronomically acceptable anion.

Another class of monomer repeat unit which is particularly useful in the hydrophilic blocks of the present invention includes acrylic acids, their salts, and esters and amides thereof.

Examples of polymers that can be used as hydrophilic blocks are listed in Table 2. One skilled in the art, of course, will after reading this disclosure recognize that reactive functionalities can be substituted into any of the hydrophilic blocks useful in this invention.

Table 2. Polymers Useful as Hydrophilic Blocks
Poly(sodium 1-carboxylatoethylene)
Poly(5-hydroxy-1-pentene)
5,8-poly-5,7-dodecadiynediol
10,13-poly-10,12-heptacosadiynoic acid
2,5-poly-2,4-hexadienedioic acid
2,5-poly-2,4-hexadienoic acid
(6-amino)-2,5-poly-2,4-hexadienoic acid
(6-amino)2,5-poly-2,4-hexadienoic acid, hydrochloride
2,5-poly-2,4-hexadiynediol
10,13-poly-10,12-nonacosadiynoic acid
2,5-poly-2,4,6-octatriynediol
10,13-poly-10,12-pentacosadiynoic acid
2,5-poly-5-phenyl-2,4-pentadienoic acid
Poly(2-aminoisobutyric acid), dichloroacetic acid complex
Poly(L-arginine)
Poly(L-arginine,hydrochloride)
Poly(L-nitroarginine)
Poly(L-aspartic acid)
Poly(beta-benzyl-L-aspartic acid)
Poly[beta-(p-chloro-benyl)-L-aspartic acid]
Poly(beta-ethyl-L-aspartic acid)
Poly[beta-(2-phenyl-ethyl)-L-aspartic acid]

Poly(alpha-isobutyl-L-aspartic acid)
Poly(beta-N-propyl-L-aspartic acid)
Poly(2,4-diaminobutyric acid)
Poly(N-benzyloxycarbonyl-2,4-diaminobutyric acid)
Poly(D-glutamic acid)
Poly(gamma-benzyl-D-glutamic acid)
Poly(gamma-m-chloro-benzyl-D-glutamic acid)
Poly(gamma-o-chloro-benzyl-D-glutamic acid)
Poly(gamma-p-chloro-benzyl-D-glutamic acid)
Poly(gamma-methyl-D-glutamic.acid)
Poly(gamma-phthalimidomethyl-L-glutamic acid)
Poly(L-glutamic acid)
Poly(gamma-N-amyl-L-glutamic acid)
Poly(gamma-benzyl-L-glutamic acid)
Poly(gamma-m-chloro-benzyl-L-glutamic acid)
Poly(gamma-o-chloro-benzyl-L-glutamic acid)
Poly(gamma-p-chloro-benzyl-L-glutamic acid)
Poly(gamma-N-butyl-L-glutamic acid)
Poly(gamma-N-dodecyl-L-glutamic acid)
Poly(gamma-N-ethyl-L-glutamic acid)
Poly[gamma-N-(2-chloro-ethyl)-L-glutamic acid]
Poly[gamma-N-(2-phenyl-ethyl)-L-glutamic acid]
Poly(gamma-N-hexyl-L-glutamic acid)
Poly(gamma-methyl-L-glutamic acid)
Poly(gamma-methyl-L-glutamic acid), dimethyl phthalate complex
Poly(gamma-N-octyl-L-glutamic acid)
Poly(gamma-N-propyl-L-glutamic acid)
Poly[gamma-N-(3-phenyl-propyl)-L-glutamic acid]
Poly(L-glutamine)
Poly[N5-(4-hydroxybutyl)-L-glutamine]
Poly[N5-(2-hydroxyethyl)-L-glutamine]
Poly[N5-(3-hydroxypropyl)-L-glutamine]
Poly(D-glutamyl-L-glutamic acid)
Poly(gamma-benzyl-D-glutamyl-L-glutamic acid)
Poly(gamma-ethyl-D-glutamyl-L-glutamic acid)
Poly[gamma-(2-phenyl-ethyl)-D-glutamyl-L-glutamic acid]
Poly(L-histidine)
Poly(1-benzyl-L-histidine)
Poly(L-histidine), hydrochloride
Poly(gamma-hydroxy-L-alpha-aminoveleric acid)
Poly(L-lysine)
Poly(E-benzyloxycarbonyl-L-lysine)
Poly(L-lysine), hydrobromide
Poly(L-methionine-s-carboxymethylthetin)
Poly(L-methionine-s-methylsulfonium bromide)
Poly(L-serine)
Poly(gamma-hydroxy-L-proline)
Poly(hydroxymethylene)
Poly(1-hydroxytrimethylene)
Poly(3,3-bishydroxymethyltrimethylene oxide)
Poly(3-hydroxytrimethylene oxide)
Poly(vinyl alcohol)
Poly(ethylene glycol)
Poly(2-methyl-vinyl alcohol)
Poly(hydroxymethylene)
Poly(cinnamic acid)
Poly(crotonic acid)
Poly(3-bromo acrylic acid)
Poly(3-ethyl acrylic acid)
Poly(N-acetyl-alpha-amino acrylic acid)
Poly(alpha-bromoacrylic acid)
Poly(alpha-chloroacrylic acid)
Poly(alpha-fluoroacrylic acid)
Poly(sodium alpha-chloroacrylate)
Poly(3-oxa-5-hydroxypentyl methacrylate)
Poly(2-hydroxyethyl acrylate)
Poly(2-hydroxypropyl acrylate)
Poly(beta-chloro-2-hydroxypropyl acrylate)
Poly[N-(2-hydroxyethyl)-3,6-dichlorocarbazolyl acrylate]
Poly[N-(2-hydroxyethyl)carbazolyl acrylate]
Poly(acryloyl-beta-hydroxyethyl-3,5-dimitrobenzoat)
Poly(methacryloyl-beta-hydroxyethyl-3,5-dimitrobenzoat)
Poly(N-(2-hydroxyethyl)carbazolyl methacrylate)
Poly(2-hydroxyethyl methacrylate)
Poly(2-hydroxypropyl methacrylate)
Poly(3-methoxy-2-hydroxypropyl methacrylate)
Poly[1-(2-hydroxyethyl)pyridiniumbenzene sulfonate methacrylate]
Poly[1-(2-hydroxyethyl)trimethylamoniumbenzene sulfonate methacrylate]
Poly[N-(2-hydroxyethyl)phthalimido methacrylate]
Poly[N-(hydroxyethyl)carbazolyl methacrylate]
Poly(N-ethyl-3-hydroxymethylcarbazolyl methacrylate)
Poly(2-sulfonic acid-ethyl methacrylate)
Poly(2-trimethylammonium ethyl methacrylate chloride)
Poly(2-trimethylammoniummethyl methacrylate chloride)
Poly(methacrylonitrile)
Poly(thiolacrylic acid)
Poly(acrylonitrile)
Poly(acrylamide)
Poly(methacrylamide)
Poly(N,N-dimethylacrylamide)
Poly[(N-methylol)acrylamide]
Poly[N-methoxymethyl methacrylamide]
Poly(N-methyl methacrylamide)
Poly(N-2-methoxyethyl methacrylamide)
Poly[N-(2-hydroxypropyl)methacrylamide]
Poly(2-methylpropanesulfonate sodium 2-acrylamido)
Poly(2-methylpropanesulfonic acid 2-acrylamido)
Poly[(p-amino)-styrene]
Poly[4-(4-hydroxybutoxymethyl)styrene]
Poly[4-(2-hydroxyethoxymethyl)styrene]
Poly[4-(2-hydroxyiminoethyl)styrene]
Poly[4-(1-hydroxyiminoethyl)styrene]
Poly[4-(n-2-hydroxybutyl) styrene]
Poly[4-(1-hydroxy-3-dimethylaminopropyl)styrene]
Poly[4-(1-hydroxy-1-methylbutyl)styrene]
Poly[4-(1-hydroxy-1-methylethyl)styrene]
Poly[4-(1-hydroxy-1-methylhexyl)styrene]
Poly[4-(1-hydroxy-1-methylpentyl)styrene]
Poly[4-(1-hydroxy-1-methylpropyl)styrene]
Poly(2-hydroxymethylstyrene)
Poly(3-hydroxymethylstyrene)
Poly(4-hydroxymethylstyrene)
Poly(4-hydroxy styrene)
Poly[p-1-(2-hydroxybutyl)-styrene]
Poly[p-1-(2-hydroxypropyl)-styrene]
Poly[p-2-(2-hydroxypropyl)-styrene]
Poly[4-(1-hydroxy-3-morpholinopropyl)styrene]
Poly[4-(1-hydroxy-3-piperidinopropyl)styrene]
Poly(p-octylamine sulfonate styrene)
Poly(2-carboxystyrene)
Poly(4-carboxystyrene)
Poly(styrene sulfonic acid)
Poly(vinyl sulfonic acid)
Poly[N-(2-hydroxypropyl)methacrylamide]
Poly[oxy(hydroxyphosphinylidene)]
Poly(9-vinyladenine)
Poly(vinyl carbanilate)
Poly(vinylpyrrolidone)
Poly(vinyl succinamic acid)
Poly(N-isopropylacrylamide)
Poly(methacrylic acid)

Poly(itaconic acid)
Poly(glycidyl methyl itaconate)
Poly(monomethyl itaconate)
Poly[N-(p-chlorophenyl) itaconimide]
Poly[N-(p-tolyl)itaconimide]
Poly[N-(2-chloroethyl)itaconimide]
Poly[N-(4-acetoxyphenyl)itaconimide]
Poly[N-(4-chlorophenyl)itaconimide]
Poly[N-(4-ethoxycarbonylphenyl)itaconimide]
Poly(N-benzylitaconimide)
Poly(N-butylitaconimide)
Poly(N-ethylitaconimide)
Poly(N-isopropylitaconimide)
Poly(N-isobutylitaconimide)
Poly(N-methylitaconimide)
Poly(N-naphthylitaconimide)
Poly(N-phenylitaconimide)
Poly(N-propylitaconimide)
Poly(N-tolylitaconimide)
Poly(alpha-chlorovinyl acetic acid)
Poly(carboxychloromethyl ethylene)
Poly(4-vinyl phenol)
Poly(o-hydroxy-vinylphenylketone)
Poly(alpha-phenylvinyl phosphonic acid)
Poly[(1,2,5-trimethyl-4,4i-hydroxypyridiumchlorideethynyl)ethylene]
Poly(allyl alcohol)
Poly(acrylic acid)
Poly[2-(3-sodium sulfonato-2-methylpropyl) methacrylamide]
Poly(3-sodium sulfonatopropyl methacrylate)
Poly(3-oxa-5-hydroxypentyl methacrylate)
Poly(diethylenegycol dimethacrylate)
Poly(trimethyleneglycol dimethacrylate)
Poly(triethyleneglycol dimethacrylate)
Poly(ethyleneglycol N-phenylcarbamate methacrylate)
Poly(acryloyl-L-glutamic acid)
Poly(methacryloyl-L-glutamic acid)
Poly(butadiene-1-carboxylic acid)
Poly(crotonate acid)
Poly(trans-4-ethoxy-2,4-pentadienoic acid)
Poly(alpha-phenylvinyl phosphonic acid)
Poly(vinylbenzoic acid)
Poly(2-acryloyloxy benzoic acid)
Poly[1-(2-hydroxyethylthio)-1,3-butadiene]
Poly(2,5-dicarboxylic acid -1-hexene)
Poly(3-hydroxyisoprene)
Poly(alpha-phenylvinyl phosphonic acid)
Poly(2-chloro-3-hydroxy propene)
Poly(2-p-vinylphenylpropanol)
Poly(o-hydroxy-vinylphenylketone)
Poly(1-vinyl-3-benzyl-imidazolium chloride)
Poly(4-vinylbenzyltrimethylammonium chloride)
Poly(4-vinylbenzyldimethyl vinylbenzyl ammonium chloride)
Poly(4-vinylbenzyldimethyl methacryloyl ammonium chloride)
Poly(4-vinylbenzyldimethyl acryloyl ammonium chloride)
Poly(4-vinylbenzyldimethyl allyl ammonium chloride)
Poly(4-vinylphenyltrimethylammonium chloride)
Poly(4-vinylphenyl dimethyl vinylbenzyl ammonium chloride)
Poly(4-vinylphenyl dimethyl methacryloyl ammonium chloride)
Poly(4-vinylphenyl dimethyl acryloyl ammonium chloride)
Poly(4-vinylphenyl dimethyl allyl ammonium chloride)
Poly(4-vinylphenethyltrimethylammonium chloride)
Poly(4-vinylphenethyldimethyl vinylbenzyl ammonium chloride)
Poly(4-vinylphenethyldimethyl methacryloyl ammonium chloride)
Poly(4-vinylphenethyldimethyl acryloyl ammonium chloride)
Poly(4-vinylphenethyldimethyl allyl ammonium chloride)
Poly(vinyl acetate)
Poly(vinyl butyral)
Poly(acetaldehyde)
Poly(ethylene oxide)
Poly(2-cyanoethyloxymethylene oxide)
Poly[(methoxymethyl)ethylene oxide]
Poly(methylene sulfide)
Poly(ethylene disulfide)
Poly(ethylene sulfide)
Poly(ethylene tetrasulfide)
Poly(methylene disulfide)
Poly(trimethylene disulfide)
Poly(ethylene amine)
Poly(propylene amine)
Poly(4-vinyl-N-methylpyridinium chloride)
Poly(4-vinyl-N-ethylpyridinium chloride)
Poly[4-(2-dimethylaminoethoxycarbonyl)styrene], hydrochloride
Poly(4-vinylpyridine), hydrogen chloride
Poly(4-vinyl-N-vinylbenzylpyridinium chloride)
Poly(4-vinyl-N-methacryloylpyridinium chloride)
Poly(4-vinyl-N-acryloylpyridinium chloride)
Poly(4-vinyl-N-allylpyridinium chloride)
Poly(2-vinyl-N-methylpyridinium chloride)
Poly(2-vinyl-N-ethylpyridinium chloride)
Poly(2-vinyl-N-vinylbenzylpyridinium chloride)
Poly(2-vinyl-N-methacryloylpyridinium chloride)
Poly(2-vinyl-N-acryloylpyridinium chloride)
Poly(2-vinyl-N-allylpyridinium chloride)
Poly(2-vinylpyridine), hydrogen chloride Hydrophobic Monomers and Polymers The hydrophobic blocks of the amphiphilic diblock, triblock, or multiblock copolymers useful in the present invention can have formula weights in the range of from about 1,000 to about 500,000, preferably from about 2,500 to about 250,000, more preferably from about 5,000 to about 100,000.

Examples of monomer repeat units that can be used in the preparation of hydrophobic blocks are listed in Table 3.

TABLE 3

Monomers Units Useful as Repeat Units in Hydrophobic Blocks

Hydrophobic Repeat Units

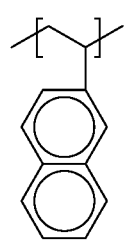 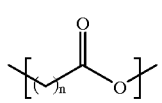

Poly(2-vinylnaphthalene)    Poly(caprolactam)

TABLE 3-continued
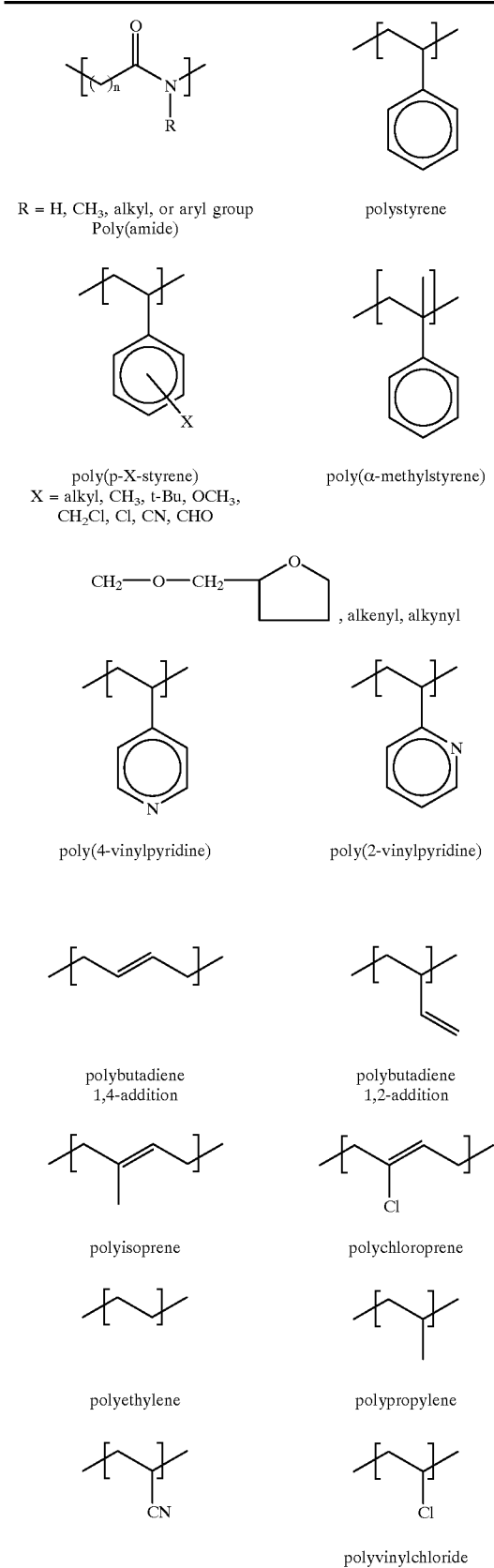
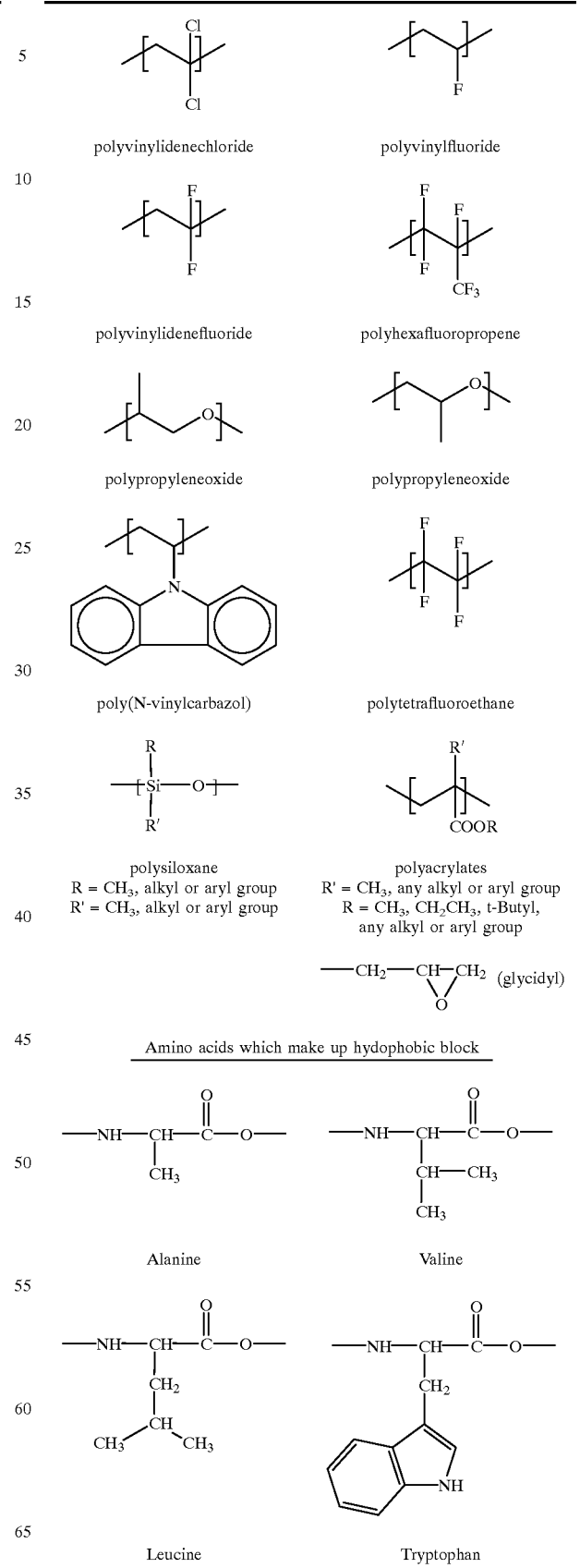

TABLE 3-continued

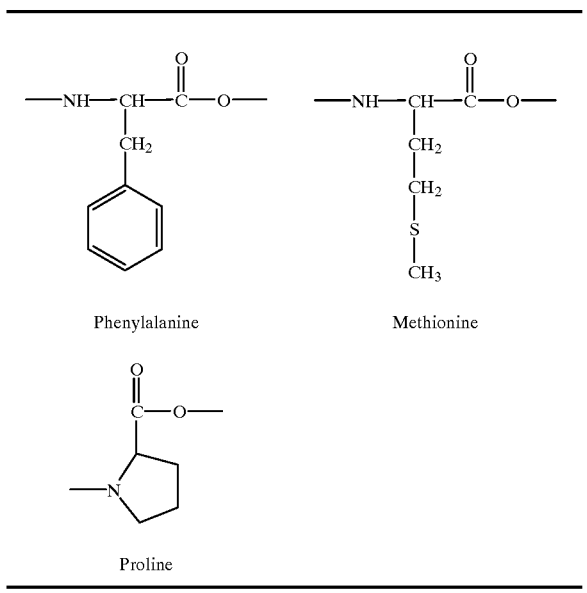

Phenylalanine      Methionine

Proline

Examples of polymers that can be used as hydrophobic blocks are listed in Table 4. One skilled in the art, of course, will after reading this disclosure recognize that reactive functionalities can be substituted into any of the hydrophobic blocks useful in this invention.

Table 4. Polymers Useful as Hydrophobic Blocks

Poly[thio(2-chlorotrimethylene)thiotrimethylene]
Poly[thio(1-iodiethylene)thio(5-bromo-3-chloropentamethylene)
Poly[imino(1-oxoethylene)silylenetrimethylene]
Poly(oxyiminomethylenehydrazomethylene)
Poly[oxy(1,1-dichloroethylene)imino(1-oxoethylene)]
Poly[(6-chloro-1-cyclohexen-1,3-ylene)-1-bromoethylene]
Poly[(dimethylimino)ethylenebromide]
Poly[(oxycarbonyloxymethyl)ethylene]
Poly(1,1-dimethylethylene)
Poly(1-methyl-1-butenylene)
Poly[(2-propyl-1,3-dioxane-4,6-diyl)methylene]
Poly[1-(methoxycarbonyl)ethylene]
Poly(glycyl-6-aminocarproic acid)
Poly(glycyl-6-aminocarproic acid-3-amino-propionic acid)
Poly(L-alanyl-4-aminobutyric acid)
Poly(L-alanyl-6-aminocaproic acid)
Poly(L-alanyl-3-aminopropionic acid)
Poly(L-alanyl-5-aminovaleric acid)
Poly(2-aminocyclopentylenecarboxy acid)
Poly(2-aminoethylenesulfonic acid)
Poly(3-aminopropionic acid)
Poly(1-methyl-3-aminopropionic acid)
Poly[(3-aminocyclobutylene)-propionic acid]
Poly[(2,2-dimethyl-3-aminocyclobutylene)-propionic acid]
Poly(2-aminoisobutyric acid)
Poly(3-aminobutyric acid)
Poly(4-aminobutyric acid)
Poly(5-aminovaleric acid)
Poly(6-aminocaproic acid)
Poly(D-(-)-3-methyl-6-aminocaproic acid)
Poly(6-methyl-6-aminocaproic acid)
Poly(6-aminothiocaproic acid)
Poly(7-aminoenanthic acid)
Poly((R)-3-methyl-7-aminoenanthic acid)
Poly((S)-4-methyl-7-aminoenanthic acid)
Poly((R)-5-methyl-7-aminoenanthic acid)
Poly((R)-6-methyl-7-aminoenanthic acid)
Poly(N-methyl-7-aminoenanthic acid)
Poly(7-aminothioenanthic acid)
Poly(8-aminocaprylic acid)
Poly(9-aminopelargonic acid)
Poly(10-aminocapric acid)
Poly(11-aminoundecanoic acid)
Poly(N-allyl-11-aminoundecanoic acid)
Poly(N-ethyl-11-aminoundecanoic acid)
Poly(2-methyl-11-aminoundecanoic acid)
Poly(N-methyl-11-aminoundecanoic acid)
Poly(N-phenyl-11-aminoundecanoic acid)
Poly(N-piperazinyl-11-aminoundecanoic acid)
Poly(12-aminolauric acid)
Poly(aminoformic acid)
Poly(N-butyl-aminoformic acid)
Poly(2-methyl-N-butyl-aminoformic acid)
Poly(N-phenyl-aminoformic acid)
Poly[imino-(1-oxo-2,3-dimethyltrimethylene)]
Poly[imino-(1-oxo-3-ethyltrimethylene)]
Poly[imino-(1-oxo-4-methylhexamethylene)]
Poly[imino-(1-oxo-3-methylhexamethylene)]
Poly[imino-(1-oxo-5-methylhexamethylene)]
Poly[imino-(1-oxo-3-methyl-6-isopropylhexamethylene)]
Poly[imino-(1-oxo-3-methyltrimethylene)]
Poly[imino-(1-oxo-3-vinyltrimethylene)]
Poly[N-(2-methylbutyl)iminocarbonyl]
Poly[N-(phenylpropyl)iminocarbonyl]
Poly(N-methyldodecane lactam)
Poly(L-alanine)
Poly(beta-L-alanine)
Poly(N-methyl-L-alanine)
Poly(L-phenylalanine)
Poly(2-butyl-2-methyl-beta-alanine)
Poly(2,2-dimethyl-beta-alanine)
Poly(3,3-dimethyl-beta-alanine)
Poly(2-ethyl-2-methyl-beta-alanine)
Poly(2-methyl-2-propyl-beta-alanine)
Poly(N-isopropyl-beta-alanine)
Poly(3-methyl-beta-alanine)
Poly(N-methyl-beta-alanine)
Poly(N-phenyl-beta-alanine)
Poly(mathacryloyl-D-alanine)
Poly(M-methacryloyl-L-alanine)
Poly(L-cysteine)
Poly(L-glycine)
Poly(L-leucine)
Poly(isoleucine)
Poly(N-trifluoroacetal-L-lysine)
Poly(N-carbobenzoxy-L-lysine)
Poly(methionine)
Poly(L-tyrosine)
Poly(o-acetal-hydroxyproline)
Poly(o-acetal-L-serine)
Poly(alpha-amino-n-butyric acid)
Poly(s-carbobenzoxymethyl-L-cysteine)
Poly(3,4-dihydro-L-proline)
Poly(o-p-tolylsulfonyloxy-L-proline)
Poly(gamma-hydroxy-o-acetyl-L-alpha-aminoveleric acid)
Poly(L-valine)
Poly(L-proline)
Poly(L-proline), acid complex
Poly(L-proline), acetic acid complex
Poly(L-proline), formic acid complex
Poly(L-proline), propionic acid complex
Poly(o-acetyl-hydroxy-L-proline)

Poly(o-acetyl-L-serine)
Poly(o-benzyloxycarbonyl-L-tyrosine)
Poly(s-benzyloxycarbonyl-L-cysteine)
Poly(s-benzylthio-L-cysteine)
Poly(methylphosphinidene-trimethylene)
Polymalonate
Polysuccinate
Polyglutarate
Polyadipate
Poly(methylene)
Poly(diphenylmethylene)
Poly(di-p-tolyl-methylene)
Poly(ethylene)
Poly(chlorotrifluoroethylene)
Poly(1-butoxy-2-methyl-ethylene)
Poly(1-t-butoxy-2-methyl-ethylene)
Poly(1-ethoxy-2-methoxy-ethylene)
Poly(1-ethoxy-2-methyl-ethylene)
Poly(1-isobutoxy-2-methyl-ethylene)
Poly(1-isopropoxy-2-methyl-ethylene)
Poly(1-methoxy-2-methyl-ethylene)
Poly(1-methyl-2-propoxy-ethylene)
Poly(tetrafluoroethylene)
Poly(trifluoroethylene)
Poly(butylethylene)
Poly(t-butylethylene)
Poly(cyclohexylethylene)
Poly(2-cyclohexylethylene)
Poly[(cyclohexylmethyl)ethylene]
Poly(3-cyclohexylpropylethylene)
Poly(decylethylene)
Poly(dodecylethylene)
Poly(isobutyl ethylene)
Poly(neopentylethylene)
Poly(4,4-dimethylpentylethylene)
Poly(nonylethylene)
Poly(octylethylene)
Poly(propylethylene)
Poly(propyl-2-propylene)
Poly(tetradecylethylene)
Poly(vinylbromide)
Poly(N-vinyl carbazole)
Poly(vinyl chloride)
Poly(vinyl fluoride)
Poly(vinylidene bromide)
Poly(vinylidene chloride)
Poly(vinylidene fluoride)
Poly(vinylcyclobutane)
Poly(vinylcycloheptane)
Poly(vinylcyclohexane)
Poly(o-methoxy-vinylcyclohexane)
Poly(3-methyl-vinylcyclohexane)
Poly(4-methyl-vinylcyclohexane)
Poly(vinylcyclohexene)
Poly(vinylcyclohexylketone)
Poly(vinylcyclopentane)
Poly[3-(2-vinyl)-6-methyl pyridazinone]
Poly[3-(2-vinyl)-6-methyl-4,5-pyridazinone]
Poly(cyclopentylmethylethylene)
Poly(heptylethylene)
Poly(hexyldecylethylene)
Poly(hexylethylene)
Poly(cyclohexylethylene)
Poly(cyclopentylethylene)
Poly(cyclopropylethylene)
Poly(isopentylethylene)
Poly(isopropylethylene)
Poly(3,3-dimethylbutylethylene)
Poly(isohexylethylene)
Poly(1,1-dimethylethylene)
Poly(benzylethylene)
Poly(N-carbazoylylethylene)
Poly(ferrocenylethylene)
Poly(indazol-2-ylethylene)
Poly[dimethylamino(ethoxy)phosphinylethylene]
Poly[dimethylamino(phenoxy)phosphinylethylene]
Poly(4,4-dimethyl-oxazolonylethylene)
Poly(4,4-dimethyl-oxazolonyl-2-propylene)
Poly[(2-methyl-5-pyridyl)ethylene]
Poly[(2-methyl-6-pyridyl)ethylene]
Poly(2,4-dimethyl-1,3,5-triazinylethylene)
Poly(1-naphthylethylene)
Poly(2-naphthylethylene)
Poly(phenethylethylene)
Poly(phenethylmethylethylene)
Poly(phenylacetylene)
Poly(diphenylphosphinylethylene)
Poly(phenylvinylene)
Poly(phthalimidoethylene)
Poly(2-pyridylethylene)
Poly(4-pyridylethylene)
Poly(N-pyrrolidinylethylene)
Poly(m-tolylmethylethylene)
Poly(o-tolylmethylethylene)
Poly(p-tolylmethylethylene)
Poly(vinyltrimethylgermanium)
Poly(vinylcyclopropane)
Poly(N-vinyldiphenylamine)
Poly(1-vinylene-3-cyclopentylene)
Poly(o-hydroxy-vinylphenylketone)
Poly(3-vinyl pyrene)
Poly(2-vinylpyridine)
Poly(4-vinylpyridine)
Poly(2-vinyl-5-methylpyridine)
Poly(2-vinyl-5-ethylpyridine)
Poly(1-cyano-2-phenylvlnylene)
Poly(vinyl 3-trimethylsilylbenzoat)
Poly(vinylfuran)
Poly(vinylindole)
Poly(2-vinyltetrahydrofuran)
Poly(N-vinylphthalimide)
Poly(1-vinylimidazlo)
Poly(1-vinyl-2-methyl imidazole)
Poly(5-vinyl-2-methylpyridine)
Poly(1-vinylnaphthalene)
Poly(2-vinylnaphthalene)
Poly(5-vinyl-2-picoline)
Poly(3-vinylpyrene)
Poly(2-vinylpyridine)
Poly(4-vinylpyridine)
Poly(2-methyl-5-vinylpyridine)
Poly(N-vinyl carbazole)
Poly(1-vinyl naphthalene)
Poly(styryl pyridine)
Poly(N-vinyl succinimide)
Poly(1,3-divinyl-imidazolid-2-one)
Poly(1-ethyl-3-vinyl-imidazolid-2-one)
Poly(p-vinyl benzophenone)
Poly(vinyl N,N-diethyl-carbamate)
Poly(vinyl cymantrene)
Poly[vinyl-tris(trimethoxysiloxy)silane]
Poly(alpha-chlorovinyl triethoxysilane)
Poly(p-vinylbenzylethylcarbinol)
Poly(p-vinylbenzylmethylcarbinol)

Poly(divinylaniline)
Poly(vinylferrocene)
Poly(9-vinylanthracene)
Poly(vinylmercaptobenzimidazole)
Poly(vinylmercaptobenzoxazole)
Poly(vinylmercaptobenzothiazole)
Poly(p-vinyl benzophenone)
Poly(2-vinyl quinoline)
Poly(vinylidene cyanide)
Poly(1,2,5-trimethyl-vinylethylnyl-4-piperidinol)
Poly(2-vinyl-1,1-dichlorocyclopropane)
Poly(2-vinyl-2-methyl-4,4,6,6-tetraphenylcyclotrisiloxane)
Poly(N-vinyl-N-methylacetamide)
Poly(triethoxysilyl ethylene)
Poly(trimethoxysilyl ethylene)
Poly(1-acetoxy-1-cyanoethylene)
Poly(1,1-dichloroethylene)
Poly(1,1-dichloro-2-fluoroethylene)
Poly(1,1-dichloro-2,2-difluoroethylene)
Poly(1,2-dichloro-1,2-difluoroethylene)
Poly[(pentafluoroethyl)ethylene]
Poly(tetradecafluoropentylethylene)
Poly(hexafluoropropylene)
Poly(2,3,3,3-tetrafluoropropylene)
Poly(3,3,3-trifluoropropylene)
Poly[(heptafluoropropyl)ethylene]
Poly(2-iodoethylethylene)
Poly(9-iodononylethylene)
Poly(3-iodopropylethylene)
Poly[(2-acetoxybenzoyloxy)ethylene]
Poly(4-acetoxybenzoyloxyethylene)
Poly[(1-acetylindazol-3-ylcarbonyloxy)ethylene]
Poly(4-benzoylbutyryloxyethylene)
Poly(3-bromobenzoyloxyethylene)
Poly(4-bromobenzoyloxyethylene)
Poly[(t-butoxycarbonylamino)ethylene]
Poly(4-t-butylbenzoyloxyethylene)
Poly(4-butyryloxybenzoyloxyethylene)
Poly(2-chlorobenzoyloxyethylene)
Poly(3-chlorobenzoyloxyethylene)
Poly(4-chlorobenzoyloxyethylene)
Poly(cyclohexanoyloxyethylene)
Poly(cyclohexylacetoxyethylene)
Poly(4-cyclohexylbutyryloxyethylene)
Poly(cyclopentanoyloxyethylene)
Poly(cyclopentylacetoxyethylene)
Poly(4-ethoxybenzoyloxyethylene)
Poly(4-ethylbenzoyloxyethylene)
Poly[(2-ethyl-2,3,3-trimethylbutyryloxy)ethylene]
Poly(trifluoroacetoxyethylene)
Poly(heptafluorobutylryloxyethylene)
Poly[(undecafluorodecanoyloxy)ethylene]
Poly[(nonadecafluorodecanoyloxy)ethylene]
Poly[(undecafluorohexanoyloxy)ethylene]
Poly[(pentadecafluorooctanyloxy)ethylene]
Poly[(pentafluoropropionyloxy)ethylene]
Poly[(heptafluoroisopropoxy)ethylene]
Poly(formyloxyethylene)
Poly(isonicotinoyloxyethylene)
Poly(4-isopropylbenzoyloxyethylene)
Poly[(2-isopropyl-2,3-dimethylbutyryloxy)ethylene]
Poly[(2-methoxybenzoyloxy)ethylene]
Poly[(3-methoxybenzoyloxy)ethylene]
Poly[(4-methoxybenzoyloxy)ethylene]
Poly[(2-methylbenzoyloxy)ethylene]
Poly[(3-methylbenzoyloxy)ethylene]
Poly[(4-methylbenzoyloxy)ethylene]
Poly[(1-methylcyclohexanoyloxy)ethylene]
Poly(3,3-dimethyl-3-phenylpropionyloxyethylnene)
Poly[(3-trimethylsilylbenzoyloxy)ethylene]
Poly[(4-trimethylsilylbenzoyloxy)ethylene)
Poly[(2,2-dimethylvaleryloxy)ethylene]
Poly[(2,2,3,3-tetramethylvaleryloxy)ethylene]
Poly[(2,2,3,4-tetramethylvaleryloxy)ethylene]
Poly[(2,2,4,4-tetramethylvaleryloxy)ethylene]
Poly(nicotinoyloxyethylene)
Poly(nitratoethylene)
Poly[(3-nitrobenzoyloxy)ethylene]
Poly[(4-nitrobenzoyloxy)ethylene]
Poly[(4-phenylbenzoyloxy)ethylene]
Poly(pivaloyloxyethylene)
Poly[(4-propionyloxybenzoyloxy)ethylene]
Poly(propionyloxyethylene)
Poly[(4-p-toluoylbutyryloxy)ethylene]
Poly[(1,2-diethoxycarbonyl)ethylene]
Poly[(1,2-dimethoxycarbonyl)ethylene]
Poly[(1,2-dipropoxycarbonyl)ethylene]
Poly(2-bromotetrafluoroethyliminotetrafuoroethylene)
Poly[(biphenyl-4-yl)-ethylene]
Poly(2-chloroethoxyethylene)
Poly(hexadecyloxyethylene)
Poly(isobutoxyethylene)
Poly(1-methoxycarbonyl-1-phenylethylene)
Poly(9-acrydinylethylene)
Poly(4-methoxybenzylethylene)
Poly[(3,6-dibromocarbazoyl)ethylene]
Poly(dimethylpentylsilylethylene)
Poly(3,5-dimethylpyrozoylylethylene)
Poly(2-diferrocenyl-furyl-methylene)
Poly(ethoxyoxaloyloxymethyl ethylene)
Poly(9-ethyl-3-carbazoyl ethylene)
Poly(fluorenylethylene)
Poly(imidazoethylene)
Poly[(8-methoxycarbonyloctyl)ethylene]
Poly(1-methoxy-4-naphthyl ethylene)
Poly(2-methyl-5-pyridyl ethylene)
Poly(propoxyoxaloyloxymethyl ethylene)
Poly(1,1-diphenyl-2-vinylcyclopropane)
Poly(p-anthrylphenylethylene)
Poly[1-(N-ethyl-N-(1,4,7,10,13-pentaoxacyclopentadecyl)-carbamoyl)ethylene]
Poly(N-carbazolylcarbonyl ethylene)
Poly(morpholinocarbonyl ethylene)
Poly(piperidinocarbonyl ethylene)
Poly(N-benztriazolylethylene)
Poly[6-(N-carbazoyl)hexyl ethylene]
Poly(2,4-dimethyl-6-triazinylethylene)
Poly(diphenylthiophosphinylideneethylene)
Poly(2-methyl-5-pyridylethylene)
Poly(N-thiopyrrolidonylethylene)
Poly(N-1,2,4-triazolylethylene)
Poly(phenothiazinyl ethylene)
Poly(L-menthyloxycarbonylaminoethylene)
Poly(N-3-methyl-2-pyrrolidone ethylene)
Poly(p-vinyl-1,1-diphenyl ethylene)
Poly(S-vinyl-O-ethylthioacetal formaldehyde)
Poly(N-vinylphthalimide)
Poly[N-(4-vinylphenyl)phthalimide]
Poly[2-methyl-5-(4'-vinyl)phenyltetrazole]
Poly[5-phenyl-2-(4'-vinyl)phenyltetrazole]
Poly(N,N-methyl-vinyltoluenesulfonamide)
Polyallene
Poly(1-butene)
Poly(1-bromo-1-butene)

Poly(1-butyl-1-butene)
Poly(1-t-butyl-1-butene)
Poly(1-chloro-1-butene)
Poly(2-chloro-1,4,4-trifluoro-1-butene)
Poly(1-decyl-1-butene)
Poly(1-ethyl-butene)
Poly(1,4,4-trifluoro-1-butene)
Poly(octafluoro-1-butene)
Poly(1-heptyl-1-butene)
Poly(4-p-chlorophenyl-1-butene)
Poly(4-p-methoxyphenyl-1-butene)
Poly(4-cyclohexyl-1-butene)
Poly(4-phenyl-1-butene)
Poly(2-butene)
Poly(isoprene)
Poly(3-acetoxy isoprene)
Poly(1-isopropyl-1-butene)
Poly[3-(1-cyclohexenyl)isopropenyl acetate]
Poly(4-methoxy-1-butene)
Poly(4-methoxycarbonyl-3-methyl-1-butene)
Poly(1,2-dimethyl-butene)
Poly(1-phenyl-butene)
Poly(1-propyl-butene)
Poly[(3-methyl)-1-butene)]
Poly[(4-methyl)-1-butene)]
Poly[(4-phenyl)-1-butene)]
Poly[(4-cyclohexyl)-1-butene)]
Poly[(4-N,N-diisopropylamino)-1-butene)]
Poly[(3,3-dimethyl)-1-butene)]
Poly[(3-phenyl)-1-butene)]
Poly[(4-o-tolyl)-1-butene)]
Poly[(4-p-tolyl)-1-butene)]
Poly[(4,4,4-trifluoro)-1-butene)]
Poly[(3-trifluoromethyl)-1-butene)]
Poly[(4-trimethylsilyl)-1-butene]
Poly(1,3,3-trimethylbutene)
Poly(1,4-p-methoxyphenylbutene)
Poly(1,4-p-chlorophenylbutene)
Poly(1,4-cyclohexylbutene)
Poly(1,4-phenylbutene)
Poly(1,2-diethylbutene)
Poly(2,2-dimethylbutene)
Poly(1,3-cyclobutylene)
Poly[(1-cyano)-1,3-cyclobutylene]
Poly(N-butenyl carbazole)
Poly(1-decene)
Poly(1-docosene)
Poly(dodecamethylene)
Poly(1,2-chloro-dodecamethylene)
Poly(1-methyl-dodecamethylene)
Poly(1-dodecene)
Poly(1-nonene)
Poly(1-heptene)
Poly(6,6-dimethyl-1-heptene)
Poly(5-methyl-1-heptene)
Poly(heptamethylene)
Poly(1,2-dichloro-heptamethylene)
Poly[(5-methyl)-1-heptene]
Poly(1-hexadecene)
Poly(1-hexene)
Poly[(3-methyl)-1-hexene]
Poly[(4-methyl)-1-hexene]
Poly[(4,4-dimethyl)-1-hexene]
Poly[(4-ethyl)-1-hexene]
Poly[(5-methyl)-1-hexene]
Poly(1,2-cyclohexalene)
Poly(1,2-cyclopentylene-alt-ethylene)
Poly(1,3-cyclopentylene-alt-methylene)
Poly(isobutene)
Poly(1-octadecene)
Poly(octamethylene)
Poly[(1-methyl)octamethylene]
Poly(1-octene)
Poly(6,6-dimethyl-4,8-dioxaspiro-1-octene)
Poly(1-octadecene)
Poly(1-pentene)
Poly(cyclopentene)
Poly(1,3-dione-4-cyclopentene)
Poly(3,3-dimethoxy cyclopentene)
Poly(1-pentadecene)
Poly(5-amino-1-pentene)
Poly(5-cyclohexyl-1-pentene)
Poly[5-(N,N-dimethyl)amino-1-pentene]
Poly[5-(N,N-diisobutyl)amino-1-pentene]
Poly[5-(N,N-dipropyl)amino-1-pentene]
Poly(4,4-dimethyl-1-pentene)
Poly(3-methyl-1-pentene)
Poly(3-ethyl-1-pentene)
Poly(4-methyl-1-pentene)
Poly(5,5,5-trifluoro-1-pentene)
Poly(4-trifluoromethyl-1-pentene)
Poly(5-trimethylsilyl-1-pentene)
Poly(2-methyl-1-pentene)
Poly(5-phenyl-1-pentene)
Poly(1,2-cyclopentylene)
Poly(3-chloro-1,2-cyclopentylene)
Poly(pentamethylene)
Poly(1,2-dichloropentamethylene)
Poly(hexafluoroisobutylene)
Poly(chloroprene)
Poly(propene)
Poly(3-cyclohexylpropene)
Poly(3-cyclopentylpropene)
Poly(hexafluoropropene)
Poly(3-phenylpropane)
Poly[3-(2',5'-dimethylphenyl)propene]
Poly(3-(3',4'-dimethylphenyl)propene]
Poly[3-(3',5'-dimethylphenyl)propene]
Poly(3-silylpropene)
Poly(3-p-tolylpropene)
Poly(3-m-tolylpropene)
Poly(3-o-tolylpropene)
Poly(3-trimethylsilylpropene)
Poly(3,3,3-trifluoropropene)
Poly(3,3,3-trichloropropene)
Poly(1-chloropropene)
Poly(2-chloropropene)
Poly(2,3-dichloropropene)
Poly(3-chloro-2-chloromethylpropene)
Poly(ethyl-2-propylene)
Poly(1-nitropropylene)
Poly(2-trimethylsilylpropene)
Poly[1-(heptafluoroisopropoxy)methylpropylene]
Poly[(1-heptafluoroisopropoxy)propylene]
Poly(N-propenyl carbazole)
Poly(propylidene)
Poly(isopropenyltoluene)
Poly(1-tridecene)
Poly(1-tetradecene)
Poly(vinylcyclobutane)
Poly(vinylcycloheptane)
Poly(vinylcyclohexane)
Poly(vinylcyclopentane)
Poly(vilnylcyclopropane)

Poly(1-vinylene-3-cyclopentylene)
Poly(octamethylene)
Poly(1-methyloctamethylene)
Poly(decamethylene)
Poly(1,2-dichloro-decamethylene)
Poly(2,5-pyrazinecyclobutylene)
Poly(2,4-diphenyl-2,5-pyrazinecyclobutylene)
Poly(1-undecene)
Poly[(R)(−)-3,7-dimethyl-1-octene]
Poly[(S)(+)-5-methyl-1-heptene]
Poly[(S)(+)-4-methyl-1-hexene]
Poly[(S)(+)-4-methyl-1-hexyne]
Poly[(S)(+)-6-methyl-1-octene]
Poly[(S)(+)-3-methyl-1-pentene]
Poly[(R)-4-phenyl-1-hexene]
Poly(dimethyl 2,5-dicarboxylate-1-hexene)
Poly[(S)-5-phenyl-1-heptene]
Poly(1-ethyl-1-methyltetramethylene)
Poly(1,1-dimethyltetramethylene)
Poly(1,1-dimethyltrimethylene)
Poly(1,1,2-trimethyltrimethylene)
Poly(acryloyl chloride)
Poly(allylacrylate)
Poly(allyl chloride)
Poly(allylbenzene)
Poly(diallyl phthalate)
Poly(diallylcyanamide)
Poly(acryloyl pyrriolidone)
Poly(allylcyclohexane)
Poly(N-allylstearamide)
Poly(allyl chloroacetate)
Poly(allyl glycidyl phthalate)
Poly(allylcyclohexane)
Poly(allyltriethoxysilane)
Poly(allylurea)
Poly(allylbenzene)
Poly(acetylene)
Poly(beta-iodophenylacetylene)
Poly(diacetylene)
Poly(phenyl acetylene)
Poly(3-methyl-1-pentyne)
Poly(4-methyl-1-hexyne)
Poly(5-methyl-1-heptyne)
Poly(6-methyl-1-octyne)
Poly(3,4-dimethyl-1-pentyne)
Poly(2,3-dihydrofuran)
Poly(N,N-dibutylacrylamide)
Poly(N-docosylacrylamide)
Poly(N-dodecylacrylamide)
Poly(N-formylacrylamide)
Poly(N-hexadecylacrylamide)
Poly(N-octadecylacrylamide)
Poly(N-octylacrylamide)
Poly(N-phenylacrylamide)
Poly(N-propylacrylamide)
Poly(N-tetradecylacrylamide)
Poly(N-butylacrylamide)
Poly(N-sec-butylacrylamide)
Poly(N-t-butylacrylamide)
Poly(isodecylacrylamide)
Poly(isohexylacrylamide)
Poly(isononylacrylamide)
Poly(isooctylacrylamide)
Poly[N-(1,1-dimethyl-3-oxobutyl)acrylamide]
Poly[1-oxy-(2,2,6,6-tetramethyl-4-piperidyl)acrylamide]
Poly(N,N-dibutylacrylamide)
Poly(N,N-diethylacrylamide)
Poly(N,N-diisopropylacrylamide)
Poly(N,N-diphenylacrylamide)
Poly[N-(1,1-dimethyl-3-oxobutyl)acrylamide]
Poly[N-(1-methylbutyl)acrylamide]
Poly(N-methyl-N-phenylacrylamide)
Poly(N-phenyl-N-1-naphthylacrylamide)
Poly(N-phenyl-N-2-naphthylacrylamide)
Poly(morpholylacrylamide)
Poly(N-octadecylacrylamide)
Poly(pipridylacrylamide)
Poly(4-butoxycarbonylphenyl methacrylamide)
Poly(N-t-butylmethacrylamide)
Poly(N-benzyl methacrylamide)
Poly(N-phenyl methacrylamide)
Poly[N-(p-chlorophenyl) methacylamide]
Poly[N-(p-methoxyphenyl) methacrylamide]
Poly[N-(p-methylphenyl) methacrylamide]
Poly[N-(p-nitrophenyl) methacrylamide]
Poly[N-(p-stilbenyl) methacrylamide]
Poly[N-(4'-nitro-p-stibenyl) methacrylamide]
Poly(N-phenyl methacrylamide)
Poly(1-deoxy-D-glucitol methacrylamide)
Poly(4-carboxyphenylmethacrylamide)
Poly(4-ethoxycarbonylphenylmethacrylamide)
Poly(4-methoxycarbonylphenylmethacrylamide)
Poly(N-allyl methacrylamide)
Poly[1-(N-carbethoxyphenyl) methacrylamide]
Poly(p-ethoxycarbonyl phenylmethacrylamide)
Poly(carbethoxyphenyl methacrylamide)
Poly(N-methyl-N-alpha-methylbenzyl-acrylamide)
Poly(N-propyl-N-alpha-methylbenzyl-acrylamide)
Poly(p-acrylamidomethylamino azobenzene)
Poly(allyl acrylate)
Poly(biphenyloxyhexamethylene acrylate)
Poly(n-butylacrylate)
Poly(2-nitrobutylacrylate)
Poly(sec-butyl acrylate)
Poly(t-butyl acrylate)
Poly(p-carboxyphenyl acrylate)
Poly(glycidyl acrylate)
Poly(isobutyl acrylate)
Poly(isopropyl acrylate)
Poly(cresyl acrylate)
Poly(decylacrylate)
Poly(1,1-dihydroperfluoro-decylacrylate)
Poly(docosylacrylate)
Poly(dodecylacrylate)
Poly(hexadecylacrylate)
Poly(heptylacrylate)
Poly(octadecylacrylate)
Poly(octylacrylate)
Poly(1,1-dihydroperfluorooctylacrylate)
Poly(tetradecylacrylate)
Poly(isopropyl acrylate)
Poly(benzyl acrylate)
Poly(4-biphenylyl acrylate)
Poly(L-bornyl acrylate)
Poly(4-butoxycarbonylphenyl acrylate)
Poly(2-t-butylphenyl acrylate)
Poly(4-t-butylphenyl acrylate)
Poly[(1-chlorodifluoromethyl)tetrafuoroethyl acrylate]
Poly[3-chloro-2,2-bis(chloromethyl)propyl acrylate]
Poly(2-chlorophenyl acrylate)
Poly(4-chlorophenyl acrylate)
Poly(2,4-dichlorophenyl acrylate)
Poly(pentachlorophenyl acrylate)
Poly(4-cyanobenzyl acrylate)

Poly(2-cyanobutyl acrylate)
Poly(2-cyanoisobutyl acrylate)
Poly(4-cyanobutyl acrylate)
Poly(2-cyanoethyl acrylate)
Poly(2-cyanoheptyl acrylate)
Poly(2-cyanohexyl acrylate)
Poly(cyanomethyl acrylate)
Poly(2-cyanomethyl acrylate)
Poly(5-cyano-3-oxapentyl acrylate)
Poly(4-cyanophenyl acrylate)
Poly(2-cyanoisopropyl acrylate)
Poly(4-cyano-3-thiabutyl acrylate)
Poly(6-cyano-3-thiahexyl acrylate)
Poly(6-cyano-4-thiahexyl acrylate)
Poly(8-cyano-7-thiaoctyl acrylate)
Poly(5-cyano-3-thiapentyl acrylate)
Poly(cyclododecyl acrylate)
Poly(cyclohexyl acrylate)
Poly(2-chloroethyl acrylate)
Poly[di(chlorodifluoromethyl)fluoromethyl acrylate]
Poly(2-ethoxycarbonylphenyl acrylate)
Poly(3-ethoxycarbonylphenyl acrylate)
Poly(4-ethoxycarbonylphenyl acrylate)
Poly(2-ethoxyethyl acrylate)
Poly(3-ethoxypropyl acrylate)
Poly(ethyl acrylate)
Poly(2-bromoethyl acrylate)
Poly(2-ethylbutyl acrylate)
Poly(2-ethylhexyl acrylate)
Poly(ferrocenylethyl acrylate)
Poly(ferrocenylmethyl acrylate)
Poly(1H,1H-heptafluorobutyl acrylate)
Poly(heptafluoroisopropyl acrylate)
Poly[5-(heptafluroisopropoxy)pentyl acrylate]
Poly[11-(heptafluoroisopropoxy)undecyl acrylate]
Poly[2-(heptafluoropropoxy)ethyl acrylate]
Poly[(2-(heptafluorobutoxy)ethyl acrylate]
Poly[2-(1,1,2,2-tetrafluoroethoxy)ethyl acrylate]
Poly(1H,1H,3H-hexafluorobutyl acrylate)
Poly(2,2,2-trifluoroethyl acrylate)
Poly[2,2-difluoro-2-(2-heptafluorotetrahydrofuranyl)ethyl acrylate]
Poly(1H,1H-undecafluorohexyl acrylate)
Poly(fluoromethyl acrylate)
Poly(trifluoromethyl acrylate)
Poly(1H,1H-pentadecafluorooctyl acrylate)
Poly(5,5,6,6,7,7,7-heptafluoro-3-oxaheptyl acrylate)
Poly(1H,1H-undecafluoro-4-oxaheptyl acrylate)
Poly(1H,1H-nonafluoro-4-oxaheptyl acrylate)
Poly(7,7,8,8-tetrafluoro-3,6-dioxaoctyl acrylate)
Poly(1H,1H-tridecafluoro-4-oxaoctyl acrylate)
Poly(2,2,3,3,5,5,5-heptafluoro-4-oxapentyl acrylate)
Poly(4,4,5,5-tetrafluoro-3-oxapentyl acrylate)
Poly(5,5,5-trifluoro-3-oxapentyl acrylate)
Poly(1H,1H-nonafluoropentyl acrylate)
Poly(nonafluoroisobutyl acrylate)
Poly(1H,1H,5H-octafluoropentyl acrylate)
Poly(heptafluoro-2-propyl acrylate)
Poly[tetrafluoro-3-(heptafluoropropoxy)propyl acrylate]
Poly[(tetrafluoro-3-(pentafluoroethoxy)propyl acrylate]
Poly[tetrafluoro-3-(trifluoromethoxy)propyl acrylate]
Poly(1H,1H-pentafluoropropyl acrylate)
Poly(octafluoropentyl acrylate)
Poly(heptyl acrylate)
Poly(2-heptyl acrylate)
Poly(hexadecyl acrylate)
Poly(hexyl acrylate)
Poly(2-ethylhexyl acrylate)
Poly(isobornyl acrylate)
Poly(isobutyl acrylate)
Poly(isopropyl acrylate)
Poly(1,2:3,4-di-O-isopropylidene-alpha-D-galactopyranos-6-O-yl acrylate)
Poly(3-methoxybutyl acrylate)
Poly(2-methoxycarbonylphenyl acrylate)
Poly(3-methoxycarbonylphenyl acrylate)
Poly(4-methoxycarbonylphenyl acrylate)
Poly(2-methoxyethyl acrylate)
Poly(2-ethoxyethyl acrylate)
Poly(4-methoxyphenyl acrylate)
Poly(3-methoxypropyl acrylate)
Poly(3,5-dimethyladamantyl acrylate)
Poly(3-dimethylaminophenyl acrylate)
Poly(2-methylbutyl acrylate)
Poly(3-methylbutyl acrylate)
Poly(1,3-dimethylbutyl acrylate)
Poly(2-methyl-7-ethyl-4-undecyl acrylate)
Poly(2-methylpentyl acrylate)
Poly(menthyl acrylate)
Poly(2-naphthyl acrylate)
Poly(nonyl acrylate)
Poly(octyl acrylate)
Poly(2-octyl acrylate)
Poly(3-pentyl acrylate)
Poly(phenethyl acrylate)
Poly(phenyl acrylate)
Poly(2,4-dinitrophenyl acrylate)
Poly(2,4,5-trichlorophenyl acrylate)
Poly(2,4,6-tribromophenyl acrylate)
Poly(3,4-epoxyhexahydrobenzyl acrylate)
Poly[alpha-(o-ethyl methylphsphonoxy)-methyl acrylate]
Poly(propyl acrylate)
Poly(2,3-dibromopropyl acrylate)
Poly(tetradecyl acrylate)
Poly(3-thiabutyl acrylate)
Poly(4-thiahexyl acrylate)
Poly(5-thiahexyl acrylate
Poly(3-thispentyl acrylate)
Poly(4-thiapentyl acrylate)
Poly(m-tolyl acrylate)
Poly(o-tolyl acrylate)
Poly(p-tolyl acrylate)
Poly(2-ethoxyethyl acrylate)
Poly(3-ethoxypropyl acrylate)
Poly(cholesteryl acrylate)
Poly(2-ethyl-n-hexyl acrylate)
Poly(1-oxy-2,2,6,6-tetramethyl-4-piperidyl acrylate)
Poly(1,2,2,6,6-pentamethyl-4-piperidyl acrylate)
Poly(4-phenylazoxyphenyl acrylate)
Poly(ethyl cyanoacrylate)
Poly[4-(10,15,20-triphenyl-21H,23H-5-yl)phenyl acrylate]
Poly(1,1,5-trihydroperfluoroamyl acrylate)
Poly(tributyltin acrylate)
Poly (beta-ethoxyethyl acrylate)
Poly(3,4-epoxyhexahydrobenzyl acrylate)
Poly(alpha-chloroacrylnitrile)
Poly(alpha-fluoroacrylnitrile)
Poly(alpha-methoxy acrylnitrile)
Poly(alpha-trifluoromethyl acrylnitrile)
Poly(alpha-ethylacrylonitrile)
Poly(alpha-isopropylacrylonitrile)
Poly(alpha-propylacrylonitrile)
Poly(amyl methacrylate)
Poly[1-(3-cyanopropyl)acrylonitrile]

Poly(t-butyl methacrylate)
Poly(hexadecyl methacrylate)
Poly(methyl methacrylate)
Poly(cyanomethyl methacrylate)
Poly(adamantyl methacrylate)
Poly(3,5-dimethyladamantyl methacrylate)
Poly(benzyl methacrylate)
Poly(1-alpha-methylbenzyl methacrylate)
Poly(2-bromoethyl methacrylate)
Poly(2-t-butylaminoethyl methacrylate)
Poly(butyl methacrylate)
Poly(sec-butyl methacrylate)
Poly(tert-butyl methacrylate)
Poly(ethylbutyl methacrylate)
Poly(4-phenylbutyl-1-methacrylate)
Poly(2-phenylethyl-1-methacrylate)
Poly(cetyl methacrylate)
Poly(p-cetyloxybenzoyl methacrylate)
Poly(2-chloroethyl methacrylate)
Poly(cyanomethyl methacrylate)
Poly(2-cyanoethyl methacrylate)
Poly(4-cyanomethylphenyl methacrylate)
Poly(4-cyanophenyl methacrylate)
Poly(cyclohexyl methacrylate)
Poly(p-t-butylcyclohexyl methacrylate)
Poly(4-t-butylcyclohexyl methacrylate)
Poly(cyclobutyl methacrylate)
Poly(cyclobutylmethyl methacrylate)
Poly(cyclododecyl methacrylate)
Poly(2-cyclohexylethyl methacrylate)
Poly(cyclohexylmethyl methacrylate)
Poly(cyclopentyl methacrylate)
Poly(cyclooctyl methacrylate)
Poly(decyl methacrylate)
Poly(n-decyl methacrylate)
Poly(dodecyl methacrylate)
Poly(n-decosyl methacrylate)
Poly(diethylaminoethyl methacrylate)
Poly(dimethylaminoethyl methacrylate)
Poly(2-ethylhexyl methacrylate)
Poly(ethyl methacrylate)
Poly(acetoxyethyl methacrylate)
Poly(2-methoxyethyl methacrylate)
Poly(2-ethylsulfinylethyl methacrylate)
Poly(ferrocenylethyl methacrylate)
Poly(ferrocenylmethyl methacrylate)
Poly(N-methyl-N-phenyl-2-aminoethyl methacrylate)
Poly(2-N,N-dimethylcarbamoyloxyethyl methacrylate)
Poly(2-acetoxy methacrylate)
Poly(2-bromoethyl methacrylate)
Poly(2-chloroethyl methacrylate)
Poly(1H,1H-heptafluorobutyl methacrylate)
Poly(1H,1H,7H-dodecafluoroheptyl methacrylate)
Poly(1H,1H,9H-hexadecafluorononyl methacrylate)
Poly(1H,1H,5H-octafluoropentyl methacrylate)
Poly(1,1,1-trifluoro-2-propyl methacrylate)
Poly(trifluoroisopropyl methacrylate)
Poly(hexadecyl methacrylate)
Poly(hexyl methacrylate)
Poly(isobornyl methacrylate)
Poly(isobutyl methacrylate)
Poly(isopropyl methacrylate)
Poly(1,2:3,4-di-O-isopropylidene-alpha-D-galactopyranos-6-O-yl methacrylate)
Poly(2,3-O-isopropylidene-DL-glyceritol-1-O-yl methacrylate)
Poly(nonyl methacrylate)
Poly(methacrylic acid anhydride)
Poly(4-methoxycarbonylphenyl methacrylate)
Poly(3,5-dimethyladamantyl methacrylate)
Poly(dimethylaminoethyl methacrylate)
Poly(2-methylbutyl methacrylate)
Poly(1,3-dimethylbutyl methacrylate)
Poly(3,3-dimethylbutyl methacrylate)
Poly(3,3-dimethyl-2-butyl methacrylate)
Poly(3,5,5-trimethylhexyl methacrylate)
Poly(trimethylsilyl methacrylate)
Poly[(2-nitratoethyl) methacrylate]
Poly(octadecyl methacrylate)
Poly(octyl methacrylate)
Poly(n-octadecyl methacrylate)
Poly(3-oxabutyl methacrylate)
Poly(pentyl methacrylate)
Poly(neopentyl methacrylate)
Poly(phenethyl methacrylate)
Poly(phenyl methacrylate)
Poly(2,6-diisopropylphenyl methacrylate)
Poly(2,6-dimethylphenyl methacrylate)
Poly(2,4-dinitrophenyl methacrylate)
Poly(diphenylmethyl methacrylate)
Poly(4-t-butylphenyl methacrylate)
Poly(2-t-butylphenyl methacrylate)
Poly(o-ethylphenyl methacrylate)
Poly(p-ethylphenyl methacrylate)
Poly(m-chlorophenyl methacrylate)
Poly (m-nitrophenyl methacrylate)
Poly(propyl methacrylate)
Poly(tetradecyl methacrylate)
Poly(butyl butoxycarbonyl methacrylate)
Poly(tetradecyl methacrylate)
Poly (ethylidene dimethacrylate)
Poly(3,3,5-trimethylcyclohexyl methacrylate)
Poly(2-nitro-2-methylpropyl methacrylate)
Poly(triethylcarbinyl methacrylate)
Poly(triphenylmethyl methacrylate)
Poly(1,1-diethylpropyl methacrylate)
Poly(ethyl glycolate methacrylate)
Poly(3-methylcyclohexyl methacrylate)
Poly(4-methylcyclohexyl methacrylate)
Poly(2-methylcyclohexyl methacrylate)
Poly(1-methylcyclohexyl methacrylate)
Poly(bornyl methacrylate)
Poly(tetrahydrofurfuryl methacrylate)
Poly(vinyl methacrylate)
Poly(2-chloroethyl methacrylate)
Poly(2-diethylaminoethyl methacrylate)
Poly(2-chlorocyclohexyl methacrylate)
Poly(2-aminoethyl methacrylate)
Poly(furfuryl methacrylate)
Poly(methylmercaptyl methacrylate)
Poly(2,3-epithiopropyl methacrylate)
Poly(ferrocenylethyl methacrylate)
Poly[2-(N,N-dimethylcarbamoyloxy)ethyl methacrylate]
Poly(butyl butoxycarbonyl methacrylate)
Poly(cyclohexyl chloroacrylate)
Poly(ethyl chloroacrylate)
Poly(ethyl ethoxycarbonyl methacrylate)
Poly(ethyl ethacrylate)
Poly(ethyl fluoromethacrylate)
Poly(hexyl hexyloxycarbonyl methacrylate)
Poly(1,1-dihydropentadecafluorooctyl methacrylate)
Poly(heptafluoroisopropyl methacrylate)
Poly(heptadecafluorooctyl methacrylate)
Poly(1-hydrotetrafluoroethyl methacrylate)

Poly(1,1-dihydrotetrafluoroisopropyl methacrylate)
Poly(1-hydrohexafluorobutyl methacrylate)
Poly(1-nonafluorobutyl methacrylate)
Poly(1,3-dichloropropyl methacrylate)
Poly[2-chloro-1-(chloromethyl)ethyl methacrylate]
Poly(butylmercaptyl methacrylate)
Poly(1-phenyl-n-amyl methacrylate)
Poly[2-heptoxycarbonyl-1-heptoxycarbonylethylene) ethylene]
Poly(2-t-butylphenyl methacrylate)
Poly(4-cetyloxycarbonylphenyl methacrylate)
Poly(1-phenylethyl methacrylate)
Poly(p-methoxybenzyl methacrylate)
Poly(1-phenylallyl methacrylate)
Poly(p-cyclohexylphenyl methacrylate)
Poly(2-phenylethyl methacrylate)
Poly[1-(chlorophenyl)cyclohexyl methacrylate]
Poly(1-phenylcyclohexyl methacrylate)
Poly[2-(phenylsulfonyl)ethyl methacrylate]
Poly(m-cresyl methacrylate)
Poly(o-cresyl methacrylate)
Poly(2,3-dibromopropyl methacrylate)
Poly(1,2-diphenylethyl methacrylate)
Poly(o-chlorobenzyl methacrylate)
Poly(m-nitrobenzyl methacrylate)
Poly(2-diphenyl methacrylate)
Poly(4-diphenyl methacrylate)
Poly(alpha-naphthyl methacrylate)
Poly(beta-naphthyl methacrylate)
Poly(alpha-naphthyl carbinyl methacrylate)
Poly(2-ethoxyethyl methacrylate)
Poly(lauryl methacrylate)
Poly(pentabromophenyl methacrylate)
Poly(o-bromobenzyl methacrylate)
Poly(o-chlorodiphenylmethyl methacrylate)
Poly(pentachlorophenyl methacrylate)
Poly(2-diethylamino methacrylate)
Poly(2-fluoroethyl mathacrylate)
Poly(hexadecyl methacrylate)
Poly(2-ethylbutyl methacrylate)
Poly[4-(4-hexadecyloxy-benzoyloxy)phenyl methacrylate]
Poly(D,L-diisobornyl methacrylate)
Poly(decahydro-beta-naphthyl methacrylate)
Poly(5-p-menthyl methacrylate)
Poly(methyl butacrylate)
Poly(methyl ethacrylate)
Poly[(2-methylsulfinyl) ethylacrylate]
Poly(methylphenylacrylate)
Poly[4-(4-nonyloxy-benzoyloxy)-phenyl methacrylate]
Poly(tetrahydrofurfuryl methacrylate)
Poly[2-(triphenylmethoxy)ethyl methacrylate]
Poly(cetyl methacrylate)
Poly(2,3-epoxypropyl methacrylate)
Poly(pentachlorophenyl methacrylate)
Poly(pentafluorophenyl methacrylate)
Poly[6-(anisyloxycarbonylphenoxy)hexyl methacrylate]
Poly(ethyl-alpha-bromoacrylate)
Poly[1-(2-N-cyclohexyl-N-methyl-carbamoyloxy)ethyl methacrylate]
Poly[1-(2-N,N-diethylcarbamoyloxy)ethyl methacrylate]
Poly[(2-N,N-diethylcarbamoyloxy)-2-methylethyl methacrylate]
Poly(n-docosyl methacrylate)
Poly(2,5-dimethylpyrozolyl methacrylate)
Poly[11-(hexadecyl-dimethylammonio)-undecyl methacrylate]
Poly[2-(4-methyl-1-piperazinylcarbonyloxy)ethyl methacrylate]
Poly[(2-morpholino-carbonyloxy)ethylmethacrylate]
Poly[1-(1-nonyloxy-4-phenoxycarbonyl)phenyl methacrylate]
Poly(1,2,2,6,6-pentamethyl-4-piperidyl methacrylate)
Poly(propionyloxyethyl methacrylate)
Poly[3-(8-oxyl-7,7,9,9-tetramethyl-2,4-dioxo-1,3,8-triazaspiro(4,5)-dec-3-yl)propyl methacrylate]
Poly(n-stearyl methacrylate)
Poly[4-(1,1,3,3-tetramethylbutyl)phenyl methacrylate]
Poly(o-tolyl methacrylate)
Poly(p-tolyl methacrylate)
Poly(2,4,5-trichlorophenyl methacrylate)
Poly(n-tridecyl methacrylate)
Poly(triphenylmethyl methacrylate)
Poly(trityl methacrylate)
Poly(tetrahydro-4H-pyranyl-2-methacrylate)
Poly(tridecyl methacrylate)
Poly[2-(triphenylmethoxy)ethyl methacrylate]
Poly[2-(4-methyl-1-piperazinylcarbonyloxy)-2-methylethyl methacrylate]
Poly(p-methoxyphenyl-oxycarbonyl-p-phenoxyhexamethylene methacrylate)
Poly(diphenyl-2-pyridylmethyl methacrylate)
Poly(diphenyl-4-pyridylmethyl methacrylate)
Poly(triphenylmethyl methacrylate)
Poly(hexyleneoxyphenylenecarboxyphenyleneoxymethylene methacrylate)
Poly[4-(1,1,3,3-tetramethylbutyl)phenyl methacrylate]
Poly(glycidyl methacrylate)
Poly(2,2,6,6-tetramethyl-4-piperidinyl methacrylate)
Poly[(2,2-dimethyl-1,3-dioxolane-4-yl)methyl methacrylate]
Poly(alpha-alpha-dimethylbenzyl methacrylate)
Poly(1,1-diphenylethyl methacrylate)
Poly(2,3-epithiopropyl methacrylate)
Poly(dicyclopentadienyltitanate dimethacrylate)
Poly(diethylaminoethyl methacrylate)
Poly(5-oxo-pyrrolidinylmethyl methacrylate)
Poly(ethyl-alpha-bromoacrylate)
Poly(isopropyl-alpha-bromoacrylate)
Poly(methyl-alpha-bromoacrylate)
Poly(n-pentyl-alpha-bromoacrylate)
Poly(n-propyl-alpha-bromoacrylate)
Poly(methyl alpha-trifluoromethylacrylate)
Poly(phenyl alpha-bromoacrylate)
Poly(sec-butyl-alpha-bromoacrylate)
Poly(cyclohexyl-alpha-bromoacrylate)
Poly(methyl-alpha-bromomethacrylate)
Poly(butyl chloroacrylate)
Poly(sec-butyl chloroacrylate)
Poly(methyl chloroacrylate)
Poly(isobutyl chloroacrylate)
Poly(isopropyl chloroacrylate)
Poly(cyclohexyl chloroacrylate)
Poly(2-chloroethyl chloroacrylate)
Poly[1-methoxycarbonyl-1-methoxycarbonylmethylene) ethylene]
Poly(methyl chloroacrylate)
Poly(ethyl alpha-chloroacrylate)
Poly(methyl beta-chloroacrylate)
Poly(cyclohexyl alpha-ethoxyacrylate)
Poly(methyl fluoroacrylate)
Poly(methyl fluoromethacrylate)
Poly(methyl phenylacrylate)
Poly(propyl chloroacrylate)
Poly(methyl cyanoacrylate)

Poly(ethyl cyanoacrylate)
Poly(butylcyanoacrylate)
Poly(sec-butyl thiolacrylate)
Poly(isobutyl thiolacrylate)
Poly (ethyl thioacrylate)
Poly(methyl thioacrylate)
Poly(butyl thioacrylate)
Poly(isopropyl thiolacrylate)
Poly(propyl thiolacrylate)
Poly(phenyl thiomethacrylate)
Poly(cyclohexyl thiomethacrylate)
Poly(o-methylphenylthio methacrylate)
Poly(nonyloxy-1,4-phenyleneoxycarbonylphenyl methacrylate)
Poly(4-methyl-2-N,N-dimethylaminopentyl methacrylate)
Poly[alpha-(4-chlorobenzyl)ethyl acrylate]
Poly[alpha-(4-cyanobenzyl)ethyl acrylate]
Poly[alpha-(4-methoxybenzyl)ethyl acrylate]
Poly(alpha-acetoxy ethyl acrylate)
Poly(ethyl alpha-benzylacrylate)
Poly(methyl alpha-benzylacrylate)
Poly(methyl alpha-hexylacrylate)
Poly(ethyl alpha-fluoroacrylate)
Poly(methyl alpha-fluoroacrylate)
Poly(methyl alpha-isobutylacrylate)
Poly(methyl alpha-isopropylacrylate)
Poly(methyl alpha-methoxyacrylate)
Poly(butyl alpha-phenylacrylate)
Poly(chloroethyl alpha-phenylacrylate)
Poly(methyl alpha-phenylacrylate)
Poly(propyl alpha-phenylacrylate)
Poly(methyl alpha-propylacrylate)
Poly(methyl alpha-sec-butylacrylate)
Poly(methyl alpha-trifluoromethylacrylate)
Poly(ethyl alpha-acetoxyacrylate)
Poly(ethyl beta-ethoxyacrylate)
Poly(methacryloyl chloride)
Poly(methacryloylactone)
Poly(meethylenebutyrolactone)
Poly(acryloylpyrrolidone)
Poly[butyl N-(4-carbethoxyphenyl)itaconamate]
Poly[ethyl N-(4-carbethoxyphenyl)itaconamate]
Poly[methyl N-(4-carbethoxyphenyl)itaconamate]
Poly[propyl N-(4-carbethoxyphenyl)itaconamate]
Poly[ethyl N-(4-chlorophenyl)itaconamate]
Poly[methyl N-(4-chlorophenyl)itaconamate]
Poly[propyl N-(4-chlorophenyl)itaconamate]
Poly[butyl N-(4-methoxyphenyl)itaconamate]
Poly[ethyl N-(4-methoxyphenyl)itaconamate]
Poly[methyl N-(4-methoxyphenyl)itaconamate]
Poly[propyl N-(4-methoxyphenyl)itaconamate]
Poly[butyl N-(4-methylphenyl)itaconamate]
Poly[ethyl N-(4-methylphenyl)itaconamate]
Poly[methyl N-(4-methylphenyl)itaconamate]
Poly[propyl N-(4-methylphenyl)itaconamate]
Poly[butyl N-phenyl itaconamate]
Poly[ethyl N-phenyl itaconamate]
Poly[methyl N-phenyl itaconamate]
Poly[propyl N-phenyl itaconamate]
Poly(diamyl itaconate)
Poly(dibutyl itaconate)
Poly(diethyl itaconate)
Poly(dioctyl itaconate)
Poly(dipropyl itaconate)
Polystyrene
Poly[(p-t-butyl)-styrene]
Poly[(o-fluoro)-styrene]
Poly[(p-fluoro)-styrene]
Poly[(alpha-methyl)-styrene]
Poly[(alpha-methyl)(p-methyl)-styrene]
Poly[(m-methyl)-styrene]
Poly[(o-methyl)-styrene]
Poly[(o-methyl)(p-fluoro)-styrene]
Poly[(p-methyl)-styrene]
Poly(trimethylsilylstyrene)
Poly(beta-nitrostyrene)
Poly(4-acetylstyrene)
Poly(4-acetoxystyrene)
Poly(4-p-anisoylstyrene)
Poly(4-benzoylstyrene)
Poly[(2-benzoyloxymethyl)styrene]
Poly[(3-(4-biphenylyl)styrene]
Poly[(4-(4-biphenylyl)styrene]
Poly(5-bromo-2-butoxystyrene)
Poly(5-bromo-2-ethoxystyrene)
Poly(5-bromo-2-isopentyloxystyrene)
Poly(5-bromo-2-isopropoxystyrene)
Poly(4-bromostyrene)
Poly(2-butoxycarbonylstyrene)
Poly(4-butoxycarbonylstyrene)
Poly(4-[(2-butoxyethoxy)methyl]styrene)
Poly(2-butoxymethylstyrene)
Poly(4-butoxymethylstyrene)
Poly[4-(sec-butoxymethyl)styrene]
Poly(4-butoxystyrene)
Poly(5-t-butyl-2-methylstyrene)
Poly(4-butylstyrene)
Poly(4-sec-butylstyrene)
Poly(4-t-butylstyrene)
Poly(4-butyrylstyrene)
Poly(4-chloro-3-fluorostyrene)
Poly(4-chloro-2-methylstyrene)
Poly(4-chloro-3-methylstyrene)
Poly(2-chlorostyrene)
Poly(3-chlorostyrene)
Poly(4-chlorostyrene)
Poly(2,4-dichlorostyrene)
Poly(2,5-dichlorostyrene)
Poly(2,6-dichlorostyrene)
Poly(3,4-dichlorostyrene)
Poly(2-bromo-4-trifluoromethylstyrene)
Poly(4-cyanostyrene)
Poly(4-decylstyrene)
Poly(4-dodecylstyrene)
Poly(2-ethoxycarbonylstyrene)
Poly(4-ethoxycarbonylstyrene)
Poly[4-(2-ethoxymethyl)styrene]
Poly(2-ethoxymethylstyrene)
Poly(4-ethoxystyrene)
Poly[4-(2-diethylaminoethoxycarbonyl)styrene]
Poly(4-diethylcarbamoylstyrene)
Poly[4-(1-ethylhexyloxymethyl)styrene]
Poly(2-ethylstyrene)
Poly(3-ethylstyrene)
Poly(4-ethylstyrene)
Poly[4-(pentadecafluoroheptyl)styrene]
Poly(2-fluoro-5-methylstyrene)
Poly(4-fluorostyrene)
Poly(3-fluorostyrene)
Poly(4-fluoro-2-trifluoromethyl styrene)
Poly(p-fluoromethyl styrene)
Poly(2,5-difluorostyrene)
Poly(2,3,4,5,6,-pentafluorostyrene)
Poly(perfluorostyrene)

Poly(alpha,beta,beta-trifluorostyrene)
Poly(4-hexadecylstyrene)
Poly(4-hexanoylstyrene)
Poly(2-hexyloxycarbonylstyrene)
Poly(4-hexyloxycarbonylstyrene)
Poly(4-hexyloxymethylstyrene)
Poly(4-hexylstyrene)
Poly(4-iodostyrene)
Poly(2-isobutoxycarbonylstyrene)
Poly(4-isobutoxycarbonylstyrene)
Poly(2-isopentyloxycarbonylstyrene)
Poly(2-isopentyloxymethylstyrene)
Poly(4-isopentyloxystyrene)
Poly(2-isopropoxycarbonylstyrene)
Poly(4-isopropoxycarbonylstyrene)
Poly(2-isopropoxymethylstyrene)
Poly(4-isopropylstyrene)
Poly(4-isopropyl-alpha-methylstyrene)
Poly(4-trimethylsilyl-alpha-methylstyrene)
Poly(2,4-diisopropylstyrene)
Poly(2,5-diisopropylstyrene)
Poly(beta-methylstyrene)
Poly(2-methoxymethylstyrene)
Poly(2-methoxycarbonylstyrene)
Poly(4-methoxycarbonylstyrene)
Poly(4-methoxymethylstyrene)
Poly(4-methoxy-2-methylstyrene)
Poly(2-methoxystyrene)
Poly(4-methoxystyrene)
Poly(4-N,N-dimethylamino styrene)
Poly(2-methylaminocarbonylstyrene)
Poly(2-dimethylaminocarbonylstyrene)
Poly(4-dimethylaminocarbonylstyrene)
Poly[2-(2-dimethylaminoethoxycarbonyl)styrene]
Poly[4-(2-dimethylaminoethoxycarbonyl)styrene]
Poly(2-methylstyrene)
Poly (3-methylstyrene)
Poly(4-methylstyrene)
Poly(4-methoxystyrene)
Poly(2,4-dimethylstyrene)
Poly(2,5-dimethylstyrene)
Poly(3,4-dimethylstyrene)
Poly(3,5-dimethylstyrene)
Poly(2,4,5-trimethylstyrene)
Poly(2,4,6-trimethylstyrene)
Poly(3-[bis(trimethylsiloxy)boryl]styrene)
Poly(4-[bis(trimethylsiloxy)boryl]styrene)
Poly(4-morpholinocarbonylstyrene)
Poly[4-(3-morpholinopropionyl)styrene]
Poly(4-nonadecylstyrene)
Poly(4-nonylstyrene)
Poly(4-octadecylstyrene)
Poly(4-octanoylstyrene)
Poly[4-(octyloxymethyl)styrene]
Poly(2-octyloxystyrene)
Poly(4-octyloxystyrene)
Poly(2-pentyloxycarbonylstyrene)
Poly(2-pentyloxymethylstyrene)
Poly(2-phenethyloxymethylstyrene)
Poly(2-phenoxycarbonylstyrene)
Poly(4-phenoxystyrene)
Poly(4-phenylacetylstyrene)
Poly(2-phenylaminocarbonylstyrene)
Poly(4-phenylstyrene)
Poly(4-piperidinocarbonylstyrene)
Poly[4-(3-piperidinopropionyl)styrene]
Poly(4-propionylstyrene)
Poly(2-propoxycarbonylstyrene)
Poly(4-propoxycarbonylstyrene)
Poly(2-propoxymethylstyrene)
Poly(4-propoxymethylstyrene)
Poly(4-propoxystyrene)
Poly(4-propoxysulfonylstyrene)
Poly(4-tetradecylstyrene)
Poly(4-p-toluoylstyrene)
Poly(4-trimethylsilylstyrene)
Poly[2-(2-thio-3-methylpentyl)styrene]
Poly[9-(2-methylbutyl)-2-vinyl carbazole]
Poly[9-(2-methylbutyl)-3-vinyl carbazole]
Poly(3-sec-butyl-9-vinyl carbazole)
Poly[p-(p-tolylsulfinyl)styrene]
Poly(4-valerylstyrene)
Poly[(4-t-butyl-dimethylsilyl)oxy styrene]
Poly(4-isopropyl-2-methyl styrene)
Poly[1-(4-formylphenyl)ethylene]
Poly(alpha-methoxystyrene)
Poly(alpha-methylstyrene)
Poly(p-octylamine sulfonate styrene)
Poly(m-divinylbenzene)
Poly(p-divinylbenzene)
Polybutadiene (1,4-addition)
Polybutadiene (1,2-addition)
(2-t-butyl)-cis-1,4-poly-1,3-butadiene
(2-chloro)-trans-1,4-poly-1,3-butadiene
(2-chloro)-cis-1,4-poly-1,3-butadiene
(1-cyano)-trans-1,4-poly-1,3-butadiene
(1-methoxy)-trans-1,4-poly-1,3-butadiene
(2,3-dichloro)-trans-1,4-poly-1,3-butadiene
(2,3-dimethyl)-trans-1,4-poly-1,3-butadiene
(2,3-dimethyl)-cis-1,4-poly-1,3-butadiene
(2-methyl)-cis-1,4-poly-1,3-butadiene
(2-methyl)-trans-1,4-poly-1,3-butadiene
(2-methyl-3-chloro)-trans-1,4-poly-1,3-butadiene
(2-methylacetoxy)-trans-1,4-poly-1,3-butadiene
(2-propyl)-trans-1,4-poly-1,3-butadiene
Poly(2-decyl-1,3-butadiene)
Poly(2-heptyl-1,3-butadiene)
Poly(2-isopropyl-1,3-butadiene)
Poly(2-t-butyl-1,3-butadiene)
[1,4-(4,4'-diphenyleneglutarate)]-1,4-poly-1,3-butadiene
Poly(2-chloromethyl-1,3-butadiene)
Poly(ethyl-1-carboxylate-1,3-butadiene)
Poly(1-diethylamino-1,3-butadiene)
Poly(diethyl 1,4-carboxylate-1,3-butadiene)
Poly(1-acetoxy-1,3-butadiene)
Poly(1-ethoxy-1,3-butadiene)
Poly(2-phthalidomethyl-1,3-butadiene)
Poly(2,3-bis(diethylphosphono-1,3-butadiene)
Poly(hexafluoro-1,3-butadiene)
Poly(2-fluoro-1,3-butadiene)
Poly(1-phthalimido-1,3-butadiene)
Poly(1,4-poly-1,3-cyclohexalene)
1,12-poly-1,11-dodecadiyne
1,2-poly-1,3-pentadiene
(4-methyl)-1,2-poly-1,4-pentadiene
Poly(perfluoro-1,4-pentadiene)
Poly(1-ferrocenyl-1,3-butadiene)
Poly(perfluorobutadiene)
Poly(1-phenyl butadiene)
Poly(spiro-2,4-hepta-4,6-diene)
Poly(1,1,2-trichlorobutadiene)
Poly(1,3-pentadiene)
1,4-poly-1,3-heptadiene
(6-methyl)-trans-1,4-poly-1,3-heptadiene (5-methyl)-trans-1,4-poly-1,3-heptadiene
(3,5-dimethyl)-1,4-poly-1,3-heptadiene
(6-phenyl)-1,4-poly-1,3-heptadiene
1,4-poly-trans-1,3-hexadiene
(5-methyl)-trans-1,4-poly-1,3-hexadiene
(5-phenyl)-trans-1,4-poly-1,3-hexadiene
trans-2,5-poly-2,4-hexadiene
(2,5-dimethyl)-trans-2,5-poly-2,4-hexadiene
Poly(1,5-hexadiene)
1,4-poly-1,3-octadiene
1,4-poly-chloroprene
1,4-poly-isoprene
Poly(hexatriene)
Poly(trichlorohexatriene)
2,5-poly-2,4-hexadienoic acid, diisopropyl ester
2,5-poly-2,4-hexadienoic acid, butyl ester
2,5-poly-2,4-hexadienoic acid, ethyl ester
2,5-poly-2,4-hexadienoic acid, isoamyl ester
2,5-poly-2,4-hexadienoic acid, isobutyl ester
2,5-poly-2,4-hexadienoic acid, isopropyl ester
2,5-poly-2,4-hexadienoic acid, methyl ester
2,5-poly-2,4-hexadiyne
[1,6-di(N-carbazoyl))-2,5-poly-2,4-hexadiyne
1,9-poly-1,8-nonadiyne
1,4-poly-1,3-octadene
1,2-poly-1,3-pentadiene
(4-methyl)-1,2-poly-1,3-pentadiene
1,4-poly-1,3-pentadiene
(2-methyl)-1,4-poly-1,3-pentadiene
2,5-poly-5-phenyl-2,4-pentadienoic acid, butyl ester
2,5-poly-5-phenyl-2,4-pentadienoic acid, methyl ester
Poly(4-trans-4-ethoxy-2,4-pentadienoate)
Poly(trans-4-ethoxy-2,4-pentadienonitrile)
1,24-poly-1,11,13,23-tetracisatetrayne
Poly(3-hydroxybutyric acid)
Poly(10-hydroxycapric acid)
Poly(3-hydroxy-3-trichloromethyl-propionic acid)
Poly(2-hydroxyacetic acid)
Poly(dimethyl-2-hydroxyacetic acid)
Poly(diethyl-2-hydroxyacetic acid)
Poly(isopropyl-2-hydroxyacetic acid)
Poly(3-hydroxy-3-butenoic acid)
Poly(6-hydroxy-carproic acid)
Poly(5-hydroxy-2-(1,3-dioxane)-carprylic acid]
Poly(7-hydroxynanthic acid)
Poly[(4-methyl)-7-hydroxynanthic acid]
Poly[4-hydroxymethylene-2-(1,3-dioxane)-carprylic acid]
Poly(5-hydroxy-3-oxavaleric acid)
Poly(2,3,4-trimethoxy-5-hydroxyvaleric acid)
Poly(2-hydroxypropionic acid)
Poly(3-hydroxypropionic acid)
Poly(2,2-bischloromethyl-3-hydroxypropionic acid)
Poly(3-chloromethyl-3-hydroxypropionic acid)
Poly(2,2-butyl-3-hydroxypropionic acid)
Poly(3-dichloromethyl-3-hydroxypropionic acid)
Poly(2,2-diethyl-3-hydroxypropionic acid)
Poly(2,2-dimethyl-3-hydroxypropionic acid)
Poly(3-ethyl-3-hydroxypropionic acid)
Poly(2-ethyl-2-methyl-3-hydroxypropionic acid)
Poly(2-ethyl-2-methyl-1,1-dichloro-3-hydroxypropionic acid)
Poly(3-isopropyl-3-hydroxypropionic acid)
Poly(2-methyl-3-hydroxypropionic acid)
Poly(3-methyl-3-hydroxypropionic acid)
Poly(2-methyl-2-propyl-3-hydroxypropionic acid)
Poly(3-trichloromethyl-3-hydroxypropionic acid)
Poly(carbonoxide-alt-ethylene)
Poly(oxycarbonyl-1,5-dimethylpentamethylene)
Poly(oxycarbonylethylidene)
Poly(oxycarbonylisobutylidene)
Poly(oxycarbonylisopentylidene)
Poly(oxycarbonylpentamethylene)
Poly(oxycrabonyl-3-methylhexamethylene)
Poly(oxycarbonyl-2-methylpentamethylene)
Poly(oxycarbonyl-3-methylpentamethylene)
Poly(oxycarbonyl-4-methylpentamethylene)
Poly(oxycarbonyl-1,2,3-trimethyloxytetramethylene)
Poly(2-mercaptocarproic acid)
Poly(4-methyl-2-mercaptocarproic acid)
Poly(2-mercaptoacetic acid)
Poly(2-methyl-2-mercaptoacetic acid)
Poly(3-mercaptopropionoic acid)
Poly(2-phthalimido-3-mercaptopropionoic acid)
Poly[2-(p-toluenesulfonamido)-3-mercaptopropionic acid]
Poly(thiodipropionic anhydride)
Poly(ethyl alpha-cyanocinnamate)
Poly(cinnamonitrile)
Poly(alpha-cyanocinnamonitrile)
Poly(N-methyl citraconimide)
Poly(methyl alpha-acetyl crotonate)
Poly(ethyl alpha-carbethoxy crotonate)
Poly(ethyl alpha-chlorocrotonate)
Poly(ethyl alpha-cyanocrotonate)
Poly(methyl alpha-methoxycrotonate)
Poly(methyl alpha-methylcrotonate)
Poly(ethyl crotonate)
Poly(diethyl fumarate)
Poly(vinyl acetalacetate)
Poly(vinyl chloroacetate)
Poly(vinyl dichloroacetate)
Poly(vinyl trichloroacetate)
Poly(trifluorovinyl acetate)
Poly(propenyl acetate)
Poly(2-chloropropenyl acetate)
Poly(2-methylpropenyl acetate)
Poly(vinyl chloroacetate)
Poly(vinyl benzoate)
Poly(p-t-butylvinyl benzoate)
Poly(vinyl 4-chlorobenzoate)
Poly(vinyl 3-trimethylsilylbenzoate)
Poly(vinyl 4-trimethylsilylbenzoate)
Poly(p-acryloyloxyphenyl benzoate)
Poly(vinyl butyrate)
Poly(vinyl 1,2-phenylbutyrate)
Poly(vinyl caproate)
Poly(vinyl cinnamate)
Poly(vinyl decanoate)
Poly(vinyl dodecanoate)
Poly(vinylformate)
Poly(methyl allyl fumarate)
Poly(vinyl hexanoate)
Poly (vinyl 2-ethylhexanoate)
Poly(vinyl hexadeconoate)
Poly(vinyl isobutyrate)
Poly(vinyl isocaproate)
Poly(vinyl laurate)
Poly(vinyl myristate)
Poly(vinyl octanoate)
Poly(methyl allyl oxalate)
Poly(octyl allyl oxalate)
Poly(1-vinyl-palmitate)
Poly(t-butyl-4-vinyl perbenzoate)
Poly(vinyl propionoate)
Poly(vinyl pivalate)

Poly(vinyl stearate)
Poly(2-chloropropenyl acetate)
Poly(vinyl hendecanoate)
Poly (vinyl thioacetate)
Poly(vinylhydroquinone dibenzoate)
Poly(vinyl isocyanate)
Poly(N-vinyl-ethyl carbamate)
Poly(N-vinyl-t-butyl carbamate)
Poly(N,N-diethyl vinyl carbamate)
Poly(2-chloro-propenyl acetate)
Poly(vinylhydroquinone dibenzoate)
Poly(ethyl trans-4-ethoxy-2,4-pentadienoate)
Poly(triallyl citrate)
Poly(vinyl 12-ketostearate)
Poly(vinyl 2-ethylhexanoate)
Poly(vinylene carbonate)
Poly(divinyl adipate)
Poly(vinyl hexadecanoate)
Poly(vinyl pelargonate)
Poly(vinyl thioisocyanate)
Poly(vinyl valerate)
Poly(diallyl-beta-cyanoethylisocyanurate)
Poly(diallylcyanamide)
Poly(triallyl citrate)
Poly(triallyl cyanurate)
Poly(triallyl isocyanurate)
Poly[3-(1-cyclohexenyl)isopropenyl acetate)
Poly(isopropenyl acetate)
Poly(isopropenylisocyanate)
Poly(vinyl diethyl phosphate)
Poly(allyl acetate)
Poly(vinyl phenylisocyanate)
Poly(benzylvinylether)
Poly(butylvinylether)
Poly(2-methylbutylvinylether)
Poly(sec-butylvinylether)
Poly(1-methyl-sec-butylvinylether)
Poly(t-butylvinylether)
Poly(butylthioethylene)
Poly(1-butoxy-2-chloroethylene),cis
Poly(1-butoxy-2-chloroethylene),trans
Poly(1-chloro-2-isobutoxyethylene),trans
Poly(1-isobutoxy-2-methylethylene),trans
Poly(ethylvinyl ether)
Poly(2-chloroethylvinyl ether)
Poly(2-bromoethylvinyl ether)
Poly(vinylbutyl sulfonate)
Poly(2-methoxyethylvinyl ether)
Poly(2,2,2-trifluoroethylvinyl ether)
Poly(isobutylvinylether)
Poly(isopropylvinylether)
Poly(methylvinylether)
Poly(octylvinyl ether)
Poly(alpha-methylvinylether)
Poly(n-pentylvinylether)
Poly(propylvinylether)
Poly(1-methylpropylvinylether)
Poly(decylvinyl ether)
Poly(dodecylvinyl ether)
Poly(isobutylpropenyl ether)
Poly(cyclohexyloxyethylene)
Poly(hexadecyloxyethylene)
Poly(octadecyloxyethylene)
Poly(1-bornyloxyethylene)
Poly(1-cholesteryloxyethylene)
Poly(1,2–5,6-diisopropylidene-alpha-D-glucofuranosyl-3-oxyethylene)
Poly(1-menthyloxyethylene)
Poly(1-alpha-methylbenzyloxyethylene)
Poly[3-beta-(styryloxy)methane]
Poly(2-phenylvinyl 2-methylbutyl ether)
Poly(2-phenylvinyl 3-methylpentyl ether)
Poly[(2-ethylhexyloxy)ethylene]
Poly(ethylthioethylene)
Poly(dodecafluorobutoxy ethylene)
Poly(2,2,2-trifluoroethoxytrifluoroethylene)
Poly[1,1-bis(trifluoromethoxy)difluoroethylene]
Poly(1,1-difluoro-2-trifluoromethoxymethylene)
Poly(1,2-difluoro-1-trifluoromethoxymethylene)
Poly(hexafluoromethoxyethylene)
Poly[(heptafluoro-2-propoxy)ethylene]
Poly(hexyloxyethylene)
Poly(isobutoxyethylene)
Poly(isopropenyl methyl ether)
Poly(isopropoxyethylene)
Poly(methoxy ethylene)
Poly(2-methoxypropylene)
Poly(2,2-dimethylbutoxyethylene)
Poly(methylthioethylene)
Poly(neopentyloxyethylene)
Poly(octyloxyethylene)
Poly(pentyloxyethylene)
Poly(propoxyethylene)
Poly(1-acetyl-1-fluoroethylene)
Poly(4-bromo-3-methoxybenzoylethylene)
Poly(4-t-butylbenzoylethylene)
Poly(4-chlorobenzoylethylene)
Poly(4-ethylbenzoylethylene)
Poly(4-isopropylbenzoylethylene)
Poly(4-methoxybenzoylethylene)
Poly(3,4-dimethylbenzoylethylene)
Poly(4-propylbenzoylethylene)
Poly(p-toluoylethylene)
Poly(vinyl isobutyl sulfide)
Poly(vinyl methyl sulfide)
Poly(vinyl phenyl sulfide)
Poly(vinyl ethyl sulfoxide)
Poly(vinyl ethyl sulfide)
Poly(t-butyl vinyl ketone)
Poly(isopropenyl methyl ketone)
Poly(methyl vinyl ketone)
Poly(phenyl vinyl ketone)
Poly(2-methylbutyl vinyl ketone)
Poly(3-methylpentyl vinyl ketone)
Poly(isopropenylisocyanate)
Poly(vinyl chloromethyl ketone)
Poly(vinyl 2-chlorocyclohexyl ketone)
Poly(vinyl 4-chlorocyclohexyl ketone)
Poly(2-chloroacetaldehyde)
Poly(2,2-dichloroacetaldehyde)
Poly(2,2,2-trichloroacetaldehyde)
Poly(2-butene oxide)
Poly(2-methyl-2-butene oxide)
Poly(butadiene oxide)
Poly(butyraldehyde)
Poly(crotonaldehyde)
Poly(valeraldehyde)
Poly(1,3-cyclobutyleneoxymethylene oxide)
Poly[(2,2,4,4-tetramethyl)-1,3-cyclobutyleneoxymethylene oxide]
Poly(decamethylene oxide)
Poly(dodecamethylene oxide)
Poly(ethylene trimethylene oxide)
Poly(1,1-bischloromethyl-ethylene oxide)

Poly(bromomethyl-ethylene oxide)
Poly(t-butyl-ethylene oxide)
Poly(chloromethyl-ethylene oxide)
Poly(1,2-dichloromethyl-ethylene oxide)
Poly(1-fluoroethylene oxide)
Poly(isopropyl-ethylene oxide)
Poly(neopentyl-ethylene oxide)
Poly(tetrafluoro-ethylene oxide)
Poly(tetramethyl-ethylene oxide)
Poly(ethyleneoxymethylene oxide)
Poly(heptaldehyde)
Poly(hexamethylene oxide)
Poly(hexamethyleneoxymethylene oxide)
Poly(isobutylene oxide)
Poly(isobutyraldehyde)
Poly(isophthalaldehyde)
Poly(isopropylidene oxide)
Poly(isovaleraldehyde)
Poly(methyleneoxypentamethylene oxide)
Poly(methyleneoxytetramethylene oxide)
Poly(methyleneoxynonamethylene oxide)
Poly(methyleneoxyoctamethylene oxide)
Poly(methyleneoxytetradecamethylene oxide)
Poly(nonaldehyde)
Poly(decamethylene oxide)
Poly(nonamethylene oxide)
Poly(octamethylene oxide)
Poly(trimethylene oxide)
Poly(3,3-bisazidomethyl-trimethylene oxide)
Poly(3,3-bischloromethyl-trimethylene oxide)
Poly(3,3-bisbromomethyl-trimethylene oxide)
Poly(3,3-bisethoxymethyl-trimethylene oxide)
Poly(3,3-bisiodomethyl-trimethylene oxide)
Poly(2,2-bistrifluoromethyl-trimethylene oxide)
Poly(3,3-dimethyl-trimethylene oxide)
Poly(3,3-diethyl-trimethylene oxide)
Poly(3-ethyl-3-methyl-trimethylene oxide)
Poly(caprylaldehyde)
Poly(propionaldehyde)
Poly(3-methoxycarbonyl-propionaldehyde)
Poly(3-cyano-propionaldehyde)
Poly(propylene oxide)
Poly(2-chloromethyl-propylene oxide)
Poly[3-(1-naphthoxy)-propylene oxide]
Poly[3-(2-naphthoxy)-propylene oxide]
Poly(3-phenoxy-propylene oxide)
Poly[3-(o-chloro-phenoxy)propylene oxide]
Poly[3-(p-chloro-phenoxy)propylene oxide]
Poly[3-(dimethyl-phenoxy)propylene oxide]
Poly[3-(o-isopropyl-phenoxy)propylene oxide]
Poly[3-(p-methoxy-phenoxy)propylene oxide]
Poly[3-(m-methyl-phenoxy)propylene oxide]
Poly[3-(o-methyl-phenoxy)propylene oxide]
Poly[3-(o-phenyl-phenoxy)propylene oxide]
Poly[3-(2,4,6-trichloro-phenoxy)propylene oxide]
Poly(3,3,3-trifluoro-propylene oxide)
Poly(tetramethylene oxide)
Poly(cyclopropylidenedimethylene oxide)
Poly(styrene oxide)
Poly(allyloxymethylethylene oxide)
Poly(butoxymethylethylene oxide)
Poly(butylethylene oxide)
Poly(4-chlorobutylethylene oxide)
Poly(2-chloroethylethylene oxide)
Poly(2-cyanoethyloxymethylene oxide)
Poly(t-butylethylene oxide)
Poly(2,2-bischloromethyltrimethylene oxide)
Poly(decylethylene oxide)
Poly(ethoxymethylethylene oxide)
Poly(2-ethyl-2-chloromethyltrimethylene oxide)
Poly(ethylethylene oxide)
Poly[1-(2,2,3,3,-tetrafluorocyclobutyl)ethylene oxide)
Poly(octafluorotetramethylene oxide)
Poly[1-(heptafluoro-2-propoxymethyl)ethylene]
Poly(hexylethylene oxide)
Poly[(hexyloxymethyl)ethylene oxide]
Poly(methyleneoxy-2,2,3,3,4,4-hexafluoro-pentamethylene oxide)
Poly(methyleneoxy-2,2,3,3,4,4,5,5-octafluoro-hexamethylene oxide)
Poly(1,1-dimethylethylene oxide)
Poly(1,2-dimethylethylene oxide)
Poly(1-methyltrimethylene oxide)
Poly(2-methyltrimethylene oxide)
Poly(methyleneoxytetramethylene oxide)
Poly(octadecylethylene oxide)
Poly(trifluoropropylene oxide)
Poly(1,1-difluoroethyliminotetrafluoroethylene oxide)
Poly(trifluoromethyliminotetrafluoro oxide)
Poly(1,2-hexylene oxide)
Poly(ethylenethioethylene oxide)
Poly(difluoromethylene sulfide)
Poly(methylenethiotetramethylene sulfide)
Poly(1-ethylethylene sulfide)
Poly(ethylmethylethylene sulfide)
Poly(2-ethyl-2-methyltrimethylene sulfide)
Poly(ethylene.trimethylene.sulfide)
Poly(t-butylethylene sulfide)
Poly(isopropylethylene sulfide)
Poly(hexamethylene sulfide)
Poly(1,2-cyclohexylene sulfide)
Poly(1,3-cyclohexylene sulfide)
Poly(1,2-cyclohexylene sulfone)
Poly(1,3-cyclohexylene sulfone)
Poly(hexamethylene sulfone)
Poly(pentamethylene sulfide)
Poly(pentamethylene sulfone)
Poly(propylene sulfide)
Poly(isobutylene sulfide)
Poly(isopropylidene sulfide)
Poly(2-butene sulfide)
Poly(hexamethylenethiopentamethylene sulfide)
Poly(hexamethylenethiotetramethylene sulfide)
Poly(trimethylene sulfide)
Poly(1-methyltrimethylene sulfide)
Poly(3-methyl-6-oxo-hexamethylene sulfide)
Poly(1-methyl-3-oxo-trimethylene sulfide)
Poly(6-oxohexamethylene sulfide)
Poly(2,2-dimethyl-trimethylene sulfide)
Poly(trimethylene sulfone)
Poly(2,2-dimethyltrimethylene sulfone)
Poly(2,2-diethyltrimethylene sulfone)
Poly(2,2-dipentyltrimethylene sulfone)
Poly(tetramethylene sulfide)
Poly(tetramethylene sulfone)
Poly(ethylenethiohexamethylene sulfide)
Poly(ethylenethiotetramethylene sulfide)
Poly(pentamethylenethiotetramethylene sulfide)
Poly(tetramethylene sulfide)
Poly(decamethylene sulfide)
Poly(p-tolyl vinyl sulfoxide)
Poly(decamethylene disulfide)
Poly(heptamethylene disulfide)
Poly(hexamethylene disulfide)

Poly(nonamethylene disulfide)
Poly(octamethylene disulfide)
Poly(pentamethylene disulfide)
Poly(octamethylenedithiotetramethylene disulfide)
Poly(oxyethylenedithioethylene)
Poly(oxyethylenetetrathioethylene)
Poly(dimethylketene)
Poly(thiocarbonyl-3-methylpentamethylene)
Poly(thiocarbonyl-2-methylpentamethylene)
Poly(thiocarbonyl-1-methylethylene)
Poly(thiocarbonyl-1-p-methoxybenzenesulfonylethylene)
Poly(thiocarbonyl-1-tosylaminoethylene)
Poly(thiocarbonyl-1-p-chlorobenzenesulfoamidoethylene)
Poly(butylethylene amine)
Poly(ethylethylene amine)
Poly(isobutylethylene amine)
Poly(1,2-diethylethylene amine)
Poly(1-butyl-2-ethylethylene amine)
Poly(2-ethyl-1-pentylethylene)
Poly(N-formyl-isopropylethylene)
Poly(isopropylethylene amine)
Poly(N-formylpropylene amine)
Poly(ethylene trimethylene amine)
Poly(N-acetyl-ethylene amine)
Poly(N-benzoyl-ethylene amine)
Poly[N-(p-chloro-benzoyl)-ethylene amine]
Poly(N-butyryl-ethylene amine)
Poly[N-[4-(4-methylthiophenoxy)-butyryl]-ethylene amine]
Poly(N-cyclohexanecarbonyl-ethylene amine)
Poly(N-dodecanoyl-ethylene amine)
Poly(N-heptanoyl-ethylene amine)
Poly(N-hexanoyl-ethylene amine)
Poly(N-isobutyryl-ethylene amine)
Poly(N-isovaleryl-ethylene amine)
Poly(N-octanoyl-ethylene amine)
Poly(N-2-naphthoyl-ethylene amine)
Poly(N-p-toluoyl-ethylene amine)
Poly(N-perfluorooctaoyl-ethylene amine)
Poly(N-perfluoropropionyl-ethylene amine)
Poly(N-pivaloyl-ethylene amine)
Poly(N-valeryl-ethylene amine)
Poly(trimethylene amine)
Polysilane
Poly(di-N-hexyl-silane)
Poly(di-N-pentyl-silane)
Poly(vinyltriethoxysilane)
Poly(vinyltrimethoxysilane)
Poly(vinyltrimethylsilane)
Poly(vinyl methyldiacetoxysilane)
Poly(vinyl methyldiethoxysilane)
Poly(vinylphenyldimethylsilane)
Polysiloxane
Poly(diethylsiloxane)
Poly(dimethylsiloxane)
Poly(diphenylsiloxane)
Poly(dipropylsiloxane)
Poly(pentaphenyl-p-toluyltrsiloxane)
Poly(phenyl-p-toluylsiloxane)
Polytphthalocyaninato-siloxane)
Poly(propylmethylsiloxane)
Poly(ethylmethylsiloxane)
Poly(methyloctylsiloxane)
Poly(3,3,3-trifluoropropylmethylsiloxane)
Poly(vinylmethylsiloxane)
Polysilylene
Poly(dimethylsilylene)
Poly(diphenylsilylene)
Poly(dimethyldiallylsilane)
Poly[oxydi(pentafluorophenyl)silylenedi(oxydimethylsilylene)]
Poly[oxymethylchlorotetrafluorophenylsilylenedi(oxydimethylsilylene)]
Poly(oxymethylpentafluorophenylsilylene)
Poly(oxymethylpentafluorophenylsilyleneoxydimethylsilylene
Poly[oxymethylpentafluorophenylsilylenedi(oxydimethylsilylene)]
Poly(oxymethyl-3,3,3-trifluoropropylsilylene)
Poly(oxymethylphenylsilylene)
Poly[tri(oxydimethylsilylene)oxy(methyl)trimethylsiloxysilylene]
Poly[tri(oxydimethylsilylene)oxy(methyl)-2-phenylethylsilylene]
Poly[(4-dimethylaminophenyl)methylsilylenetrimethylene]
Poly[(4-dimethylaminophenyl)phenylsilylenetrimethylene]
Poly[(methyl)phenylsilylenetrimethylene]
Poly(1,1-dimethylsilazane)
Poly(dimethylsilylenetrimethylene)
Poly(di-p-tolylsilylenetrimethylene)
Poly(phosphazene)
Poly(bis-beta-naphthoxy-phosphazene)
Poly(bis-phenoxy-phosphazene)
Poly (di -p-methyl -bis -phenoxy-phosphazene)
Poly (di-p-chloro-bis-phenoxy-phosphazene)
Poly(di-2,4-dichloro-bis-phenoxy-phosphazene)
Poly(di-p-phenyl-bis-phenoxy-phosphazene)
Poly(di-m-trifluoromethyl-phosphazene)
Poly(di-methyl-phosphazene)
Poly(dich-oro-phosphazene)
Poly(diethoxy-phosphazene)
Poly[bis(ethylamino)phosphazene]
Poly[bis(2,2,2-trifluoroethoxy)phosphazene]
Poly[bis(3-trifluoromethylphenoxy)phosphazene]
Poly[bis(1H,1H-pentadecafluorooctyloxy)phosphazene]
Poly[bis(1H,1H-pentafluoropropoxy)phosphazene]
Poly(dimethoxy-phosphazene)
Poly[bis(phenylamino)phosphazene]
Poly[bis(piperidino)phosphazene]
Poly(diethylpropenyl phosphate)
Poly(diethylisopropenyl phosphate)
Poly[vinyl bis(chloroethyl) phosphate]
Poly(vinyldisethyl phosphate)
Poly(vinyldiethyl phosphate)
Poly(vinyldiphenyl phosphate)
Poly(alpha-bromovinyl diethyl phosphonate)
Poly(alpha-carboethoxyvinyl diethyl phosphonate)
Poly(alpha-carbomethoxyvinyl diethyl phosphonate)
Poly(isopropenyl dimethyl phosphonate)
Poly[vinyl bis(2-chloroethyl) phosphonate]
Poly(vinyl dibutyl phosphonate)
Poly(vinyl diethyl phosphonate)
Poly(vinyldiisobutyl phosphonate)
Poly(vinyl diisopropyl phosphonate)
Poly(vinyl dimethyl phosphonate)
Poly(vinyl diphenyl phosphonate)
Poly(vinyl dipropyl phosphonate)
Poly[2-(4-vinylphenyl)ethyl diethyl phosphonate)
Poly(4-vinylphenyl diethyl phosphonate)
Poly(diphenylvinyl phosphine oxide)

Any of the hydrophilic blocks of various chemistry and formula weight of the amphiphilic copolymers useful in the present invention can be used in combination with any of the hydrophobic blocks of various chemistry and formula weight, either in particles having a hydrophilic, crosslinked shell domain and a hydrophobic core domain, or in particles having a hydrophobic, crosslinked shell domain and a hydrophilic core domain, as long as the various blocks are chemically compatible in combination to form particles of the present invention and are physically conducive to forming micelles.

Amphiphilic copolymers useful in the present invention can have a molecular weight in the range of from about 2,000 to about 1,000,000, preferably from about 5,000 to about 500,000, more preferably from about 10,000 to about 200,000.

Amphiphilic copolymers useful in the present invention can have a hydrophilic/lipophilic balance in the range of from about 0.001 to about 100, preferably from about 0.01 to about 100, more preferably from about 0.1 to about 10, and still more preferably from about 0.2 to about 5.

In one preferred embodiment of the present invention, the amphiphilic copolymer comprises a diblock, triblock, or multiblock copolymer, preferably a diblock or triblock copolymer, more preferably a diblock copolymer. A particularly preferred embodiment comprises a diblock copolymer wherein one block comprises polystyrene. Another particularly preferred embodiment comprises a diblock copolymer wherein one block comprises poly((4-vinyl-N-(4'-methylstyrene)pyridinium halide)-co-(4-vinyl-N-methyl (polyethyleneglycol)pyridinium halide) -co-(4-vinylpyridine)), having the formula (II):

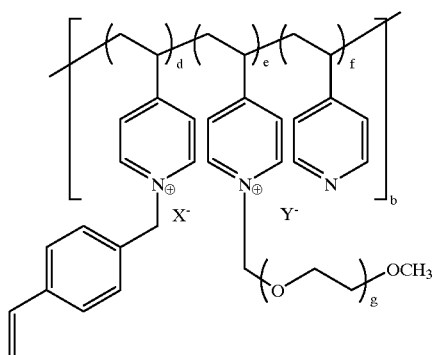

(II)

wherein b is 1; d, e, f, and g are numbers from 1 to about 5,000, preferably from about 5 to about 2,000, more preferably from about 10 to about 1,000, still more preferably from about 20 to about 100; and $X^-$ and $Y^-$ are independently pharmaceutically or agronomically acceptable anions. The monomer repeat units can be located randomly throughout the block.

Yet another particularly preferred embodiment comprises a diblock copolymer wherein one block comprises poly[styrene-b-((4-vinyl-N-(4'-methylstyrene)pyridinium halide) -co-(4-vinyl-N-methyl)polyethyleneglycol))pyridnium halide)-co-(4-vinylpyridine))] and the second block comprises polystyrene, the diblock copolymer having the formula (III):

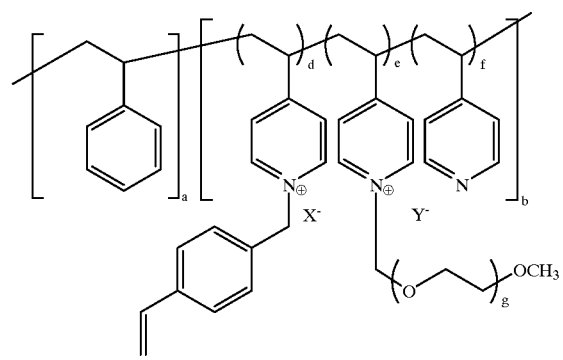

(III)

Wherein a is a number from about 10 to about 5,000, and represents the average number of repeat units of a first block of the diblock copolymer; b is 1; d, e, f, and g are numbers from 1 to about 5,000, preferably from about 5 to about 2,000, more preferably from about 10 to about 1,000, still more preferably from about 20 to about 100; and $X^-$ and $Y^-$ are independently pharmaceutically acceptable anions. The monomer units in the hydrophilic block can be randomly mixed among each other. In a further example of the diblock copolymer of formula (III), the ratio of the first block to the second block can, be in the range from about 0.5:3 to about 3:0.5, preferably from about 2:1 to about 1:2. In one particularly preferred example, the ratio of the first block to the second block is about 1:1.2. The formula weight of the first block can, for example, be from about 2,000 to about 10,000, preferably from about 3,000 to about 7,000, more preferably from about 4,000 to about 6,000. The formula weight of the second block can, for example, be from about 2,000 to about 10,000, preferably from about 3,000 to about 7,000, more preferably from about 4,000 to about 6,000. In a particularly preferred example the formula weight of the first block is about 5,000 and the formula weight of the second block is about 6,000.

In another particularly preferred example of the diblock copolymer of formula (III), the ratio of the first block to the second block is about 1.9:1. The formula weight of the first block can, for example, be from about 2,000 to about 15,000, preferably from about 3,000 to about 13,000, more preferably from about 4,000 to about 10,000. The formula weight of the second block can, for example, be from about 2,000 to about 15,000, preferably from about 3,000 to about 13,000, more preferably from about 4,000 to about 10,000. In a particularly preferred example the formula weight of the first block is about 8,000 and the formula weight of the second block is about 4,000.

In another particularly preferred embodiment, the amphiphilic copolymer can have the formula (IV):

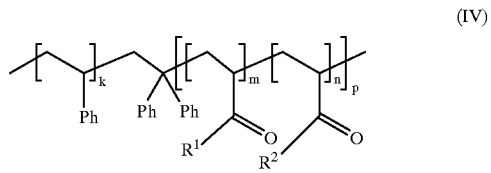

(IV)

wherein Ph is phenyl, k is a number from about 10 to about 5,000; m and n are numbers from 1 to about 10,000, preferably from about 5 to about 4,000, more preferably from about 10 to about 2,000; p is a number from about 10 to about 5,000; m and n are numbers from 1 to about 10,000, preferably from about 5 to about 4,000, more preferably from about 10 to about 2,000; and R and R are substituents independently selected from the group consisting of hydroxy, alkoxy, halogen and acyloxy. Preferably, R and R are independently hydroxy or methoxy, more preferably hydroxy. The monomer units in the hydrophilic block can be randomly mixed among each other.

In another particularly preferred embodiment, the amphiphilic copolymer can have the formula (V):

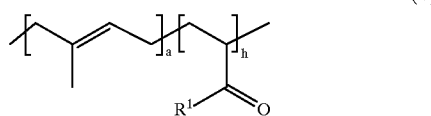

wherein a and $R^1$ are as defined above; and h is a number from 1 to about 10,000, preferably from about 5 to about 4,000, more preferably from about 10 to about 2,000

In yet another particularly perferred embodiment, the amphiphilic copolymer can have the formula (VI):

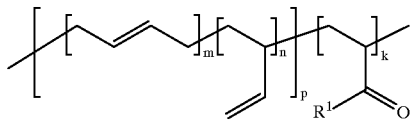

wherein k, m, n, p, and $R^1$ are as defined above.

Methods of Preparing Particles of the Present Invention

Particles of the present invention can be prepared in a variety of different ways. For example, one method of producing particles of the present invention comprises providing a plurality of amphiphilic copolymers comprising reactive functionalities, organizing the amphiphilic copolymers to produce a micellar assembly of the copolymers, and intramicellarly crosslinking the peripheral blocks of the amphiphilic copolymers of the micellar assembly to produce an amphiphilic particle comprising a crosslinked shell domain, which can be permeable, and an interior core domain.

Another method of producing particles of the present invention comprises providing a plurality of amphiphilic copolymers comprising reactive functionalities, organizing the amphiphilic copolymers to produce a micellar assembly of the copolymers containing peripheral blocks and interior blocks, and separately intramicellarly crosslinking the peripheral blocks and interior blocks of the amphiphilic copolymers of the micellar assembly to produce an amphiphilic particle comprising a crosslinked shell domain, which can be permeable, and a crosslinked interior core domain.

The organizing step in these methods of preparation of particles of the invention can be performed in a number of different ways. For example, the amphiphilic copolymers can self-assemble by placing them in an appropriate concentration in a solvent system effective in orienting the amphiphilic copolymers into micelles. The appropriate concentration of amphiphilic copolymers in this step can be from about 0.001 mg/mL to about 10 mg/mL, preferably from about 0.01 mg/mL to about 1 mg/mL, more preferably from about 0.1 mg/mL to about 0.5 mg/mL. Alternatively, active processes such as, for example, applying energy via heating, sonication, shearing, etc., can be employed to aid in orienting the amphiphilic copolymers forming the micelles.

The solvent system in these methods of preparation can predominantly comprise a hydrophilic solvent. For example the hydrophilic solvent system can be selected from the group consisting of acetaldehyde, acetic acid, acetone, aniline, benzyl alcohol, butanol, chloroethanol, cyclohexanol, di(ethylene glycol), diglyme, N,N-dimethylformamide, dimethylsulfoxide, dioxane, ethanol, ehtylene glycol, formamide, hexa(ethylene glycol), methanol, methyl acetate, 2-methyl-1-propanol, nitromethane, octanol, penta(ethylene glycol), pentanol, picoline, propanol, isopropanol, pyridine, tetrahydrofuran, tetra(ethylene glycol), tri(ethylene glycol), water, and the like, and mixtures thereof. Preferably, the hydrophilic solvent system predominantly comprises water.

The method employing a predominantly hydrophilic solvent system can be used to prepare particles wherein the crosslinked shell domain, which can be permeable, is hydrophilic.

Alternatively, the solvent system can predominantly comprise a hydrophobic solvent. For example the hydrophobic solvent system can be an alkane, an alkene, an aromatic solvent, an aliphatic solvent, a chlorinated solvent, an aldehyde, a ketone, a nitrile, an ester, an alcohol, an aniline, a sulfide, an ether, a siloxane, a silane, a heterocycle, or the like, and combinations thereof.

For example, the hydrophobic solvent can be acetaldehyde, acetone, acetonitrile, acetyl acetone, amyl acetate, n-amyl alcohol, tert-amyl alcohol, aniline, benzene, 2-butanone, butyl acetate, butyl benzene, butylcyclohexane, carbon disulfide, carbon tetrachloride, chlorobenzene, chlorobutane, chloroform, chloromethane, chloropropane, chloropentane, chlorotoluene, cumene, cycloheptane, cyclohexane, cyclohexanol, cyclohexanone, cyclohexene, cyclooctane, cyclopentane, decahydronaphthalene, decene, decnol, dichlorobenzene, dichloroethane, dichloromethane, diglyme, N,N-dimethylfomramide, 2,6-dimethyl-4-heptnaone, dimethylhexane, dimethylpentane, dimethylpropane, dimethylsulfoxide, dioxane, dodecane, ethyl acetate, ethyl benzene, ethyl ether, ethylpentane, fluorobenzene, glyme, heptane, heptanol, heptanone, hexamethyldisiloxane, hexane, hexadecane, hexanol, hexanone, isoamyl acetate, isopropyl ether, mesitylene, methylbutane, methylcyclohexane, methylheptane, methylhexane, methylpentane, 4-methyl-2-pentanone, methylpropane, N-methylpyrrolidinone, naphthalene, nitrobenzene, nitroethane, nonane, octane, octanone, pentane, picoline, propylacetate, tetrachloroethylene, tetradecane, tetrahydrofuran, tetrahydronaphthalene, tetramethylhexane, toluene, trichloroethane, trichloroethylene, trimethylpentane, undecane, xylene, or the like, and combinations thereof.

The method employing a predominantly hydrophobic solvent system can be used to prepare particles wherein the crosslinked shell domain, which can be permeable, is hydrophobic.

It should be noted that the terms "hydrophilic" and "hydrophobic" as applied to solvents herein are relative. This is to say that any particular solvent, or combination of solvents, can be "hydrophilic" or "hydrophobic" depending upon the particular amphiphilic copolymer region under consideration.

A method for producing particles comprising amphiphilic copolymers wherein the particles comprise an outermost, crosslinked shell domain, which can be permeable, a series of additional crosslinked (permeable) domains, and a domain interior to each of the crosslinked domains, comprises providing a plurality of amphiphilic copolymers comprising reactive functionalities, organizing the amphiphilic copolymers to produce a micellar assembly of said copolymers, and separately intramicellarly crosslinking the blocks of the amphiphilic copolymers of the micellar assembly comprising the crosslinked (permeable) domains via the reactive functionalities, thereby producing the particles.

The crosslinked shell domain per se and the interior core domain per se of the particles of the present invention can each independently have a net neutral, positive, or negative charge.

The methods of preparing the particles of the present invention employ amphiphilic copolymers, the blocks of which in either the crosslinked shell domain or the interior core domain can be independently or together either homogeneous or heterogeneous.

A notable advantage of the methods for forming the particles disclosed herein is that these methods permit more precise compositional and architectural control over the particle products than is possible with other types of exotic polymers.

Crosslinking

In preparing particles of the present invention, crosslinking of the shell domain, the interior core domain, or both, can be achieved using a titrimetric crosslinking reagent. Preferably, the titrimetric crosslinking reagent is a bifunctional, trifunctional, or multifunctional crosslinking reagent. Any of the titrimetric crosslinking reagents listed in Table 5 can be used in the methods of preparation of this invention. Crosslinking of the hydrophilic or hydrophobic shell domain, or of the hydrophilic or hydrophobic interior core domain, of particles of the present invention can be achieved by a variety of means including, but not limited to, condensation reactions, addition reactions, or chain polymerization reactions. Useful chain polymerization reactions include cationic chain polymerization, anionic chain polymerization, radical chain polymerization, and ring opening chain polymerization. Crosslinking can be achieved in a number of ways, including photochemically, spontaneously, by addition of a chain polymerization initiator, and by addition of titrimetric crosslinking reagents.

Titrimetric crosslinking reagents can have a variety of functional groups useful in reacting with functionalities on the amphiphilic copolymers. Such useful functional groups include nucleophilic groups, electrophilic groups, and groups which participate in pericyclic reactions.

In Table 5, $R^x$, $R^y$, and $R^z$ can independently be alkanediyl, ether, polyether, polyoxyethylene, amine, polyalkyleneimine, polyethyleneimine, arene diyl, ester, polyester, amide, polyamide, carbonate, polycarbonate, saccharide, or polysaccharide, and X is a halogen.

TABLE 5

Titrimetric Crosslinking Reagents Useful in the Present Invention

HO—$R^x$—OH
$H_2N$—$R^x$—$NH_2$
$HO_2C$—$R^y$—O—$R^x$—O—$R^z$—$CO_2H$
OCN—$R^x$—NCO
OHC—$R^x$—CHO
Cl(O)C—$R^x$—C(O)Cl

TABLE 5-continued

Titrimetric Crosslinking Reagents Useful in the Present Invention

Cl(O)CO—$R^x$—OC(O)Cl $F_3C-S(=O)(=O)-O-R^x-O-S(=O)(=O)-CF_3$ $O_2N$-C$_6$H$_4$-O-C(=O)-O-$R^x$-O-C(=O)-O-C$_6$H$_4$-$NO_2$

X—$R^x$—X

Other titrimetric crosslinking reagents can, for example, include multifunctional compounds such as polyols, polyamines, polyethyleneglycol multiarm stars, polycarboxylic acids, polycarboxylic acid halides, polyisocyanates, polymeric aromatic isocyanates, polyalkylhalides, polysulfonates, polysulfates, polyphosphonates, polyphosphates, alkyldiamines, alkanediols, ethanolamine, poly(oxyethylene), amino-substituted poly(oxyethylene), diamino-substituted poly(oxyethylene), poly(ethyleneimine), polyamino-substituted poly(oxyethylene), amino-substituted alcohols, substituted dendrimers, and substituted hyperbranched polymers.

Examples of compounds useful as radical chain polymerization initiators are listed in Table 6. One skilled in the art, of course, will after reading this disclosure recognize that many other radical chain initiators known in the art can also be used in this invention.

Table 6. Radical Chain Polymerization Initiators
ethyl peroxide
2,4-pentanedione peroxide
propyl peroxide
isopropyl peroxide
allyl tert-butyl peroxide
dimethylaminomethyl tert-butyl peroxide
tert-butyl peroxide
sec-butyl peroxide
butyl peroxide
1-hydroxybutyl-n-butyl peroxide
1-hydroxyisobutyl-isobutyl peroxide
1-hydroxyisobutyl-1-d-isobutyl-1,1-$d_2$ peroxide
dimethylaminomethyl tert-amyl peroxide
diethylaminomethyl tert-butyl peroxide
tert-amyl peroxide
apocamphane-1-formyl peroxide
2,2-bis(tert-butyl-peroxybutane) peroxide
1-hydroxy-1-hydroperoxydicyclohexyl
diisopropylaminomethyl tert-amyl peroxide
1-phenylethyl tert-butyl peroxide
tert-butyl-α-cumyl peroxide
1,1-di-(tert-butyl-peroxy)cyclohexaneethyl-3,3-di-(tert-butyl-peroxy)butyrate
1-[4-(dimethylamino)phenyl]ethyl tert-butyl peroxide
2-[4-(dimethylamino)phenyl]propyl tert-butyl peroxide
1,1-di-(tert-amylperoxy)cyclohexane 2,5-dimethyl-2,5-di(tert-butylperoxy)-hexane
2,5-dimethyl-2,5-di(tert-butylperoxy)-hexyne
n-butyl-4,4-bis(tert-butylperoxy)-valerate
1,1-bis-(tert-butylperoxy)-3,3,5-trimethylcyclohexane cumyl peroxide
bicyclo[2.2.2]octane-1-formyl peroxide
α,α-bis(tert-butylperoxy)diisopropyl benzene
2,5-dimethyl-2,5-di-(2-ethyl-hexanoylperoxy) hexane
acetyl peroxide
propionyl peroxide
2-iodopropionyl peroxide
40 perfluoropropionyl peroxide
2,2,3,3-tetrafluoropropionyl peroxide
tert-butyl permaleic acid butyryl peroxide
isobutyryl peroxide
cyclopropane formyl peroxide
diacetyl succinoyl diperoxide
succinoyl peroxide
acetyl benzoyl peroxide
5-bromo-2-thenoyl peroxide
4-bromo-2-thenoyl peroxide
50 5-chloro-2-thenoyl peroxide
α-chloropropionyl m-chlorobenzoyl peroxide
cyclobutane formyl peroxide
cyclopropane acetyl peroxide
diacetyladipoyl diperoxide
difuroyl peroxide
2,2,3,3,4,4,5,5-octafluoropentanoyl peroxide
perfluoro-2-(2-ethoxysulfinic acid)propionyl peroxide
pivaloyl peroxide
2-thenoyl peroxide
3-thenoyl peroxide
benzoyl isobutyryl peroxide
m-chlorobenzoyl isobutyryl peroxide
p-chlorobenzoyl isobutyryl peroxide
p-fluorobenzoyl isobutyryl peroxide
5-methyl-bis-2-thenoyl peroxide
p-nitrobenzoyl isobutyryl peroxide
β-allyloxpropionyl peroxide
m-chlorobenzoyl peroxide
2-mehtylbutanoyl peroxide
cyclobutane acetyl peroxide
cyclopentane formyl peroxide
hexanoyl peroxide
5-hexenoyl peroxide
4-methoxybenzoyl isobutyryl peroxide
4-methylbenzoyl isobutyryl peroxide
4-methyl-2-thenoyl peroxide
5-methyl-2-thenoyl peroxide
perfluoro-2-furnanacetyl peroxide
perfluoro-2-propoxypropionyl peroxide
perfluoro-2-n-propoxypropionyl peroxide
perfluoro-2-i-propoxypropionyl peroxide
2-azidobenzoyl peroxide
benzoyl peroxide
3-bromobenzoyl peroxide
4-bromobenzoyl peroxide
4-tert-butylbenzoyl peroxide
2-chlorobenzoyl peroxide
3-chlorobenzoyl peroxide
4-chlorobenzoyl peroxide
cyclohexane formyl peroxide
cyclopentane acetyl peroxide
diacetylsebacoyl diperoxide
2,4-dichlorobenzoyl peroxide
2,2,3,3,4,4,5,5,6,6,7,7-dodecafluoroheptanoyl peroxide
heptanoyl peroxide
6-heptenoyl peroxide
2-iodobenzoyl peroxide
2-iodobenzoyl 4-nitrobenzoyl peroxide
3-methylbenzoyl peroxide
4-methylbenzoyl peroxide
2-nitrobenzoyl peroxide
3-nitrobenzoyl peroxide
4-nitrobenzoyl peroxide
3,5-dinitrobenzoyl peroxide
perfluoroheptanoyl peroxide
benzoyl phenylacetyl peroxide
4-tert-butylbenzoyl isobutyryl peroxide
3-cyanobenzoyl benzoyl peroxide
3-methoxybenzoyl benzoyl peroxide
4-methoxybenzoyl benzoyl peroxide
4-methoxybenzoyl 3-bromobenzoyl peroxide
4-methoxybenzoyl 3,5-dinitrobenzoyl peroxide
4-methoxybenzoyl 4-nitrobenzoyl peroxide
3,5-dibromo-4-methoxybenzoyl peroxide
caprylyl peroxide
p-(chloromethyl)benzoyl peroxide
3-cyanobenzoyl peroxide
4-cyanobenzoyl peroxide
cycloheptane formyl peroxide
cyclohexane formyl peroxide
2-ethyl-4-methyl-2-pentenoyl peroxide
2-ethylhexanoyl peroxide
2-ethyl-2-hexenoyl peroxide
2-iodophenylacetyl peroxide
2-methoxybenzoyl peroxide
3-methoxybenzoyl peroxide
4-methoxybenzoyl peroxide
2-methylbenzoyl peroxide
3-methylbenzoyl peroxide
4-methlybenzoyl peroxide
endo-norbornane-2-carbonyl peroxide
exo-norborane-2-carbonyl peroxide
endo-norborene-5-carbonyl peroxide
exo-norborene-5-carbonyl peroxide
phenylacetyl peroxide
triptoyl peroxide
apocamphoyl peroxide
cis-5-tert-butylcyclohexylformyl m-chlorobenzoyl peroxide
trans-4-tert-butylcyclohexylformyl m-chlorobenzoyl peroxide
5-tert-butylthenoyl peroxide
cinnamoyl peroxide
dibenzoyl succinoyl diperoxide
nonanoyl peroxide
isononanoyl peroxide
2-nonenoyl peroxide
3-nonenoyl peroxide
2-phenylpropionyl peroxide
dibenzoyl itaconyl diperoxide
ibenzoyl α-methylsuccinoyl diperoxide
decanoyl peroxide
dioctanoyl α-bromosuccinoyl diperoxide
dioctanoyl α-chlorosuccinoyl diperoxide
4-ethyl-2-octenoyl peroxide
dioctanoyl itaconyl peroxide
dioctanoyl α-methyl succinoyl diperoxide
benzoyl 2-[trans-2-(3-nitrophenyl)vinyl]benzoyl peroxide
benzoyl 2-[trans-2-(4-nitrophenyl)vinyl]benzoyl peroxide
benzoyl 2-[trans-2-(4-nitrophenyl)vinyl]-4-nitrobenzoyl peroxide
benzoyl 2-[trans-2-(phenyl)vinyl]benzoyl peroxide
4-benzylidenebutyryl peroxide 4-tert-butylbenzoyl peroxide
cis-4-tert-butylcyclohexane formyl peroxide
trans-4-tertbutylcyclohexane formyl peroxide
trans-4-(4-chlorobenzylidene)-butyryl peroxide
trans-4-(4-fluorobenzylidene)-butyryl peroxide
1-naphthoyl peroxide
4-nitrobenzoyl-2-[trans-2-(4-nitrophenyl)vinyl]benzoyl peroxide
2-phenylisovaleryl peroxide
5-phenylpenta-2,4-dienoyl peroxide
5-phenylpentanoyl peroxide
dibenzoyl 2-bromosebacoyl diperoxide
dioctanoyl 2-bromosebacoyl diperoxide
lauroyl peroxide
trans-4-(4-methoxybenzylidene)-butyryl peroxide
trans-4-(4-methylbenzylidene)butyryl peroxide
2-phenoxybenzoyl peroxide
myristoyl peroxide
menthylphthaloyl peroxide
aliphatic polymeric diacyl peroxide
2,2'-Azobis(4-methoxy-2,4-dimethylvaleronitrile)
2,2'-Azobis(2,4-dimethyl-valeronitrile)
(1-Phenylethyl)azodiphenylmethane
2,2'-Azobisisobutyronitrile
Dimethyl 2,2'-azobis-isobutyrate
2,2'-Azobis(2-methyl-butyronitrile)
1,1'-Azobis(1-cyclo-hexanecarbonitrile)
2-(Carbamoylazo)-isobutyronitrile
2,2'-Azobis(2,4,4-trimethylpentane)
2-Phenylazo-2,4-dimethyl-4-methoxyvaleronitrile
2,2'-Azobis(2-methylpropane)
2,2'-Azobis(N,N'-dimethyleneisobutyramidine) dihydrochloride
2,2'-Azobis(2-amidinopropane) dihydrochloride
2,2'-Azobis(N,N'-dimethyleneisobutyramidine)
4,4'-Azobis(4-cyanopentoic acid)
2,2'-Azobis(2-methyl-N-(1,1-bis(hydroxymethyl)ethyl)propionamide
2,2'-Azobis(2-methyl-N-(2-hydroxyethyl)propionamide
2,2'-Azobis(isobutyramide)dihydrate Examples of compounds useful as anionic chain polymerization initiators are listed in Table 7. One skilled in the art, of course, will after reading this disclosure recognize that many other anionic chain initiators known in the art can also be used in this invention.

Table 7. Compounds Useful as Anionic Chain Polymerization Initiators alkyl lithium compounds, including butyl lithium and sec-butyl lithium
cumyl potassium
ithium diphenylmethane lithium triphenylmethane lithium alkyldiphenylmethane compounds sodium α-methylstyrene odium naphthalene potassium naphthalene Examples of compounds useful as cationic chain polymerization initiators are listed in Table 8. One skilled in the art, of course, will after reading this disclosure recognize that many other cationic chain initiators known in the art can also be used in this invention.

Table 8. Compounds Useful as Cationic Chain Polymerization Initiators

Lewis acids, including $AlCl_3$, $BCl_3$, $BF_3$, borontrifluoride etherate, $PF_5$, $SbF_5$, plus trace amount of water.

$AlCl_3$+alkyl halides hydrogen iodide and iodine initiator system perchloric acid sulfuric acid phosphoric acid fluorosulfonic acid chlorosulfonic acid methanesulfonic acid trifluoromethanesulfonic acid acetyl perchlorate perylene+electrolyte under oxidative conditions Alternatively, crosslinking of the shell domain, which can be permeable, the interior core domain, or both, can be achieved spontaneously or photochemically. It is possible to achieve spontaneous crosslinking by allowing partial hydrolysis and subsequent intramolecular and intermolecular reaction of pendant groups on the amphiphilic copolymer. For example, on an amphiphilic copolymer which contains pendant isocyanate groups, some pendant isocyanate groups can hydrolyze to pendant amine groups which subsequently react with other pendant isocyanate groups to form crosslinking urea moieties.

It is further within the scope of the present invention for the spontaneous or photochemical crosslinking to occur by a chain polymerization reaction, a pericyclic reaction, or a condensation reaction. The chain polymerization crosslinking reaction can also be initiated by a chain polymerization initiator. Chain polymerization initiators which are useful in the methods of this invention can, for example, be radical chain polymerization initiators, anionic chain polymerization initiators, cationic chain polymerization initiators, or mixtures thereof. Examples of radical chain polymerization initiators that can be used in the methods of this invention are listed in Table 6. When a polar solvent is used, it is preferable to use a polar radical chain initiator, such as 4,4'-azo-bis-cyanovaleric acid. When a non-polar solvent is used, it is preferable to use a nonpolar radical chain initiator, such as benzoyl peroxide or azo-bis-isobutyronitrile, preferably benzoyl peroxide.

Examples of anionic chain polymerization initiators that can be used in the methods of this invention are listed in Table 7, preferably, n-butyl lithium or sec-butyl lithium, more preferably n-butyl lithium.

Examples of cationic chain polymerization initiators that can be use in the methods of this invention are listed in Table 8, preferably, a lewis acid plus trace water, more preferably aluminum trichloride plus trace water.

The degree of crosslinking in the crosslinked shell domain of particles of the present invention can be in the range from about 0.1% to 100%, preferably from about 1% to about 80%, more preferably from about 10% to about 50%. The degree of crosslinking in the interior core domain of particles of the present invention can be in the range from about 0.1% to 100%, preferably from about 1% to about 80%, more preferably from about 10% to about 50%.

Particle Shape, Size, and Anatomy

The particles of the present invention can assume a variety of shapes, including spheres, cylinders, discs, needles, cones, vesicles, globules, rods, elipsoids, and any other shape that a micelle can assume under the conditions described herein, or any other shape that can be adopted through aggregation of the amphiphilic copolymers.

The size of the particles can be larger than a micron, although sizes less than a micron are preferred. When the particles take the form of spheres, they can have a mean particle diameter from about 2 nm to about 1000 nm, preferably from about 5 nm to about 200 nm, more preferably from about 10 nm to about 100 nm. When the particles take the form of cylinders or discs, they can have an aspect ratio from about 0.5 to abut 5,000, preferably from about 1 to about 500, more preferably from about 2 to about 50, still more preferably from about 2 to about 25.

The thickness of the crosslinked shell domain of particles of this invention can be in the range from about 0.2 nm to about 50 nm, preferably from about 1 nm to about nm, more preferably from about 3 nm to about 10 nm.

When the particles of the invention have the shape of a sphere, the interior core domain can have a diameter in the range from about 1 nm to about 175 nm, preferably from about 5 nm to about 100 nm, more preferably from about 15 nm to about 50 nm.

When the particles of the invention have the shape of a cylinder or a disc, the interior core domain can have an aspect ratio in the range from about 0.5 to abut 5,000, preferably from about 1 to about 500, more preferably from about 2 to about 50, still more preferably from about 2 to about 25.

The aggregation number of the amphiphilic copolymers which comprise the particles of this invention can be in the range from about 1 to about 500, preferably from about 5 10 to about 300, more preferably from about 20 to about 200.

The particles of the present invention can have an average molecular weight in the range from about 10,000 to about 5,000,000, preferably from abut 50,000 to about 2,000,000, more preferably from about 100,000 to about 1,000,000.

The crosslinked, shell domain per se and the interior core domain per se of the particles of the present invention can each independently have a net neutral, positive, or negative charge. The net positive or negative charge can be counterbalanced by one or more counterions.

The crosslinked, shell domain and the interior core domain of the particles of the present invention can each independently have a glass transition temperature in the range from about −70° C. to the decomposition temperature of the crosslinked polymer.

Pharmaceutical Compositions

The present invention provides pharmaceutical compositions, comprising particles comprising amphiphilic copolymers, having a crosslinked shell domain, which can be permeable, and an interior core domain, or a pharmaceutically acceptable salt thereof, and a pharmaceutically acceptable carrier, excipient, or diluent.

The pharmaceutical compositions can further comprise a pharmaceutically active agent. The pharmaceutically active agent can be contained within the particle. For example, the pharmaceutically active agent can be present in the particle dissolved in the crosslinked shell domain (which can be permeable), or covalently attached to a component of the crosslinked shell domain, or in the form of a fine dispersion within the crosslinked shell domain, or on the surface of the crosslinked shell domain.

Alternatively, the pharmaceutically active agent can be present in the particle dissolved in the interior core domain, or covalently attached to a component of the interior core domain, in the form of a fine dispersion within the interior core domain, or on the surface of the interior core domain, or at the interface between the crosslinked shell domain and the interior core domain.

The pharmaceutically active agent can also be present both in the crosslinked shell domain and in the interior core domain, or covalently attached to components of each domain, or in the form of a fine dispersion within each domain, or on the surface of each domain.

The pharmaceutically active agent can be introduced to the particles of the present invention in a variety of different ways. For example, in the process of forming particles of the present invention, the pharmaceutically active agent can be present in the solvent system employed to form the micelles that are the precursors to the particles of the invention. Upon formation of the particles, the pharmaceutically active agent is entrapped therein. Alternatively, pre-formed particles can be suspended in a solvent containing the active agent, and thus take up the pharmaceutically active agent from solution. In addition, the pharmaceutically active agent can be sprayed in the form of a solution or a melt onto the surface of the pre-formed particles. In another example, the pre-formed particles can be treated with a vapor containing the pharmaceutically active agent. The pharmaceutically active agent can also be vacuum infiltrated into the pre-formed particles.

The pharmaceutically active agent can be associated with or affixed to the amphiphilic copolymers either chemically or physically which comprise the particles of this invention. The association or affixing can be performed either prior to the preparation of the particles or after the preparation of the particles.

When present in particles of the present invention as described above, the pharmaceutically active agent can be released therefrom. It is fully expected that such release can be sustained, i.e., not immediate, but rather over an extended period of time, thereby making particles of the present invention containing pharmaceutically (or other active) agents useful as sustained release delivery vehicles.

Pharmaceutically Active Agents

Pharmaceutically active agents that can be used in the present invention include inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autatory of autocoid systems, alimentary and excretory systems, inhibitory of autocoids and histamine systems. The active drugs that can be delivered for the purpose of acting on these recipients include anticonvulsants, analgesics, anti-inflammatories, calcium antagonists, anesthetics, antimicrobials, antimalarials, antiparasitics, antihypertensives, antihistamines, antipyretics, alpha-andrenergic agonist, alpha-blockers, anti-tumor compounds, biocides, bactericides, bronchial dilators, beta-andrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Exemplary pharmaceutically active agents that are highly soluble in water and that can be used in conjunction with the particles of the present invention include prochlor perazine edisylate, ferrous sulfate, aminocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, and the like.

Exemplary pharmaceutically active agents that are poorly soluble in water and that can be used in conjunction with the particles of the present invention include diphenidol, meclizine hydrochloride, prochlorperazine maleate, phenoxybenzamine, thiethylperazine maleate, anisindone, diphenadione, erythrityl tetranitrate, digoxin, isoflurophate, acetazolamide, methazolamide, bendro-flumethiazide, chlorpropamide, tolazamide, chlormadinone acetate, phenaglycodol, allopurinol, aluminum aspirin, methotrexate, acetyl sulfisoxazole, erythromycin, progestins, sterogenic, progestational, corticosteroids, hydrocortisone hydrocorticosterone acetate, cotrisone acetate, triamcinolone, methyltestosterone, 17 beta-estradiol, ethinyl estradiol, ethinyl estradiol 3-methyl ether, pednisolone, 17 beta-hydroxyprogetsterone acetate, 19-norprogesterone, norgestrel, morethindrone, norethisterone, norethiederone, progesterone, norgesterone, norethynodrel, and the like.

Examples of other pharmaceutically active agents that can be used in conjunction with the particles of the present invention include aspirin, boron-containing antitumor compounds, indomethacin, naproxen, fenoprofen, sulindac, indoprofen, nitroglycerin, isosorbide dinitrate, propranolol, timolol, atenolol, alprenolol, cimetidine, clonidine, imipramine, levadopa, chloropromazine, methyldopa, dihydroxyphenylalanine, pivaloyloxyethyl ester of alpha-methyl dopa hydrochloride, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, andlapriat, famotidine, nizatidine, sucralfate, etinidine, tertatolol, minoxidil, chlordiazepoxide, chlordiazepoxide hydrochloride, diazepan, amitriptylin hydrochloride, imipramine hydrochloride, imipramine pamoate, enitabas, verapamil, losartan, and the like. Other beneficial pharmaceutically active agents known in the art that can be used in conjunction with the particles of the present invention are disclosed in *Pharmaceutical Sciences*, 14th Ed., edited by Remington, (1979) published by Mack Publishing Co., Easton Pa.; *The Drug, The Nurse, The Patient, Including Current Drug Handbook*, by Falconer, et al., (1974–1976) published by Saunders Company, Philadelphia, Pa.; *Medicinal Chemistry,* 3rd Ed., Vol. 1 and 2, by Burger, published by Wiley-Interscience, New York; *Goodman & Gilman's The Pharmacological Basis of Therapeutics,* 9th Ed., edited by Hardman, et al., (1996) published by McGraw-Hill, New York, N.Y.; and in *Physicians' Desk Reference,* 51st Ed., (1997) published by Medical Economics Co., Montvale, N.J.

Other Compositions

The present invention also provides compositions comprising particles comprising amphiphilic copolymers, having a crosslinked shell domain, which can be permeable, and an interior core domain.

In a further aspect, the present invention provides agricultural compositions, comprising particles comprising amphiphilic copolymers, having a crosslinked shell domain, which can be permeable, and an interior core domain, or an agronomically acceptable salt thereof, and an agronomically acceptable carrier, excipient, or diluent. The agricultural composition can also comprise a pesticidally active agent, as described below. The pesticidally active agent can be contained within the particles.

In still a further aspect, the present invention also provides a fat substitute composition, comprising particles comprising amphiphilic copolymers, having a crosslinked shell domain, which can be permeable, and an interior core domain, or a gastronomically acceptable salt thereof, and a gastronomically acceptable carrier, excipient, or diluent. Such fat substitute compositions can be used in methods for simulating the presence of fat in food compositions or additives by including such fat substitute compositions in food materials.

In a further aspect, the present invention provides compositions suitable for use in chromatography or electrophoresis, comprising particles comprising amphiphilic copolymers, having a crosslinked shell domain, which can be permeable, and an interior core domain, or a chromatographically or electrophoretically acceptable salt thereof, and a chromatographically or electrophoretically acceptable carrier, continuous phase, mobile phase, or diluent. Such chromatographic or electrophoretic compositions can be used in methods for separating components of mixtures. These methods can comprise introducing a mixture of components to be separated into a column containing particles of the present invention or onto a substrate coated with particles of the present invention, passing an appropriate solvent through the column or over the particle-coated substrate to separate components of the mixture, and recovering or detecting separated components of the mixture. In the case of electrophoretic separations, an electric potential is applied to the column or particle-coated substrate using conditions which are known in the art.

In a further aspect, the present invention provides compositions suitable for use in chromatography, comprising particles comprising amphiphilic copolymers, having a crosslinked shell domain, which can be permeable, and an interior core domain, or a chromatographically acceptable salt thereof, and a chromatographically acceptable carrier, continuous phase, mobile phase, or diluent.

The present invention also provides compositions suitable for use in foods, comprising particles comprising amphiphilic copolymers, having a crosslinked shell domain, which can be permeable, and an interior core domain, or a salt thereof acceptable for use in foods, and a carrier, excipient, or diluent suitable for use in foods. An example of a composition suitable for use in foods is a composition suitable for use as a fat substitute.

The present invention also provides compositions suitable for use in cosmetics, comprising particles comprising amphiphilic copolymers, having a crosslinked shell domain, which can be permeable, and an interior core domain, or a cosmetically salt thereof, and a carrier, excipient, or diluent suitable for use in cosmetics.

Methods of Use

Pharmaceutical Methods

As noted above, particles of the present invention comprising a pharmaceutically active agent can be used for sustained release delivery of such agents to treat a variety of conditions.

In one aspect, the present invention provides a method of delivering particles of the present invention, comprising administering to the mammal a composition comprising the particles. Such a method can, for example, be used in the prevention or treatment of Alzheimer's disease to scavenge proteins or protein fragments.

In another aspect, the present invention provides a method of delivering a pharmaceutically active agent to a cell, tissue, or organ, comprising contacting the cell, tissue, or organ with an effective amount of a particle comprising amphiphilic polymers having a crosslinked shell domain (which can be permeable) and an interior core domain, and the pharmaceutically active agent, the contact being for a period of time sufficient to introduce the pharmaceutically active agent to the locus of the cell, tissue, or organ. The method, for example, can comprise contacting the cell, tissue, or organ in vitro or in vivo with the effective amount of the particles.

In still another aspect, the present invention provides a method of treating a tumor in a mammal, comprising administering to the mammal an antitumor-effective amount of a pharmaceutical composition of this invention.

In yet another aspect, the present invention provides a method of reducing bile acid uptake in a mammal, comprising administering to the mammal a bile acid uptake-reducing effective amount of particles of the present invention, comprising amphiphilic copolymers, having a crosslinked shell domain, which can be permeable, and an interior core domain, the particles being administered for a period of time effective to reduce bile acid uptake in the mammal. The mammal can, for example, be a human. Preferably, the particles used in the method of reducing bile acid uptake in a mammal have a sufficient size so that they are not taken up by the gastrointestinal tract of the mammal, i.e., they do not cross the membranes comprising the gastrointestinal tract. In addition, preferred particles can comprise those wherein the outer crosslinked shell domain is hydrophilic, and the interior core domain is hydrophobic. Further preferred particles can comprise those wherein the hydrophilic shell domain is positively charged.

In another aspect, the present invention provides a method of reducing blood serum cholesterol in a mammal, comprising administering to the mammal a blood serum cholesterol-reducing effective amount of particles comprising amphiphilic copolymers, having a crosslinked shell domain, which can be permeable, and an interior core domain, the particles being administered for a period of time effective to reduce blood serum cholesterol in the mammal. The mammal can, for example, be a human. Preferably, the particles used in the method of reducing blood serum cholesterol in a mammal have a sufficient size so that they are not taken up by the gastrointestinal tract of the mammal, i.e., they do not cross the membranes comprising the gastrointestinal tract. In addition, preferred particles can comprise those wherein the outer crosslinked shell domain is hydrophilic, and the interior core domain is hydrophobic. Further preferred particles can comprise those wherein the hydrophilic shell domain is positively charged.

Dosages, Formulations, and Routes of Administration

The bile acid uptake inhibiting particles and the blood serum cholesterol lowering particles of the present invention can be administered for the prophylaxis or treatment of hyperlipidemic diseases or conditions by any means, preferably oral, that produce contact of these particles with their site of action in the body, for example in the gastrointestinal tract of a mammal, e.g., a human.

For the prophylaxis or treatment of the conditions referred to above, the particles of the present invention can be used as the particles per se. Pharmaceutically acceptable salts are particularly suitable for medical applications because of their greater aqueous solubility and physiological compatibility relative to the parent particle. Such salts must clearly have pharmaceutically acceptable anions or cations. Suitable pharmaceutically acceptable acid addition salts of the particles of the present invention when possible include those derived from inorganic acids, such as hydrochloric, hydrobromic, phosphoric, metaphosphoric, nitric, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, succinic, toluenesulfonic, tartaric, and trifluoroacetic acids. The chloride salt is particularly preferred for medical purposes. Suitable pharmaceutically acceptable base salts include ammonium salts, alkali metal salts such as sodium and potassium salts, and alkaline earth salts such as magnesium and calcium salts.

The anions of the definition of $X^-$ and $Y^-$ in the present invention are, of course, also required to be pharmaceutically acceptable and can also be selected from the above list.

The particles of the present invention can be presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the particle as a unit-dose composition, for example, a powder or tablet, which can contain from 0.05% to 95% by weight of the active particles. Other pharmacologically active substances can also be present, including other particles of the present invention. The pharmaceutical compositions of the invention can be prepared by any of the well known techniques of pharmacy, consisting essentially of admixing the components.

The particles can be administered by any conventional means available for use in conjunction with pharmaceuticals, either as individual therapeutic compounds or as a combination of therapeutic compounds.

The amount of particles required to achieve the desired biological effect will, of course, depend on a number of factors such as the specific particle chosen, the use for which it is intended, the mode of administration, and the clinical condition of the recipient.

In general, a daily dose can be in the range of from about 5 to about 5,000 mg/kg bodyweight/day, preferably from about 10 to about 2,000 mg/kg bodyweight/day, more preferably from about 20 to about 1,000 mg/kg bodyweight/day. This total daily dose can be administered to the patient in a single dose, or in proportionate multiple subdoses. Subdoses can be administered 2 to 6 times per day. Doses can be in sustained release form effective to obtain the desired results.

Orally administrable unit dose formulations, such as liquids, tablets, or capsules, can contain, for example, from about 1 to about 5,000 mg of the particles, preferably about 2 to about 2,000 mg of the particles, more preferably from about 10 to about 1,000 mg of the particles. In the case of pharmaceutically acceptable salts, the weights indicated above refer to the weight of the particle ion derived from the salt.

Oral delivery of particles of the present invention can include formulations, as are well known in the art, to provide prolonged or sustained delivery of the particles to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the particles from the dosage form. The intended effect is to extend the time period over which the active particles are delivered to the site of action (the gastrointestinal tract) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

Pharmaceutical compositions according to the present invention include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular particle which is being used. In most cases, the preferred route of administration is oral.

Pharmaceutical compositions suitable for oral administration can be presented in discrete units, such as liquids, capsules, cachets, lozenges, or tablets, each containing a predetermined amount of at least one type of particle of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active particle(s) and the carrier (which can constitute one or more accessory ingredients). In general, the compositions are prepared by uniformly and intimately admixing the active particles with a liquid or finely divided solid carrier, or both, and then, if necessary, shaping the product. For example, a tablet can be prepared by compressing or molding a powder or granules containing the particles, optionally with one or more assessory ingredients. Compressed tablets can be prepared by compressing, in a suitable machine, the particles in a free-flowing form, such as a powder or granules optionally mixed with a binder, lubricant, inert diluent and/or surface active/dispersing agent (s). Molded tablets can be made by molding, in a suitable machine, the powdered particles moistened with an inert liquid diluent.

Pharmaceutical compositions suitable for buccal (sublingual) administration include lozenges comprising particles of the present invention in a flavored base, usually sucrose, and acacia or tragacanth, and pastilles comprising particles in an inert base such as gelatin and glycerin or sucrose and acacia.

Pharmaceutical compositions suitable for parenteral administration conveniently comprise sterile aqueous preparations of particles of the present invention. These preparations are preferably administered intravenously, although administration can also be effected by means of subcutaneous, intramuscular, or intradermal injection. Such preparations can conveniently be prepared by admixing the particles with water and rendering the resulting solution sterile and isotonic with the blood. Injectable compositions according to the invention will generally contain from 0.1 to 5% w/w of a particles disclosed herein.

Pharmaceutical compositions suitable for rectal administration are preferably presented as unit-dose suppositories. These can be prepared by admixing particles of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active particle is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain particles of the present invention in an optionally buffered, aqueous solution, dissolved and/or dispersed in an adhesive, or dispersed in a polymer. A suitable concentration of the active particle is about 1% to 35%, preferably about 3% to 15%. As one particular possibility, the particle can be delivered from the patch by electrotransport or iontophoresis, for example, as described in *Pharmaceutical Research,* 3(6), 318 (1986).

In any case, the amount of particles that can be combined with carrier materials to produce a single dosage form to be administered will vary depending upon the host treated and the particular mode of administration.

The solid dosage forms for oral administration including capsules, tablets, pills, powders, and granules noted above comprise one or more types of particle of the present invention admixed with at least one inert diluent such as sucrose, lactose, or starch. Such dosage forms can also comprise, as in normal practice, additional substances other than inert diluents, e.g., lubricating agents such as magnesium stearate. In the case of capsules, tablets, and pills, the dosage forms can also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Injectable preparations, for example, sterile injectable aqueous or oleaginous suspensions can be formulated according to the known art using suitable dispersing or setting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Pharmaceutically acceptable carriers encompass all the foregoing and the like.

As those of ordinary skill in the art will recognize, the foregoing discussion is also applicable to the use of particles as described herein, wherein such particles comprise a pharmaceutically active agent intended to be delivered to a site in the body.

Treatment Regimen

The dosage regimen to prevent, give relief from, or ameliorate a disease condition, including one having hyperlipidemia as an element of the disease, e.g., atherosclerosis, or to protect against or treat further high cholesterol plasma or blood levels with the particles and/or compositions of the present invention, is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular particle or particle/pharmaceutically active agent combination employed, whether a drug delivery system is utilized, and whether the particles are administered as part of a drug combination. Thus, the dosage regimen actually employed can vary widely and therefore deviate from the preferred dosage regimen set forth above.

In any case, initial treatment of a patient suffering from a hyperlipidemic condition can begin with the dosages indicated above. Treatment should generally be continued as necessary over a period of several weeks to several months or years until the hyperlipidemic disease condition has been controlled or eliminated. Patients undergoing treatment with the particles disclosed herein can be routinely monitored by, for example, measuring serum cholesterol levels by any of the methods well known in the art, to determine the effectiveness of therapy. Continuous analysis of such data permits modification of the treatment regimen during therapy so that optimal effective amounts of particles of the present invention are administered at any time, and so that the duration of treatment can be determined as well. In this way, the treatment regimen/dosing schedule can be rationally modified over the course of therapy so that the lowest amount of particles of the present invention which exhibit satisfactory effectiveness is administered, and so that administration is continued only so long as is necessary to successfully treat the hyperlipidemic condition. These considerations are also applicable to situations in which particles of the present invention comprising pharmaceutically active agents are used to treat various disease conditions.

Agricultural Applications

The particles of the present invention can also be used to deliver pesticidally active agents (including herbicides) to plants or animals. Such methods comprise contacting plants or animals with an effective amount of particles comprising amphiphilic copolymers, having a crosslinked shell domain, which can be permeable, and an interior core domain, further comprising a pesticidally or herbicidally active agent. The contact should be for a period of time within which the pesticidally or herbicidally active agent is introduced to the plants or animals.

The pesticidal/herbicidal compositions of the present invention, including concentrates which require dilution prior to application, can comprise one or more types of particles of this invention, at least one pesticidally/herbicidally active agent, and an adjuvant in liquid or solid form. The compositions can be prepared by admixing the active agent with the particles and an adjuvant including diluents, extenders, carriers, and conditioning agents to provide compositions in the form of finely-divided particulate solids, granules, pellets, solutions, dispersions or emulsions. Alternatively, as in the case of pharmaceutical compositions, the active agent(s) can be introduced to the particles in the process of their formation. For example, the active agent can be present in the solvent system employed to form the micelles that are the precursors to the particles of the invention. Upon formation of the particles, the active agent(s) is (are) entrapped therein. Alternatively, pre-formed particles can be suspended in a solvent containing the active agent, and thus take up the active agent from solution. In addition, the pesticidally/herbicidally active agent can be sprayed in the form of a solution or a melt onto the surface of the pre-formed particles. In another example, the pre-formed particles can be treated with a vapor containing the pesticidally/herbicidally active agent. The pesticidally/herbicidally active agent can also be vacuum infiltrated into the pre-formed particles.

The pesticidally/herbicidally active agent can be covalently bound to the amphiphilic copolymers which comprise the particles of this invention. The covalent bonds can be formed either prior to the preparation of the particles or they can be formed after the preparation of the particles.

However the particles are loaded with the active agent, it is believed that the particles can be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan) and polyoxyethylene derivatives of castor oil. Preferred dispersants are methyl cellulose, polyoxyethylene/polyoxypropylene block copolymers, polyvinyl alcohol, sodium lignin sulfonates, polymeric alkyl naphthalene sulfonates, sodium naphthalene sulfonate, and the polymethylene bisnaphthalene sulfonate.

Wettable powders are water-dispersible compositions containing particles of the present invention comprising one or more active ingredients, an inert solid extender, and one or more wetting and dispersing agents. The inert solid extenders are usually of mineral origin such as the natural clays, diatomaceous earth, and synthetic minerals derived from silica and the like. Examples of such extenders include kaolinites, bentonite, attapulgite clay, and synthetic magnesium silicate. The wettable powder compositions of the present invention can contain from about 0.5 to about 60 parts, preferably from about 2.5 to about 40 parts, more preferably from about 5 to about 20 parts, of the particles of the present invention, from about 0.5 to about 60 parts, preferably from about 2.5 to about 40 parts, more preferably from about 5 to 20 parts, of pesticidally active agent, from about 0.25 to about 25 parts, preferably from about 0.5 to about 20 parts, more preferably from about 1 to 15 parts, of wetting agent, from about 0.25 to about 25 parts, preferably from about 0.5 to about 20 parts, more preferably from about 1.0 to about 15 parts, of dispersant, and from about 5 to about 95 parts, preferably from about 5 to about 50 parts, of inert solid extender, all parts being by weight of the total composition. Where required, from about 0.1 to about 2.0 parts of the solid inert extender can be replaced by a corrosion inhibitor or anti-foaming agent, or both.

Other types of formulations include dust concentrates comprising from about 0.1 to about 60% by weight of the active ingredient contained in particles of the present invention, in a suitable extender. These dusts can be diluted for application at concentrations within the range of from about 0.1–10% by weight.

Aqueous suspensions or emulsions can be prepared by stirring a nonaqueous solution of a water-insoluble pesticidally or herbicidally active agent, particles of the present invention, and an emulsification agent with water until uniform, and then homogenizing to produce a stable emulsion of very finely-divided particles. The resulting concentrated aqueous suspension is characterized by its extremely small particle size, so that when diluted and sprayed, coverage is highly uniform. Suitable concentrations of these formulations can contain from about 0.1 to about 95%, preferably from about 1 to about 75%, more preferably from about 5 to about 50% by weight of the particles of the present invention which comprise the pesticidally or herbicidally active agent.

Concentrates can be solutions of particles comprising one or more pesticidally or herbicidally active agent in water-immiscible or partially water-immiscible solvents, together with a surface active agent. Suitable solvents for the active ingredient of this invention include dimethylformamide, chlorinated solvents, dimethylsulfoxide, N-methylpyrrolidone, hydrocarbons and water-immiscible ethers, esters or ketones. However, other high strength liquid concentrates can be formulated by dissolving particles comprising the active ingredient in a solvent, and then diluting, e.g., with kerosene, to spray concentration.

The concentrated compositions contemplated herein generally contain from about 0.1 to about 95 parts, preferably from about 1 to about 75 parts, more preferably from about 5 to about 50 parts, of the particles of the present invention, from about 0.1 to about 95 parts, preferably from about 1 to about 75 parts, more preferably from about 5 to about 60 parts, of pesticidally/herbicidally active agent, from about 0.25 to about 50 parts, preferably from about 1 to about 25 parts, of surface active agent, and where required, about 5 to about 95 parts solvent, all parts being by weight based on the total weight of emulsifiable oil.

Granules are physically stable particulate compositions comprising particles of the present invention comprising active ingredient, adhering to or distributed through a basic matrix of an inert, finely-divided particulate extender. In order to aid leaching of the pesticidally/herbicidally active agent from the particles, a surface active agent such as those listed hereinbefore can be present in the composition. Natural clays, pyrophyllites, illite, and vermiculite are examples of operable classes of particulate mineral extenders. Preferred extenders are porous, absorptive, preformed particles such as preformed and screened particulate attapulgite or heat expanded, particulate vermiculite, and the finely-divided clays such as kaolin clays, hydrated attapulgite, or bentonitic clays. These extenders are sprayed or blended with the particles to form the pesticidal granules.

The granular compositions of the present invention can contain from about 0.1 to about 30 parts by weight of the particles of this invention per 100 parts by weight of clay, from about 0.1 to about 30 parts by weight of active ingredient per 100 parts by weight of clay, and 0 to about 5 parts by weight of surface active agent per 100 parts by weight of particulate clay.

The compositions of the present invention can also contain other additaments, for example, fertilizers, other pesticidally active agents, safeners, and the like, used as adjuvants or in combination with any of the above-described adjuvants. Chemicals useful in combination with the particles of this invention include, for example, triazines, ureas, carbamates, acetamides, acetanilides, uracils, acetic acid or phenol derivatives, thiolcarbamates, triazoles, benzoic acids, nitriles, biphenyl ethers, organophosphates, fumigants, herbicides, insecticides, miticides, fungicides, nematocides, and the like. Some examples of pesticidally active agents useful in combination with the particles of the present invention are shown in Table 9.

Table 9. Pesticidally Active Agents

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium
3-methyl-4-amino-6-phenyl-1,2,4-triazin-5-(4H)one
2-(4-chloro-6-ethylamino-1,3,5-sym-2-triazinylamino)-2-methylpropionitrile
3-cyclohexyl-6-dimethylamino-1-methyl-1,3,5-triazine 2,4 (1H,3H)dione
4-amino-6-(tert-butyl)-3-methylthio-as-triazin-5(4H)one
5-amino-4-chloro-2-phenyl-3(1H)-pyridazinone
5-methylamino-4-chloro-2-(, , , -trifluoro-m-tolyl)-3(2H)-pyridazinone
5-bromo-3-(sec-butyl)-6-methyluracil Ureas N-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea
N-(3-trifluoromethylphenyl)-N,N'-dimethylurea
3-(3,4-dichlorophenyl)-1-methoxy-1-methylurea
2-Chloro-N-([(4-methoxy-6-methyl-1,3,5-triazin-2-yl)amino]carbonyl)benzenesulfonamide
Methyl 2-((([(4,6-dimethyl-2 -pyrimidinyl)amino]carbonyl) amino)sulfonyl)benzoate Carbamates/Thiolcarbamates 2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate Ethyl dipropylthiolcarbamate Acetamides/Acetanilides/Anilines/Amides 2-Chloro-N,N-diallylacetamide
N,N-dimethyl-2,2-diphenylacetamide
N-[2,4-dimethyl-5-[[(trifluoromethyl)sulfonyl]amino] phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide delta.,.delta.,.delta.-Trifluoro-2,6-dinitro-N,N-dipropyl-p-toluidine
N-(1,1-dimethylpropynyl)-3,5-dichlorobenzamide Trifluoro-2,6-dinitro-N-propyl-N-(2-chloroethyl)-p-toluidine
3,5-Dinitro-4-dipropylamino-benzenesulfonamide
N-(1-ethylpropyl)-3,4-dimethyl-2,6-dinitro-benzenamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts
Potassium 4-amino-3,5,6-trichloropicolinate
2,3-Dihydro-3,3-dimethyl-2-ethoxy-5-benzofuranyl methanesulfonate Ethers 2,4-Dichlorophenyl-4-nitrophenyl ether
2-Chloro-, ,-trifluoro-p-tolyl-3-ethoxy-4-nitrodiphenyl ether
2-Chloro-1-(3-ethoxy-4-nitrophenoxy)-4-trifluoromethyl benzene Miscellaneous 2,6-Dichlorobenzonitrile
Monosodium acid methanearsonate
Disodium methanearsonate
Fertilizers useful in combination with the active ingredients include, for example, ammonium nitrate, urea, potash and superphosphate. Other useful additaments include materials in which plant organisms take root and grow such as compost, manure, humus, sand and the like.

Insecticides

Abamectin
Permethrin
Clofentezine
Dicrotophos
Sulprofos
Bifenthrin
Carbaryl
Terbufos
Dimethoate
Malathion
Pyrethrins
Diflubenzuron
Sisulfoton
Diazinon
Dimethoate
Methoxychlor
Methyl parathion
Ethyl parathion
Parathion
Sulfur
Carbofuran Azinphos-methyl
Methomyl
Chlorpyrifos
Endosulfan
Ethoprop
Mecoprop
Acephate
Mevinphos
Lindane
Rotenone
Methidathion
Other Applications In another aspect, the present invention provides a method for delivering a nucleic acid molecule to a cell, tissue, or organ, comprising contacting the cell, tissue, or organ, in vivo or in vitro, with a composition containing a particle of the present invention and the nucleic acid molecule for a period time sufficient to deliver the nucleic acid molecule to the cell, tissue, or organ. The nucleic acid molecule can, for example, be present on the surface of the particle, or within the particle. The nucleic acid molecule can be DNA or RNA, for example, an antisense oligonucleotide, a vector, or any other type of nucleic acid molecule commonly employed in genetic engineering techniques. In still another aspect, the present invention provides a method for separating components of a solvent mixture, comprising contacting the solvent mixture with particles of the present invention for a period of time sufficient for one or more of the components of the solvent mixture to associate with the particles, and separating the particles from the remaining solvent.

In a further aspect, the present invention provides a method of synthesizing a polymer, including biopolymers, for example a nucleic acid, peptide, polypeptide, or protein, comprising associating or affixing a first monomer to an active site present on the surface of a particle of the present invention, and subsequently covalently binding successive monomers to the first monomer to produce a polymer chain. The polymer can remain attached to the particle or can be cleaved from the particle by methods known in the art. In still a further aspect, the present invention provides a method of synthesizing a derivative compound, comprising associating or affixing a substrate molecule to an active site present on the surface of a particle of the present invention, and subsequently performing reactions on the substrate molecule to produce the derivative compound. The derivative compound can remain attached to the particle or it can be cleaved from the particle by methods known in the art. Such a method can be used to prepare a single derivative compound or a mixture of derivative compounds.

The following non-limiting examples illustrate various aspects of the present invention.

Analytical Measurements $^1$H NMR spectra were recorded as solutions on either a Varian Unity 300 MHz spectrometer or on a Varian Gemini 300 MHz spectrometer with the solvent proton signal as standard. $^{13}$C NMR spectra were recorded at 75.4 MHz as solutions on either a Varian Unity 300 spectrometer or on a Varian Gemini 300 spectrometer with the solvent carbon signal as standard. Cross-polarization magic-angle spinning $^{13}$C NMR spectra were obtained at room temperature on a DNP CPMAS spectrometer[35] built around a horizontal 6-in. bore Oxford superconducting solenoid operating at a proton Larmor frequency of 60 MHz, 15.1 MHz for carbons. Lyophilized samples (200–300 mg) were spun at 1859 Hz and experiments began with 1-ms matched spin-lock cross-polarization transfers from protons at 50 kHz followed by proton decoupling at 90 kHz. The sequence repetition time for all experiments was 1 second.

Size exclusion chromatography was conducted on a Hewlett Packard series 1050 HPLC with a Hewlett Packard 1047A refractive index detector and a Viscotek model 110 differential viscometer; data analysis was performed using Trisec GPC Software, version 2.70. Two 5 $\mu$m Polymer Laboratories PLgel columns (300×7.5 mm) connected in series in order of increasing pore size (500 Å, mixed bed D) were used with THF distilled from sodium as solvent.

Glass transition temperatures ($T_g$) were measured by differential scanning calorimetry on a Perkin-Elmer DSC 4 differential scanning calorimeter (DSC). Heating rates were 10 K/min. $T_g$ was taken as the midpoint of the inflection tangent.

Excitation spectra were measured using a SPEX Fluoromax Spectrofluorometer, $\lambda$=390 nm, slit openings of 1 mm, and integration time of 2 sec./nm. Data manipulation was performed using DM3000F software.

Samples for atomic force microscopy (AFM) studies were prepared by placing a 1 $\mu$l drop of about 100 $\mu$g/mL solution of particles in water on a surface of freshly-cleaved mica (New York Mica Co.) and allowing it to dry freely in air. Optimum concentration of solution was determined empirically as one resulting in incomplete monolayer coverage of mica with particles. AFM topographs were obtained in tapping mode with the aid of a Nanoscope III system (Digital Instruments, Santa Barbara, Calif.) equipped with a D-scanner and a standard Si cantilever (l=120 $\mu$m, typical spring constant in the range 34–67 N/m). The cantilever was oscillated below its resonance frequency at 293.83 kHz. The "free" oscillation amplitude was typically between 5 and 8 nm. The samples were scanned in the atmosphere of He at setpoints corresponding to ~85% of unperturbed oscillation amplitude. Typical ranges of scan sizes and rates were respectively 0.2–2 $\mu$m and 1–4 $\mu$m/s.

IR spectra were obtained on a Mattson polaris spectrometer as KBr pellets.

EXAMPLE 1

Polystyrene-b-Polyacrylic acid (PS-b-PAA) Diblock Copolymer, Dispersion, and Crosslinking with 1,2-bis(2-bromoethoxy)ethane.

Step 1. Preparation of PS-b-PAA

The diblock polystyrene-b-polyacrylic acid (PS-b-PAA) samples were prepared by anionic polymerization of styrene followed by tert-butyl acrylate in THF at −78° C. using sec-BuLi as the initiator. The poly(tert-butylacrylate) block was converted to polyacrylic acid block by treating it with p-toluenesulfonic acid in toluene. Molecular weight of polystyrene-b-poly(tert-butyl acrylate) block copolymers and their polydispersity were determined by GPC. The composition of polyacrylic acid was determined by titration. The PS-b-PAA sample that was used for the subsequent preparation of the particles consisted of 142 styrene repeat units and 120 acrylic acid repeat units.

Step 2. Formation of Diblock Copolymer Micelles

The measured amount of PS-b-PAA samples was dissolved in THF. Water or methanol was then added slowly. Micellar solutions were formed in the solvent pair of appropriate compositions, usually resulting in a bluish tint. The concentrations of the diblock copolymers were held above the critical micelle concentration (cmc), while avoiding high concentration, which has risk of intermicellar crosslinking. The exact final composition of the solvent pair was adjusted by removing THF in vacuo. The micelles formed spontaneously from diblock PS-b-PAA in THF/methanol (1:1) solution and the concentration of diblock copolymer was 2 mg/mL.

Step 3. Crosslinking Reaction

Ester bond formation was utilized to form crosslinks throughout the shell region (Scheme 1).

Scheme 1
The Crosslinking of the Carboxylic Acid Side
Chain Groups of the Polyacrylic Acid Block by Ester Bond
Formation.

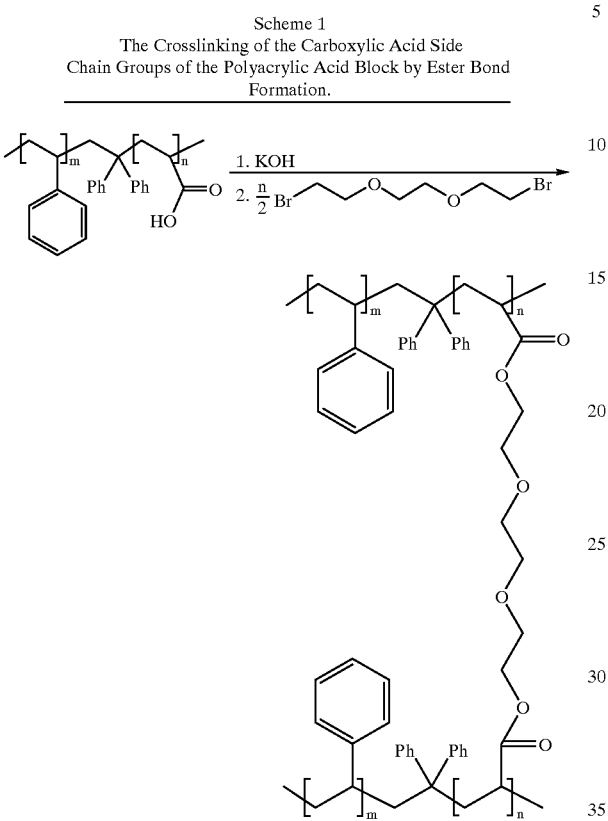

After the carboxylic acids were converted to carboxylate ions by titration with KOH in methanol, the linking reagent 1,2-bis(2-bromoethoxy)ethane was added and the reaction mixture was heated at reflux for 7 days. The mixture was then poured into water and a white colloidal solution formed immediately. The morphology of the product was examined by AFM, which showed large irregular aggregates.

EXAMPLE 2

Crosslinking of Polystyrene-b-Polyacrylic acid (PS-b-PAA) Diblock Copolymer with 1-(3-dimethylaminopropyl)-3-ethylcarbodiimide and 2,2'-(ethylenedioxy)bis(ethylamine)

The crosslinking reaction by amide links was performed for the micelles formed from diblock PS-b-PAA in THF/water (1:3) solution (Scheme 2).

Scheme 2
The Crosslinking of the Carboxylic Acid Side
Chain Groups of the Polyacrylic Acid Block by Amide Bond
Formation.

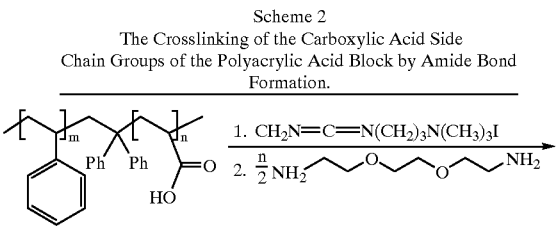

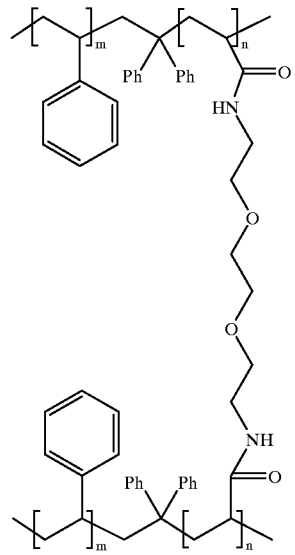

The concentration of PS-b-PAA diblock copolymer was adjusted to 0.5 mg/mL. The acrylic acid functional groups on the polyacrylic acid block were first activated by adding an exact stoichometric amount of the 1-(3-dimethylaminopropyl)-3-ethylcarbodiimide. The diamine 2,2'-(ethylenedioxy)bis-(ethylamine) (ca. 0.5 equivalent) was then added to link together two activated acid functional groups per each diamine linker. Both the activation and the crosslinking steps proceeded smoothly at room temperature. In a H NMR study, the amount of carbodiimide and diamine diminished in the activation and crosslinking reaction, respectively, indicating that crosslinking had occurred. The size and shape of the crosslinked micelles were determined by AFM. The structures were approximately spherical with diameters of ca 25 nm.

EXAMPLE 3

Polystyrene-b-polyvinylpyridine (PS-b-PVP)
Diblock Copolymer, Quaternization with p-Chloromethyl styrene, Dispersion, and Crosslinking by Radical Chain Polymerization Step 1. Preparation of PS-b-PVP The PS-b-PVP copolymer was synthesized by anionic "living" polymerization at −78° C. under argon (99.9999%) on a double manifold connected to a diffusion pump supplying a vacuum of $10^{-7}$ mm Hg. Previously purified styrene (stirred over $CaH_2$, followed by distillation and storage in the freezer) was cannulated into a schlenk flask, dibutyl magnesium was added, and then a vacuum transfer was performed. To about 300 mL of freshly distilled THF was added about 25 g of purified styrene. The polymerization was initiated by addition of 2.6 mL of sec-BuLi via syringe. After 25 minutes, a small sample of the reaction mixture was cannulated into degassed MeOH, for analysis of the PS block. To the living anion was added about 2.5 mL of DPE (purified by addition of sec-BuLi, cherry red color formation was followed by distillation at 55–60° C. under reduced pressure). The second block was then formed by addition of about 15 mL of previously purified 4-vinyl pyridine (initially dried over $CaH_2$ for 24 h and then distilled and stored in a Schlenk flask in the freezer; prior to polymerization, it was cannulated into a flask filled with $CaH_2$ and vacuum transferred to another flask, with slight heat (35° C.)). The reaction mixture was allowed to stir for 2 hours before quenching by addition of degassed MeOH. The block copolymer was obtained by precipitation into 1.5 L of hexane.

Step 2. Quaternization of PS-b-PVP

PS-b-PVP (4.65 g, 0.434 mmol) was dissolved in THF (28 mL) at room temperature over 5.5 hours under a nitrogen flow. To this was then added p-chloromethyl styrene (3.96 g, 0.026 mmol); a yellow color was immediately evident. After 2 days of stirring, $^1$H NMR indicated that p-chloromethyl styrene was still present. Therefore, to the solution was added of methanol (28 mL) and within 1 hour the solution was a deep, dark green. After 3 more days of stirring the reaction was deemed complete, by $^1$H NMR (CDC$_3$/CD$_3$OD), and was precipitated into hexane. The hexane was decanted off and the green quaternized polymer was dried in vacuo at 50° C. for 48 h to yield 6.2 g (75% quaternization).

Step 3. Dispersion and Crosslinking

To a quartz reaction vessel was added the quaternized polymer (0.39 g, 0.021 mmol) followed by THF (120 mL) and D$_2$O (280 mL) resulting in a concentration of 5.2×10$^5$ M. The vessel was placed under a nitrogen flow and allowed to stir overnight, during which a light green solution developed. To the solution was added the radical initiator, 4,4'-azobis-(4-cyanovaleric acid) (0.1314 g, 0.469 mmol, 0.25 eq/PVP repeat unit). After 30 min., the initiator had dissolved completely. The vessel remained under a nitrogen flow and was fitted with a condenser. Irradiation at 254 nm was performed for 24 h. Estimation of the volume allowed for loss of ca. 25 mL of THF during irradiation. The remaining THF was removed in vacuo. The $^1$H NMR spectrum of the D$_2$O solution gave only a D$_2$O peak, thus THF-d$_8$ was added, which resulted in the appearance of polystyrene resonances.

EXAMPLE 4

Procedure for the Preparation of the Polystyrene-b-polyvinyl-pyridine (PS-b-PVP) by Anionic Chain Polymerization All purification of reagents and solvents (as described above) and polymerizations were done on a double manifold connected to a high vacuum line (10$^{-6}$ mm Hg) and Argon (99.9995%). Styrene in THF at −75° C. under Ar was initiated with the addition of sec-butyllithium via syringe. In the polymerizations of PS-b-PVP the living polystyrene was capped with one equivalent of 1,1-diphenylethylene after ca. 20 minutes of polymerization. In all cases, a small portion of the living PS was removed and quenched in degassed methanol to allow for the determination of the PS block molecular weight by GPC. 4-Vinylpyridine was transferred via cannula into the polymerization mixture and allowed to stir for 1.5 h. The living block copolymer was then quenched with degassed methanol. Removal of ca. one-half of the THF was performed in vacuo, followed by precipitation of the polymer into at least a ten-fold excess of hexane. Subsequent filtering and drying yielded a white powder. Because approximate amounts of the monomers were used, the percent yields of polymers were not calculated. The PS M$_n$, M$_w$ and M$_w$/M$_n$ values were determined from GPC based upon calibration with PS standards. The PVP and PS-b-PVP M$_n$ values were determined by comparison of the unique aromatic proton resonances of pyridyl (8.1–8.5 ppm) and styrenyl (6.2–6.7 ppm) repeat units.

Polystyrene-b-polyvinylpyridine (1) A total of 28.9 g was isolated. The PS used in this block copolymer had a M$_w$=4700 with a polydispersity of 1.17 (M$_w$/M$_n$). The molecular weight of the PVP block was 9600, which gives a total molecular weight of 14300 for the block copolymer.

Polystyrene-b-polyvinylpyridine (2) A total of 42.25 g was isolated. The PS used in this block copolymer had a M$_w$=4900 with a polydispersity of 1.14 (M$_w$/M$_n$). The molecular weight of the PVP block was 5800, which gives a total molecular weight of 10700 for the block copolymer.

Polystyrene-b-polyvinylpyridine (3) A total of 19.46 g was isolated. The PS used in this block copolymer had a M$_w$=7700 with a polydispersity of 1.10 (M$_w$/M$_n$). The molecular weight of the PVP block was 4100, which gives a total molecular weight of 11800 for the block copolymer.

EXAMPLE 5

Procedure for Quaternization of PS-b-PVP with P-chloromethylstyrene

These reactions were carried out on quantities varying from 2 to 6 g. To a flame dried 100 mL round bottom flask was added PS-b-PVP (1 equiv.) and THF (20–25 mL). After about 2 h of stirring under a N$_2$ flow, p-chloromethylstyrene (15–100 equivalents based upon polymer chains) was added. A pale yellow color was almost immediately evident. The flask was covered with aluminum foil and stirred for 16–17 h, then MeOH (20–25 mL) was added. A more intense yellow became evident over the next few hours. After 2.5 days, MeOH (7 mL) was added and an additional portion of MeOH (7 mL) was added 12 h later. Samples were taken periodically and precipitated into hexane, filtered, and dried. If $^1$H NMR indicated incomplete quaternization (presence of sharp vinyl peaks), then an additional amount of MeOH (ca. 7 mL) was added. This process was repeated every 12 h. Over this time, the reaction mixture color changed to a blue/green. The total stirring time of the reaction ranged from 100 to 190 h. The reaction mixture was then precipitated into hexane and allowed to settle for 4 to 8 h. The hexane was decanted off and the green solid was dried in vacuo for 1–2 days. IR (KBr) 3100–2960, 2930–2800, 1950, 1870, 1810, 1640, 1600, 1560, 1490, 1450, 1420, 1380–1320, 1230, 1160, 1080, 1040, 1010, 910, 840, 770, 710 cm$^{-1}$; $^1$H NMR (CD$_3$OD:CDCl$_3$, 2:1) δ1.1–2.0 (br m, CH$_2$ and CH of backbone), 5.1–5.2 (br d, J=10 Hz, (trans CH=CHPh)$_{styrene}$), 5.3–5.8 (br m, (cis CH=CHPh)$_{styrene}$ and PyrN$^+$CH$_2$Styrene), 6.2–6.7 (br m, (2 ortho ArH)$_{PS}$, (2 ArH)$_{PVP}$, gem CH$_2$=CHPh)$_{Styrene}$), 6.7–7.0 (br m, (2 meta ArE and para ArH)$_{PS}$), 7.1–7.5 (br m, (2 ArH)$_{qust. PVP}$ and (4 ArH)$_{Styrene}$), 7.8–8.2 (br m, (2 ArH)$_{PVP}$), 8.2–8.8 (br m, (2 ArH)$_{quat. PVP}$) ppm.

Polystyrene-b-Polyvinylpyridine-N-chloromethylstyrene (4). This was prepared from PS-b-PVP 1 (5.30 g, 0.371 mmol) and p-chloromethylstyrene (5.29 g, 35 mmol) with total quaternization time being 170 h to give 4 as a green solid. The fraction of pyridyl groups that were quaternized was found to be 46%, based upon the elemental analysis data for the percentages of Cl and N: yield 7.64 g (99%); (T$_g$)$_{PS}$=83° C., (T$_g$)$_{PVP}$=187° C.; Anal. calc'd. for C$_{1375}$H$_{1375}$N$_{91}$C$_{42}$ (20700): C, 79.92%; H, 6.71%; N, 6.17%; Cl, 7.21%; Found: C, 72.27%; H, 6.74%; N, 5.82%; Cl, 6.82%.

Polystyrene-b-Polyvinylpyridine-N-chloromethylstyrene (5). This was prepared from PS-b-PVP 2 (4.65 g, 0.435 mmol) and p-chloromethylstyrene (3.96 g, 26 mmol) with total quaternization time being 120 h to give 5 as a green solid. The fraction of pyridyl groups that were quaternized was 47%, based upon the elemental analysis data for the percentages of Cl to N: yield 6.20 g (98%); (T$_g$)$_{PS}$=94° C., $(T_g)_{PVP}$=193° C. Anal. calc'd. for $C_{995}H_{995}N_{55}C_{26}$ (14600): C, 81.60%; H, 6.85%; N, 5.26%; Cl, 6.29%; Found: C, 77.35%; H, 7.12%; N, 4.92%; Cl, 5.84%.

Polystyrene-b-Polyvinylpyridine-N-chloromethylstyrene (6). This was prepared from PS-b-PVP 3 (2.94 g, 0.249 mmol) and p-chloromethylstyrene (1.90 g, 12.4 mmol) with total quaternization time being 185 h to give 6 as a green solid. The fraction of pyridyl groups that were quaternized was 43%, based upon the elemental analysis data for the percentages of Cl to N: yield 3.27 g (91%); $(T_g)_{PS}$=97° C., $(T_g)_{PVP}$=not observed. Anal. calc'd. for $C_{1018}H_{1018}N_{39}C_{17}$ (14400): C, 84.90%; H, 7.12%; N, 3.79%; Cl, 4.18%; Found: C, 82.99%; H, 7.53%; N, 3.54%; Cl, 3.85%.

Polystyrene-b-Polyvinylpyridine-N-chloromethylstyrene (13). This was prepared from PS-b-PVP 2 (3.08 g, 0.288 mmol) and p-chloromethylstyrene (0.66 g, 4.35 mmol) with total quaternization time being 117 h to give 13 as a green solid. The fraction of pyridyl groups that were quaternized was 15%, based upon the elemental analysis data for the percentages of Cl to N: yield 3.25 g (95%); $(T_g)_{PS}$=103° C., $(T_g)_{PVP}$=158° C. Anal. calc'd. for $C_{833}H_{833}N_{55}Cl_8$ (11900): C, 84.09%; H, 7.06%; N, 6.47%; Cl, 2.38%; Found: C, 81.99%; H, 6.99%; N, 6.21%; Cl, 2.37%.

Polystyrene-b-Polyvinylpyridine-N-chloromethyl styrene (14). This was prepared from PS-b-PVP 2 (3.06 g, 0.286 mmol) and p-chloromethylstyrene (1.20 g, 7.85 mmol) with total quaternization time being 117 h to give 14 as a green solid. The fraction of pyridyl groups that were quaternized was 21%, based upon the elemental analysis data for the percentages of Cl to N: yield 3.29 g (92%); $(T_g)_{PS}$=98° C., $(T_g)_{PVP}$=not observed. Anal. calc'd. for $C_{869}H_{869}N_{55}C_{12}$ (12500): C, 86.38%; H, 7.25%; N, 6.38%; Cl, 3.52%; Found: C, 81.15%; H, 7.45%; N, 6.01%; Cl, 3.24%.

Polystyrene-b-Polyvinylpyridine-N-chloromethylstyrene (15). This was prepared from PS-b-PVP 3 (4.54 g, 0.385 mmol) and p-chloromethylstyrene (2.32 g, 15.2 mmol) with total quaternization time being 132 h to give 15 as a green solid. The fraction of pyridyl groups that were quaternized was 32%, based upon the elemental analysis data for the percentages of Cl to N: yield 5.29 g (99%); $(T_g)_{PS}$=101° C., $(T_g)_{PVP}$=176° C. Anal. calc'd. for $C_{982}H_{982}N_{39}C_{13}$ (13800): C, 85.52%; H, 7.18%; N, 3.96%; Cl, 3.34%; Found: C, 83.60%; H, 7.07%; N, 3.97%; Cl, 3.25%.

Polystyrene-b-Polyvinylpyridine-N-chloromethylstyrene (16). This was prepared from PS-b-PVP 3 (2.86 g, 0.242 mmol) and p-chloromethylstyrene (1.40 g, 9.15 mmol) with total quaternization time being 185 h to give 16 as a green solid. The fraction of pyridyl groups that were quaternized was 38%, based upon the elemental analysis data for the percentages of Cl to N: yield 3.30 g (97%); $(T_g)_{PS}$=101° C., $(T_g)_{PVP}$=175° C. Anal. calc'd. for $C_{1000}H_{1000}N_{39}Cl_{15}$ (14100): C, 85.20%; H, 7.15%; N, 3.88%; Cl, 3.77%; Found: C, 83.39%; H, 7.27%; N, 3.60%; Cl, 3.50%.

EXAMPLE 6

Procedure for micellization and cross-linking of Polystyrene-b-Polyvinyl-pyridine-N-chloromethylstyrene to form Particles To a 250 mL quartz reaction vessel was added polystyrene-b-polyvinylpyridine-N-chloromethylstyrene and appropriate volumes of THF and then $H_2O$ to give a solution concentration from $5\times10^{-5}$ to $9\times10^{-5}$ M and a THF:$H_2O$ ratio of approximately 1:2.5. A septum was placed in the flask and the reaction mixture was stirred under a $N_2$ flow for 1.75 to 19 h depending upon the experiment. The initiator 4,4'-azobis(4-cyanovaleric acid) was then added and allowed to stir for up to 2 h. Irradiation was then performed on the open flask for 24 h within a Rayonet photochemical reactor, which resulted in a decrease in volume due to loss of ca. 50% of the THF from the heat generated by the lamp during irradiation. All samples were filtered through a 0.45 µm PTFE filter and AFM was performed. Spectroscopic characterization for each of the particles included the following data: IR (KBr) 3530– 3100, 3060, 3030, 3000, 2940–2820, 1740–1680, 1650, 1600, 1560, 1480, 1470, 1450–1370, 1280, 1240–1170, 1100–1040, 780, 710 $cm^{-1}$. Solution-state $^1H$ NMR ($D_2O$: THF-$d_8$, 3:1) δ1–2.8 (aliphatic protons of polymer backbone and initiator), 6.3–7.5 (aromatic protons of PS) ppm. Solid-state $^{13}C$ NMR δ10–50 (PS and PVP aliphatic backbone, initiator methyl and methylene carbons), 50–75 (benzylic methylenes of p-chloromethylstyrene-quaternized PVP and initiator methine), 110–150 (PS and PVP aromatic carbons), 150–165 (initiator carboxylic acid carbonyl) ppm.

Particle (7). This was prepared from 4 (0.35 g, 0.017 mmol) in THF (70 mL) and $H_2O$ (170 mL) and allowed to And stir for 16 h. 4,4'-azobis(4-cyanovaleric acid) (0.17 g, 0.59 mmol) was added (63 mol % based on available styrenyl groups) and the reaction mixture was allowed to stir for 1 h prior to irradiation for 24 h. During irradiation, the solution changed color from very light green to bright yellow. An average diameter of 9.0±3.0 nm was obtained from AFM.

Particle (8). This was prepared from 5 (0.21 g, 0.014 mmol) in THF (70 mL) and $H_2O$ (180 mL) and allowed to stir for 12 h. 4,4'-azobis(4-cyanovaleric acid) (0.08 g, 0.29 mmol) was added (63 mol % based on available styrenyl groups) and the reaction mixture was allowed to stir for 0.5 h prior to irradiation for 24 h. During irradiation, the solution changed color from very light green to bright yellow. An average diameter of 15±2 nm was obtained from AFM.

Particle (9). This was prepared from 6 (0.23 g, 0.016 mmol) in THF (60 mL) and $H_2O$ (150 mL) and allowed to stir for 17.75 h. 4,4'-azobis(4-cyanovaleric acid) (0.05 g, 0.18 mmol) was added (61 mol % based on available styrenyl groups) and the reaction mixture was allowed to stir for 1.25 h prior to irradiation for 24 h. During irradiation, the solution changed color from very light green to yellow with an oil-like precipitate forming on the sides of the flask. An average diameter of 23±4 nm was obtained from AFM.

Particle (10). This was prepared from 4 (0.24 g, 0.012 mmol) in THF (70 mL) and $H_2O$ (180 mL) and allowed to stir for 2 h. 4,4'-azobis(4-cyanovaleric acid) (0.11 g, 0.40 mmol) was added (64 mol % based on available styrenyl groups) and the reaction mixture was allowed to stir for 0.5 h prior to irradiation for 24 h. During irradiation, the solution changed color from very light green to a light yellow. An average diameter of 7±2 nm was obtained from AFM.

Particle (11). This was prepared from 5 (0.21 g, 0. 014 mmol) in THF (70 mL) and $H_2O$ (180 mL) and allowed to stir for 2 h. 4,4'-azobis(4-cyanovaleric acid) (0.08 g, 0.29 mmol) was added (63 mol % based on available styrenyl groups) and the reaction mixture was allowed to stir for 0.5 h prior to irradiation for 24 h. During irradiation, the solution changed color from very light green to light yellow. An average diameter of 14±2 nm was obtained from AFM.

Particle (12). This was prepared from 15 (0.24 g, 0.017 mmol) in THF (80 mL) and $H_2O$ (170 mL) and allowed to stir for 1.5 h. 4,4'-azobis(4-cyanovaleric acid) (0.05 g, 0.19 mmol) was added (85 mol % based on available styrenyl groups) and allowed to stir for 0.25 h prior to irradiation for 24 h. During irradiation, the solution changed color from very light green to a light yellow and was turbid with formation of a white precipitate on the sides and bottom of the flask. An average diameter of 19±4 nm was obtained from AFM.

Particle (17). This was prepared from 13 (0.20 g, 0.017 mmol) in THF (60 mL) and $H_2O$ (150 mL) and allowed to stir for 12.75 h. 4,4'-azobis(4-cyanovaleric acid) (0.02 g, 0.075 mmol) was added (55 mol % based on available styrenyl groups) and the reaction mixture was allowed to stir for 0.75 h prior to irradiation for 24 h. During irradiation, the solution changed color from very light green to yellow and was slightly turbid with some precipitate floating in the solution. After a week, precipitate appeared on the bottom of the storage flask. An average diameter of 18±3 nm was obtained from AFM.

Particle (18). This was prepared from 14 (0.21 g, 0.017 mmol) in THF (60 ml) and $H_2O$ (160 mL) and allowed to stir for 17 h. 4,4'-azobis(4-cyanovaleric acid) (0.10 g, 0.36 mmol) was added (178 mol % based on available styrenyl groups) and the reaction mixture was allowed to stir for 2 h prior to irradiation for 24 h. During irradiation, the solution changed color from very light green to bright yellow with no evidence of precipitate. After ca. 10 days some precipitate had formed in the bottom of the storage flask. An average diameter of 16±3 nm was obtained from AFM.

Particle (19). This was prepared from 15 (0.23 g, 0.017 mmol) in THF (70 mL) and $H_2O$ (180 mL) and allowed to stir for 11.5 h. 4,4'-azobis(4-cyanovaleric acid) (0.05 g, 0.19 mmol) was added (85 mol % based on available styrenyl groups) and the reaction mixture was allowed to stir for 0.5 h prior to irradiation for 24 h. During irradiation, the solution changed color from very light green to light yellow and was turbid with white solid precipitate on the sides of the flask and floating in the solution. An average diameter of 27±5 nm was obtained from AFM.

Particle (20). This was prepared from 16 (0.24 g, 0.017 mmol) in THF (70 mL) and $H_2O$ (170 mL) and allowed to stir for 15.5 h. 4,4'-azobis(4-cyanovaleric acid) (0.05 g, 0.18 mmol) was added (67 mol % based on available styrenyl groups) and the reaction mixture was allowed to stir for 0.5 h prior to irradiation for 24 h. During irradiation, the solution changed color from very light green to light yellow and was turbid with white solid precipitate on the sides of the flask. An average diameter of 29±2 nm was obtained from AFM.

EXAMPLE 7

Bromo-polyethylene oxide (1950)-monomethyl ether (21)

Polyethylene glycol monomethylether (20.7 g, 0.011 mol, Scientific Polymer Products, MW 1900) was dissolved in THF (35 mL) with application of heat, and then carbon tetrabromide (8.37 g, 0.025 mol) and triphenyl phosphine (6.54 g, 0.025 mol) were added. After 5–10 minutes of stirring under a $N_2$ flow, a cloudy white precipitate began to form. The solution was allowed to stir for 0.5 hour, and then the THF was removed in vacuo. The product was purified by flash column chromatography eluting with $CH_2C_2$ and increasing the polarity to 10% $MeOH/CH_2Cl_2$ to give 21 as a white solid: yield 18.6 g (88%). $^1H$ NMR ($CDCl_3$) δ3.30 (s, —$OCH_3$), 3.40 (t, J=8 Hz, $BrCH_2CH_2$—), 3.58 (br m, —$OCH_2CH_2$—), 3.74 (t, J=8 Hz, $BrCH_2CH_2$—) ppm. Anal. calc'd. for $C_{85}H_{171}BrO_{42}$ (1950): C, 52.49%; H, 8.86%; Br, 4.11%; Found: C, 51.90%; H, 8.56%; Br, 4.42%.

EXAMPLE 6

Procedure for the Quaternization of Polystyrene-b-Polyvinyl-pyridine-N-chloromethylstyrene with 21 and then Crosslinking to Form the Particles To a 250 mL quartz reaction vessel was added polystyrene-b-polyvinylpyridine-N-chloromethylstyrene and an appropriate volume of THF and then $H_2O$ to give a solution concentration between $5\times10^{-5}$ and $7\times10^{-5}$ M in a $THF:H_2O$ solvent mixture with a ratio of approximately 1:2.5. The reaction mixture was allowed to stir for 4 to 6.5 hours under a $N_2$ flow. The functionalized polyethyleneoxide 21 was added and the mixture was allowed to stir for an additional 11–13 hours before 4,4'-azobis(4-cyanovaleric acid) was added (50 to 80 mol % based available styrenyl groups) and allowed to stir for up to 1 hour. Irradiation on the open flask was then performed for 24 hours within a Rayonet photochemical reactor, which resulted in a decrease in volume due to loss of THF from the heat generated by the lamp. All samples were filtered through a 0.45 μm PTFE filter and AFM was performed.

PEO-functionalized Particle (22). To a quartz reaction vessel was added 15 (0.25 g, 0.018 mmol), THF (80 mL) and $H_2O$ (180 mL). The reaction mixture was stirred for 5.5 hours under a $N_2$ flow, 21 (0.26 g, 0.14 mmol, 7.6 equiv.) was added, and stirring was continued for 12.25 hours. 4,4'-azobis(4-cyanovaleric acid) (0.05 g, 0.19 mmol) was added (79 mol % based on available styrenyl groups), the reaction mixture was allowed to stir for 0.25 hour, and the reaction vessel was then irradiated for 24 hours. During irradiation, the solution became slightly yellow in color and was extremely turbid with some precipitate formation. An average diameter of 22±4 nm was obtained from AFM.

PEO-functionalized Particle (23). To a quartz reaction vessel was added 5 (0.20 g, 0.014 mmol), THF (70 mL) and $H_2O$ (180 mL). The reaction mixture was stirred for 4 h under a $N_2$ flow, 21 (0.21 g, 0.11 mmol, 7.9 equiv.) was added, and stirring was continued for 12 hours. 4,4'-azobis (4-cyanovaleric acid) (0.06 g, 0.22 mmol) was added (50 mol % based on available styrenyl groups), the reaction mixture was allowed to stir for 0.5 hour, and the reaction vessel was then irradiated for 20.5 hours. The particle solution was a golden yellow color. An average diameter of 12±2 nm was obtained from AFM.

PEO-functionalized Particle (24). To a quartz reaction vessel was added 4 (0.25 g, 0.012 mmol), THF (70 mL) and $H_2O$ (180 mL). The reaction mixture was stirred for 5.25 hours under a $N_2$ flow, 21 (0.19 g, 0.10 mmol, 7.9 equiv.) was added, and stirring was continued for 12.25 hours. 4,4'-azobis(4-cyanovaleric acid) (0.10 g, 0.36 mmol) was added (54 mol % based on available styrenyl groups), the reaction mixture as allowed to stir for 0.5 hour, and the reaction vessel was then irradiated for 24 hours. The particle solution was a golden yellow color. An average diameter of 12±2 nm was obtained from AFM.

TABLE 10

Data for the Particles

| particle | PS:PVP Ratio | Polymer Molecular Weights | Percent Quaternization | PEO Quaternization? | Micelle Formation Time (h) | Particle Diameter[a] (nm) |
|---|---|---|---|---|---|---|
| Variation In PS:PVP block length ratios: | | | | | | |
| 7 | 1:2.0 | 20700 | 46 | NO | 17 | 9 ± 3 |
| 8 | 1:1.2 | 14600 | 47 | NO | 12.5 | 15 ± 2 |
| 9 | 1.9:1 | 14400 | 43 | NO | 19 | 23 ± 4 |
| Variation in micelle formation time: | | | | | | |
| 10 | 1:2.0 | 20700 | 46 | NO | 2.5 | 7 ± 2 |
| 7 | 1:2.0 | 20700 | 46 | NO | 17 | 9 ± 3 |
| 11 | 1:1.2 | 14600 | 47 | NO | 2.5 | 14 ± 2 |
| 8 | 1:1.2 | 14600 | 47 | NO | 12.5 | 15 ± 2 |

TABLE 10-continued

Data for the Particles

| par-ticle | PS:PVP Ratio | Polymer Molecular Weights | Percent Quaternization | PEO Quaternization? | Micelle Formation Time (h) | Particle Diameter[a] (nm) |
|---|---|---|---|---|---|---|
| 12 | 1.9:1 | 13800 | 32 | NO | 1.75 | 19 ± 4 |
| 19 | 1.9:1 | 13800 | 32 | NO | 12 | 27 ± 5 |
| Variation in percent quaternization: | | | | | | |
| 17 | 1:1.2 | 11900 | 15 | NO | 13.5 | 18 ± 3 |
| 18 | 1:1.2 | 12500 | 21 | NO | 19 | 16 ± 3 |
| 8 | 1:1.2 | 14600 | 47 | NO | 12.5 | 15 ± 2 |
| 19 | 1.9:1 | 13800 | 32 | NO | 12 | 27 ± 5 |
| 20 | 1.9:1 | 14100 | 38 | NO | 16 | 29 ± 2 |
| 9 | 1.9:1 | 14400 | 43 | NO | 19 | 23 ± 4 |
| Addition of PEO: | | | | | | |
| 24 | 1:2.0 | 20700[b] | 46[b] | YES | 18 | 12 ± 2 |
| 7 | 1:2.0 | 20700 | 46 | NO | 17 | 9 ± 3 |
| 23 | 1:1.2 | 14600[b] | 47[b] | YES | 16.5 | 12 ± 2 |
| 8 | 1:1.2 | 14600 | 47 | NO | 12.5 | 15 ± 2 |
| 22 | 1.9:1 | 13800[b] | 32[b] | YES | 18 | 22 ± 4 |
| 19 | 1.9:1 | 13800 | 32 | NO | 12 | 27 ± 5 |

[a]Number average particle heights from measurement of 200–300 particles by tapping mode AFM of particles adsorbed onto mica. Uncertainties are calculated as standard deviations of average particle sizes.
[b]The molecular weights and quaternization percentages for 22–24 are prior to PEO quaternization.
PS = polystyrene
PVP = polyvinylpyridine
PEO = polyethyleneoxide

TABLE 11

Glass Transition Temperatures ($T_g$'s) of the polystyrene (PS) and polyvinylpyridine (PV) blocks of 4–6, obtained from DSC scans with heating rates of 10° C./min over the temperature range from 50 to 220° C.

| DSC Heating Scan No. | 4 | | 5 | | 6 | | 13 | |
|---|---|---|---|---|---|---|---|---|
| | PS ($T_g$) °C. | PVP ($T_g$) °C. | PS ($T_g$) °C. | PVP ($T_g$) °C. | PS ($T_g$) °C. | PVP ($T_g$) °C. | PS ($T_g$) °C. | PVP ($T_g$) °C. |
| Second | 80 | 183 | 93 | — | — | [a] | 98 | 148 |
| Third | 83 | 187 | 94 | 193 | 97 | [b] | 103 | 158 |
| Fourth | 82 | 191 | 92 | 197 | 96 | [b] | 102 | 154 |
| Fifth | 78 | 199 | 92 | 200 | 96 | [b] | 100 | 157 |

[a]A broad endotherm was observed from 120 to 190° C.
[b]A broad endotherm was observed from 120 to 220° C.

EXAMPLE 7

Crosslinking of Polystyrene-b-poly(acrylic acid) (PS-b-PAA) with 1-(3-Dimethylaminopropyl)-3-ethylcarbodiimide and 2,2'-(Ethylenedioxy)bis(ethylamine) and Poly(ethyleneimine) (molecular weight=600)

The crosslinking reaction by amide links was performed for the micelles formed from diblock PS-b-PAA in solution (Scheme 3)

Scheme 3
The Crosslinking of the Carboxylic Acid Side Chain Groups of the Polyacrylic Acid Block by Amide Bond Formation with 1-(3-Dimethylaminopropyl)-3-ethylcarbodiimide and 2,2'-(Ethylenedioxy)bis(ethylamine) and Poly (ethyleneimine).

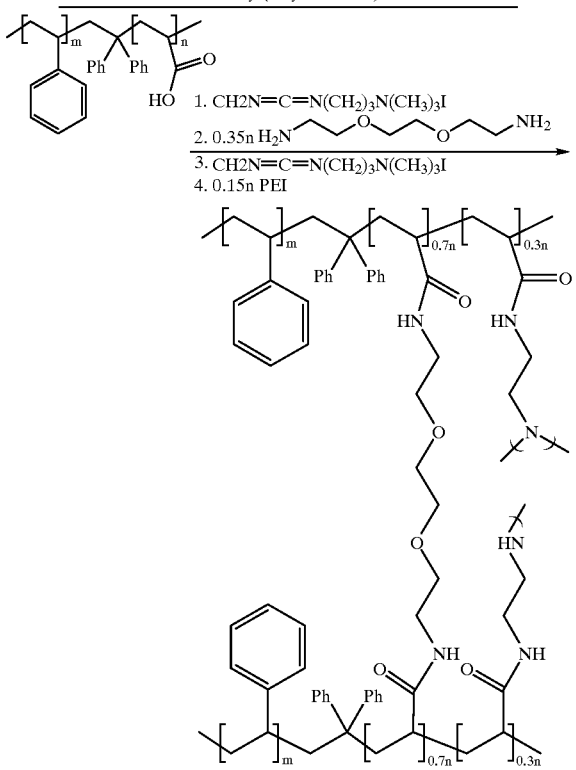

To a stock solution of PS-b-PAA aqueous micellar solution (0.7 mg/mL, 35 mL, 0.127 mmol acrylic acid unit) was added 1-(3-dimethylaminopropyl)-3-ethylcarbodiimide methiodide (26.4 mg, 0.0889 mmol, 70% of the total amount of acrylic acid units). The mixture was allowed to stir for 15 min before the crosslinking reagent 2,2'-(ethylenedioxy)bis(ethylamine) (6.59 mg, 0.0445 mmol) was added. The reaction mixture was stirred for 30 minutes at room temperature. Then, to the mixture was added 1-(3-dimethylaminopropyl)-3-ethylcrbodiimide methiodide (11.3 mg, 0.0381 mmol, 30% of the total amount of acrylic acid units) and polyethylenimine (3.28 mg). The resulting mixture was stirred for 3 hours at room temperature and then transferred to a dialysis bag and dialyzed against distilled water for 24 hours to remove small by-products.

EXAMPLE 8

Crosslinking of Polystyrene-b-poly(acrylic acid) (PS-b-PAA) with 1-(3-Dimethylaminopropyl)-3-ethylcarbodiimide methi8odide and Triethylenetetramine or 1,7-Diaza-4,10-diazonium-4,4,10,10-tetramethylundecane diiodide The crosslinking reaction by amide links was performed for the micelles formed from diblock PS-b-PAA in aqueous solution (Scheme 4).

Scheme 4
The Crosslinking of the Carboxylic Acid Side Chain Groups of the Polyacrylic Acid Block by Amide Bond Formation with 1-(3-Dimethylaminopropyl)-3-ethylcarbodiimide methi8odide and Triethylenetetramine or 1,7-Diaza-4,10-diazonium-4,4,10, 10-tetramethylundecane diiodide.

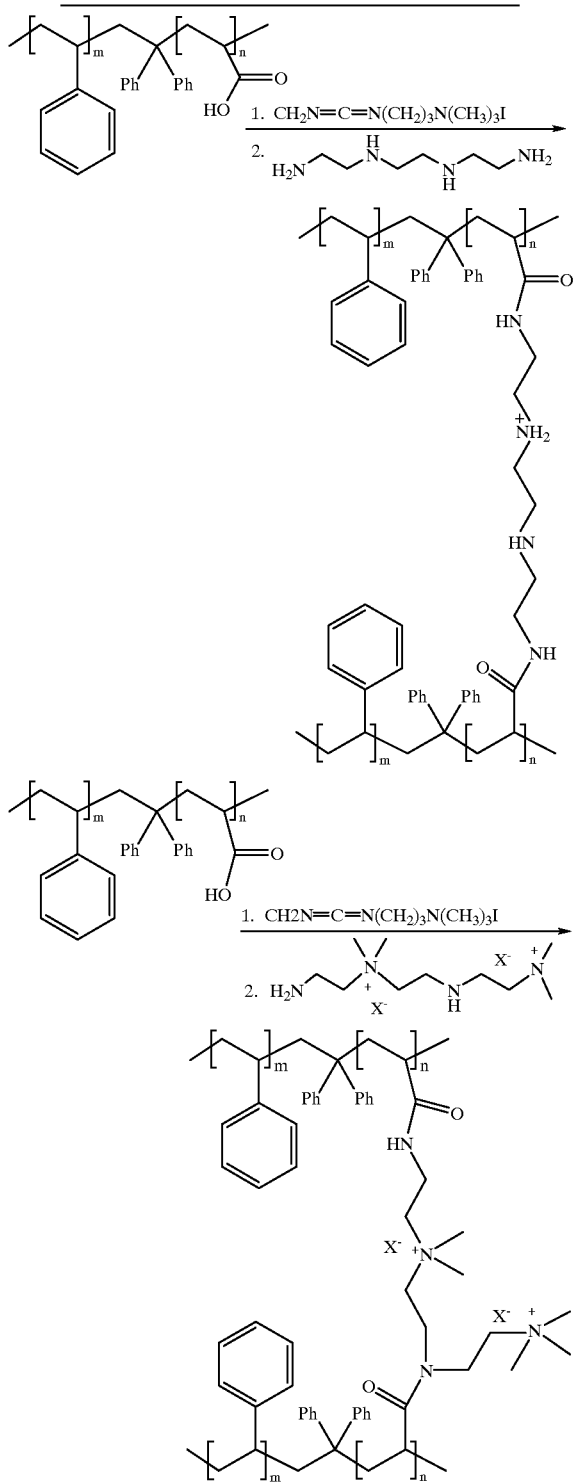

To a stock solution of PS-b-PAA aqueous micellar solution (0.7 mg/mL, 35 mL, 0.127 mmol acrylic acid unit) was added 1-(3-dimethylaminopropyl)-3-ethylcarbodiimide methiodide (37.7 mg, 0.127 mmol). The mixture was allowed to stir for 15 min before the crosslinking reagent triethylenetetramine or 1,7-diaza-4,10-diazonium-4,4,10, 10-tetramethylundecane diiodide was added. The resulting mixture was stirred for 3 hours at room temperature and then transferred to a dialysis bag and dialyzed against distilled water for 24 hours to remove small by-products.

EXAMPLE 9

Uptake of Sodium Cholate by Particles of this Invention. Assay Using Sigma Diagnostic Bile Acids Reagent Test Kit and UW-Vis Absorption Monitored at 530 nm The following experiments demonstrate the ability of the particles of this invention to bind bile acids, in particular cholic acid or its sodium salt.

In these timecourse experiments a solution or suspension of one of particles of this invention was placed inside a dialysis bag. A separate dosing solution was prepared containing an indicated amount of sodium cholate. The filled dialysis bag was immersed in the dosing solution at 25° C. Thus there was no direct mixing of particles and sodium cholate. Subsamples of the dosing solution were then collected as a function of time. The concentration of cholic acid in each subsample was measured as a function of time. Particles possessing different chemical and physical properties were examined in these experiments. The control experiment was performed in a similar fashion, except that the dialysis bag was filled with deionized water rather than with a solution or suspension of particles.

1. Uptake of Sodium Cholate by the Particle of Example 2

1a. A solution of the particles of Example 2 (10 mL, 1 mg/mL) was added to a dialysis bag and the dialysis bag was transferred to 200 mL of sodium cholate solution (initial concentration of sodium cholate is 0.20 mM, and becomes 0.19 mM due to dilution by solvent in the dialysis bag). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 1 min | 0.520 | 0.200 | 0 | 0 |
| 30 min | 0.525 | 0.202 | — | — |
| 4 h | 0.570 | 0.219 | — | — |
| 6 h | 0.527 | 0.203 | — | — |
| 17 h | 0.532 | 0.205 | — | — |
| 20 h | 0.565 | 0.217 | — | — |

(SCK refers to a particle of the present invention. More specifically it means "Shell-Crosslinked Kenedel.")

1b. A solution of the particles of Example 2 (10 mL, 1 mg/mL) was added to a dialysis bag and the dialysis bag was transferred to 200 mL of sodium cholate solution (initial concentration of sodium cholate is 2.0 mM). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 1 min | 0.36 | 2.0 | 0 | 0 |
| 30 min | 0.36 | 2.0 | — | — |
| 4 h | 0.35 | 1.9 | — | — |
| 11 h | 0.37 | 2.1 | — | — |
| 24 h | 0.37 | 2.1 | — | — |

2. Uptake of Sodium Cholate by the Particles of Example 7

2a. A solution of the particles of Example 7 (10 mL, 1 mg/mL) was added to a dialysis bag and the dialysis bag was transferred to 200 mL of sodium cholate solution (initial concentration 0.2 mM, diluted concentration 0.19 mm). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 1 min | 0.570 | 0.200 | 0 | 0 |
| 10 min | 0.590 | 0.207 | — | — |
| 4 h | 0.557 | 0.189 | 0.09 | 0.009 |
| 6 h | 0.525 | 0.184 | 0.54 | 0.054 |
| 17 h | 0.521 | 0.183 | 0.63 | 0.063 |
| 20 h | 0.511 | 0.179 | 0.99 | 0.099 |
| 21 h | 0.522 | 0.183 | 0.63 | 0.063 |

2b. A solution of the particles of Example 7 (11 mL, 1 mg/mL) was added to a dialysis bag and the dialysis bag was transferred to 200 mL of sodium cholate solution (initial concentration 1.20 mM, diluted concentration 1.14 mm). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 5 min | 0.412 | 1.20 | 0 | 0 |
| 45 min | 0.385 | 1.12 | 1.8 | 0.17 |
| 1 h | 0.390 | 1.14 | 0 | 0 |
| 2 h | 0.330 | 0.961 | 16.3 | 1.5 |
| 6 | 0.330 | 0.961 | 16.3 | 1.5 |
| 19 | 0.310 | 0.903 | 21.5 | 2.0 |
| 21 | 0.317 | 0.923 | 19.9 | 1.8 |
| 22 | 0.327 | 0.950 | 17.2 | 1.6 |

3. Uptake of Sodium Cholate by the Particles of Example 8, Wherein the Crosslinking Reagent is Triethylenetetraamine Run 1. A solution of the particles of Example 8 wherein the crosslinking reagent is triethylenetetraamine (11.5 mL, 0.89 mg/mL) was added to a dialysis bag and the dialysis bag was transferred to 200 mL of sodium cholate solution (initial concentration 1.205 mM, diluted concentration 1.139 mM). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 0 min | 0.391 | 1.205 | 0 | 0 |
| 15 min | 0.380 | 1.166 | — | — |
| 1 h | 0.372 | 1.142 | — | — |
| 3 h | 0.364 | 1.117 | 2.0 | 0.19 |
| 6 h | 0.348 | 1.068 | 6.5 | 0.63 |
| 12 h | 0.334 | 1.025 | 10.4 | 1.01 |
| 22 h | 0.315 | 0.967 | 15.4 | 1.50 |
| 28 h | 0.325 | 0.997 | 12.9 | 1.25 |
| 32 h | 0.325 | 0.997 | 12.9 | 1.25 |

Run 2. A solution of the particles of Example 8 wherein the crosslinking reagent is triethylenetetraamine (10.0 mL, 1.0 mg/mL) was added to a dialysis bag and the dialysis bag was transferred to 200 mL of sodium cholate solution (initial concentration 1.20 mM, diluted concentration 1.14 mM). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 0 min | 0.370 | 1.20 | 0 | 0 |
| 30 min | 0.346 | 1.12 | 1.8 | 0.18 |
| 1 h | 0.346 | 1.12 | 1.8 | 0.18 |
| 3 h | 0.346 | 1.12 | 1.8 | 0.18 |
| 7 h | 0.344 | 1.12 | 1.8 | 0.18 |
| 9 h | 0.342 | 1.11 | 2.7 | 0.27 |
| 18 h | 0.340 | 1.10 | 3.6 | 0.36 |
| 20 h | 0.332 | 1.08 | 5.4 | 0.54 |

4. Uptake of Sodium Cholate by the Particles of Example 8, Wherein the Crosslinking Reagent Is 1,7-Diaza-1,10-diazonium-4,4,10,10-tetramethylundecane Diiodide A solution of the particles of Example 8 wherein the crosslinking reagent is 1,7-diaza-1,10-diazonium-4,4,10,10-tetramethylundecane diiodide (10.0 mL, 0.9 mg/mL) was added to a dialysis bag and the dialysis bag was transferred to 200 mL of sodium cholate solution (initial concentration 1.20 mM, diluted concentration 1.14 mM). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 0 min | 0.406 | 1.20 | 0 | 0 |
| 30 min | 0.382 | 1.13 | 0.90 | 0.10 |
| 1 h | 0.382 | 1.13 | 0.90 | 0.10 |
| 3 h | 0.381 | 1.13 | 0.90 | 0.10 |
| 7 h | 0.385 | 1.14 | — | — |
| 9 h | 0.374 | 1.10 | 3.6 | 0.40 |
| 18 h | 0.366 | 1.08 | 5.4 | 0.60 |
| 20 h | 0.356 | 1.05 | 8.1 | 0.90 |

5. Comparison Experiment of Cholestyramine Resin

A sample containing 10.0 mg cholestyramine in 10 mL deionized water was added to a dialysis bag and the dialysis bag was transferred to 200 mL of sodium cholate solution (initial concentration 1.20 mM, diluted concentration 1.14 mM). Subsamples of the sodium cholate solution were taken as a function of time and assayed by UV absorbance at 530 nm wavelength.

| Time | Absorbance | Cholic acid conc. (mM) | Cholic acid Uptake (g) | g cholic acid per g of SCK |
|---|---|---|---|---|
| 0 min | 0.400 | 1.20 | 0 | 0 |
| 30 min | 0.396 | 1.19 | — | — |
| 1 h | 0.392 | 1.18 | — | — |
| 3 h | 0.385 | 1.16 | — | — |
| 7 h | 0.386 | 1.16 | — | — |
| 9 h | 0.384 | 1.15 | — | — |
| 18 h | 0.366 | 1.10 | 3.6 | 0.36 |
| 20 h | 0.362 | 1.08 | 5.4 | 0.54 |

6. Control Experiment

A 10 mL sample of deionized water was added to a dialysis bag and the dialysis bag was transferred to 200 mL of sodium cholate solution (initial concentration 1.20 mM, diluted concentration 1.14 mM).

| Time | Absorbance | Cholic acid conc. (mM) | Cholic acid Uptake (g) | g cholic acid per g of SCK |
|---|---|---|---|---|
| 0 min | 0.378 | 1.20 | 0 | 0 |
| 30 min | 0.363 | 1.15 | 0 | 0 |
| 1 h | 0.354 | 1.12 | 0 | 0 |
| 3 h | 0.382 | 1.21 | 0 | 0 |
| 7 h | 0.368 | 1.17 | 0 | 0 |
| 9 h | 0.366 | 1.16 | 0 | 0 |
| 18 h | 0.365 | 1.16 | 0 | 0 |
| 20 h | 0.367 | 1.17 | 0 | 0 |

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A particle comprising an amphiphilic copolymer and having a core and a crosslinked shell which differs from said core in hydrophilicity and hydrophobicity, said shell comprising a region of said copolymer which differs in hydrophilicity and hydrophobicity from another region of said copolymer in said core, said copolymer being crosslinked in said region within said shell, said copolymer region in said shell having a degree of crosslinking ranging from about 1% to about 80%, said copolymer being selected from among amphiphilic copolymers physically conducive to forming micelles prior to crosslinking.

2. The particle of claim 1, wherein said crosslinked shell is permeable.

3. The particle of claim 1, wherein said crosslinked shell is hydrophilic and said core is hydrophobic.

4. The particle of claim 3, wherein said amphiphilic copolymer is crosslinked via functional groups within the hydrophilic region.

5. The particle of claim 3, wherein said hydrophobic core is also crosslinked.

6. The particle of claim 5, wherein said amphiphilic copolymer is crosslinked via functional groups within the hydrophobic region.

7. The particle of claim 1, wherein said crosslinked shell is hydrophobic and said core is hydrophilic.

8. The particle of claim 7, wherein said amphiphilic copolymer is crosslinked via functional groups within the hydrophobic region.

9. The particle of claim 7, wherein said hydrophilic core is also crosslinked.

10. The particle of claim 9, wherein said amphiphilic copolymer is crosslinked via functional groups within the hydrophilic region.

11. The particle of claim 1, where said amphiphilic copolymer is selected from the group consisting of amphiphilic diblock copolymers, amphiphilic triblock copolymers, amphiphilic multiblock copolymers, and amphiphilic graft copolymers.

12. The particle of claim 1, wherein copolymer blocks comprising said crosslinked shell are crosslinked by condensation reactions, chain polymerization reactions, or addition reactions.

13. The particle of claim 12, wherein the copolymer blocks comprising said crosslinked shell are crosslinked using a titrimetric crosslinking reagent.

14. The particle of claim 1, wherein the degree of crosslinking ranges from about 10% to about 50%.

15. The particle of claim 1, wherein said particle has an average molecular weight in the range of from about 10,000 to about 5,000,000.

16. The particle of claim 1, wherein said crosslinked shell has a positive or negative charge.

17. The particle of claim 1, wherein said core has a positive or negative charge.

18. The particle of claim 1, further comprising a pharmaceutically active agent.

19. The particle of claim 5, wherein said core comprises polyisoprene.

20. The particle of claim 1, wherein said crosslinked shell comprises an amphiphilic copolymer region selected from the group consisting of polyvinylpyridine-N-chloromethylstyrene, polyvinylpyridine-N-chloromethylstyrene-co-polyvinylpyridine-N-bromopolyethylene oxide monomethyl ether, and polyacrylic acid.

21. The particle of claim 20 wherein said crosslinked shell comprises polyacrylic acid crosslinked with 2,2'-(ethylenedioxy)bis(ethylamine) or $\alpha,\omega$-(polyethyleneoxy)bis(ethylamine).

22. The particle of claim 1, wherein said core comprises an amphiphilic copolymer region selected from the group consisting of polystyrene, polyisoprene, poly(1,4-isoprene), and poly(6-hydroxycaproic acid).

23. The particle of claim 1 wherein said amphiphilic copolymer is a graft copolymer.

24. A pharmaceutical composition, comprising a particle comprising amphiphilic copolymers, wherein said particle has a crosslinked shell domain and an interior core domain, or a pharmaceutically acceptable salt thereof, and a pharmaceutically acceptable carrier, excipient, or diluent.

25. The pharmaceutical composition of claim 24, wherein said crosslinked shell domain is permeable.

26. A pharmaceutical composition, comprising a particle comprising amphiphilic copolymers, wherein said particle has a crosslinked shell domain and an interior core domain, or a pharmaceutically acceptable salt thereof;

a pharmaceutically active agent; and a pharmaceutically acceptable carrier, excipient, or diluent.

27. The pharmaceutical composition of claim 26, wherein said pharmaceutically active agent is present in or on said particle.

28. A method of producing a particle comprising an amphiphilic copolymer and having a core and a crosslinked shell which differs from said core in hydrophilicity and hydrophobicity, the method comprising:
(a) preparing a micellar assembly comprising an amphiphilic copolymer having reactive functionalities, wherein an interior of said micellar assembly comprise regions of said copolymer that differ in hydrophobicity and hydrophilicity from other regions of said copolymer within a periphery of said assembly; and
(b) crosslinking regions of said copolymer in said periphery of said micellar assembly to produce a particle comprising amphiphilic copolymers having a core and a crosslinked shell.

29. The method of claim 28, wherein said micellar assembly is prepared by placing said amphiphilic copolymers at an appropriate concentration in a solvent system effective in orienting said amphiphilic copolymers into micelles.

30. The method of claim 29, wherein said appropriate concentration of said amphiphilic copolymers is in the range of from about 0.001 mg/mL to about 10 mg/mL.

31. The method of claim 29, wherein said solvent system predominantly comprises a hydrophilic solvent.

32. The method of claim 31, wherein said crosslinked shell is hydrophilic.

33. The method of claim 29, wherein said solvent system predominantly comprises a hydrophobic solvent.

34. The method of claim 33, wherein said crosslinked shell is hydrophobic.

35. The method of claim 28, wherein the regions of said copolymers in said periphery are crosslinked using a titrimetric crosslinking reagent.

36. The method of claim 28, further comprising crosslinking regions of said copolymers in said interior blocks of said micellar assembly to produce a particle having a crosslinked core.

37. A particle comprising an amphiphilic copolymer and having a core and a crosslinked shell which differs from said core in hydrophilicity and hydrophobicity, said shell comprising a region of said copolymer which differs in hydrophilicity and hydrophobicity from another region of said copolymer in said core, said copolymer being crosslinked in said region within said shell, said copolymer region in said shell having a degree of crosslinking of at least about 10%, said copolymer being selected from among amphiphilic copolymers physically conducive to forming micelles prior to crosslinking.

38. The particle of claim 37 wherein said crosslinked shell is hydrophilic and said core is hydrophobic.

39. The particle of claim 38 wherein said hydrophobic core is also crosslinked.

40. The particle of claim 37 wherein said crosslinked shell is hydrophobic and said core is hydrophilic.

41. The particle of claim 40 wherein said hydrophilic core is also crosslinked.

42. The particle of claim 37 wherein said amphiphilic copolymer is selected from the group consisting of amphiphilic diblock copolymers, amphiphilic triblock copolymers, amphiphilic multiblock copolymers, and amphiphilic graft copolymers.

43. The particle of claim 37 wherein the degree of crosslinking ranges from about 10% to about 50%.

44. The particle of claim 37 wherein said crosslinked shell comprises an amphiphilic copolymer region selected from the group consisting of polyvinylpyridine-N-chloromethylstyrene, polyvinylpyridine-N-chloromethylstyrene-co-polyvinylpyridine-N-bromopolyethylene oxide monomethyl ether, and polyacrylic acid.

45. The particle of claim 44 wherein said crosslinked shell comprises polyacrylic acid crosslinked with 2,2'-(ethylenedioxy)bis(ethylamine) or α,ω-(polyethyleneoxy)bis(ethylamine).

46. The particle of claim 37 wherein said core comprises an amphiphilic copolymer region selected from the group consisting of polystyrene, polyisoprene, poly(1,4-isoprene), and poly(6-hydroxycaproic acid).

47. The particle of claim 46 wherein said core comprises polyisoprene.

48. A formulation comprising the particle of claim 37 and a carrier, excipient or diluent which is (i) pharmaceutically acceptable, (ii) agronomically acceptable, (iii) gastronomically acceptable, and/or (iv) acceptable for use in foods or cosmetics.

49. The formulation of claim 48 comprising a pharmaceutically acceptable carrier, excipient or diluent and a pharmaceutically active agent.

50. The formulation of claim 49 wherein the pharmaceutically active agent is contained within the particle.

51. The formulation of claim 48 comprising an agronomically acceptable carrier, excipient or diluent and a pesticidally active agent.

52. The formulation of claim 51 wherein the pesticidally active agent is contained within the particle.

53. The formulation of claim 48 comprising a gastronomically acceptable carrier, excipient or diluent.

54. The formulation of claim 48 comprising a carrier, excipient or diluent acceptable for use in foods.

55. The formulation of claim 48 comprising a carrier, excipient or diluent acceptable for use in cosmetics.

56. A particle comprising an amphiphilic copolymer and having a core and a crosslinked shell which differs from said core in hydrophilicity and hydrophobicity, said shell comprising a region of said copolymer which differs in hydrophilicity and hydrophobicity from another region of said copolymer in said core, said copolymer being crosslinked in said region within said shell, said copolymer being selected from among amphiphilic copolymers physically conducive to forming micelles prior to crosslinking, said particle having a mean particle diameter ranging from about 2 nm to about 1000 nm.

57. The particle of claim 56 wherein said particle has an aspect ratio ranging from about 0.5 to about 5000.

58. The particle of claim 56 wherein said particle has an aspect ratio ranging from about 1 to about 500.

59. The particle of claim 56 wherein said particle has a mean particle diameter ranging from about 5 to about 200.

60. The particle of claim 59 wherein said particle has an aspect ratio ranging from about 0.5 to about 5000.

61. The particle of claim 59 wherein said particle has an aspect ratio ranging from about 1 to about 500.

62. The particle of claim 56 wherein said crosslinked shell is hydrophilic and said core is hydrophobic.

63. The particle of claim 62 wherein said hydrophobic core is also crosslinked.

64. The particle of claim 56 wherein said crosslinked shell is hydrophobic and said core is hydrophilic.

65. The particle of claim 64 wherein said hydrophilic core is also crosslinked.

66. The particle of claim 56 wherein said amphiphilic copolymer is selected from the group consisting of amphiphilic diblock copolymers, amphiphilic triblock copolymers, amphiphilic multiblock copolymers, and amphiphilic graft copolymers.

67. The particle of claim 56 wherein said copolymer region comprised by said shell has a degree of crosslinking ranging from about 1% to about 80%.

68. The particle of claim 56 wherein said crosslinked shell comprises an amphiphilic copolymer region selected from the group consisting of polyvinylpyridine-N-chloromethylstyrene, polyvinylpyridine-N-chloromethylstyrene-co-polyvinylpyridine-N-bromopolyethylene oxide monomethyl ether, and polyacrylic acid.

69. The particle of claim 68 wherein said crosslinked shell comprises polyacrylic acid crosslinked with 2,2'-(ethylenedioxy)bis(ethylamine) or α,ω-(polyethyleneoxy)bis(ethylamine).

70. The particle of claim 68 wherein said core comprises an amphiphilic copolymer region selected from the group consisting of polystyrene, polyisoprene, poly(1,4-isoprene), and poly(6-hydroxycaproic acid).

71. The particle of claim 70 wherein said core comprises polyisoprene.

72. A particle comprising an amphiphilic block copolymer and having a core and a crosslinked shell which differs from said core in hydrophilicity and hydrophobicity, said shell comprising a block of said copolymer which differs in hydrophilicity and hydrophobicity from another block of said copolymer in said core, said copolymer being crosslinked in the block in said shell, said copolymer being selected from among amphiphilic block copolymers physically conducive to forming micelles prior to crosslinking.

73. The particle of claim 72 wherein said particle has mean particle diameter ranging from about 2 nm to about 1000 nm.

74. The particle of claim 73 wherein said particle has an aspect ratio ranging from about 0.5 to about 5000.

75. The particle of claim 72 wherein said crosslinked shell is hydrophilic and said core is hydrophobic.

76. The particle of claim 75 wherein said hydrophobic core is also crosslinked.

77. The particle of claim 72 wherein said crosslinked shell is hydrophobic and said core is hydrophilic.

78. The particle of claim 77 wherein said hydrophilic core is also crosslinked.

79. The particle of claim 72 wherein said amphiphilic block copolymer is selected from the group consisting of amphiphilic diblock copolymers, amphiphilic triblock copolymers, and amphiphilic multiblock copolymers.

80. The particle of claim 72 wherein said copolymer region comprised by said shell has a degree of crosslinking ranging from about 1% to about 80%.

81. The particle of claim 72 wherein said crosslinked shell comprises an amphiphilic copolymer region selected from the group consisting of polyvinylpyridine-N-chloromethylstyrene, polyvinylpyridine-N-chloromethylstyrene-co-polyvinylpyridine-N-bromopolyethylene oxide monomethyl ether, and polyacrylic acid.

82. The particle of claim 81 wherein said crosslinked shell comprises polyacrylic acid crosslinked with 2,2'-(ethylenedioxy)bis(ethylamine) or α,ω-(polyethyleneoxy)bis(ethylamine).

83. The particle of claim 72 wherein said core comprises an amphiphilic copolymer region selected from the group consisting of polystyrene, polyisoprene, poly(1,4-isoprene), and poly(6-hydroxycaproic acid).

84. The particle of claim 83 wherein said core comprises polyisoprene.

85. A particle comprising an amphiphilic copolymer and having a core and a crosslinked shell which differs from said core in hydrophilicity and hydrophobicity, said shell comprising a region of said copolymer which differs in hydrophilicity and hydrophobicity from another region of said copolymer in said core, said copolymer being crosslinked in the region in said shell, said particle being derived from a micellar assembly of said amphiphilic copolymer.

86. The particle of claim 85 wherein said particle is derived from a shell crosslinked micellar assembly.

87. The particle of claim 85 wherein said particle has mean particle diameter ranging from about 2 nm to about 1000 nm.

88. The particle of claim 87 wherein said particle has an aspect ratio ranging from about 0.5 to about 5000.

89. The particle of claim 85 wherein said crosslinked shell is hydrophilic and said core is hydrophobic.

90. The particle of claim 89 wherein said hydrophobic core is also crosslinked.

91. The particle of claim 85 wherein said crosslinked shell is hydrophobic and said core is hydrophilic.

92. The particle of claim 91 wherein said hydrophilic core is also crosslinked.

93. The particle of claim 85 wherein said amphiphilic copolymer is selected from the group consisting of amphiphilic diblock copolymers, amphiphilic triblock copolymers, amphiphilic multiblock copolymers, and graft copolymers.

94. The particle of claim 85 wherein said copolymer region comprised by said shell has a degree of crosslinking ranging from about 1% to about 80%.

95. The particle of claim 85 wherein said crosslinked shell comprises an amphiphilic copolymer region selected from the group consisting of polyvinylpyridine-N-chloromethylstyrene, polyvinylpyridine-N-chloromethylstyrene-co-polyvinylpyridine-N-bromopolyethylene oxide monomethyl ether, and polyacrylic acid.

96. The particle of claim 95 wherein said crosslinked shell comprises polyacrylic acid crosslinked with 2,2'-(ethylenedioxy)bis(ethylamine) or α,ω-(polyethyleneoxy)bis(ethylamine).

97. The particle of claim 85 wherein said core comprises an amphiphilic copolymer region selected from the group consisting of polystyrene, polyisoprene, poly(1,4-isoprene), and poly(6-hydroxycaproic acid).

98. The particle of claim 97 wherein said core comprises polyisoprene.

* * * * *

UNITED STATES PATENT AND TRADEMARK OFFICE
CERTIFICATE OF CORRECTION

PATENT NO.   : 6,383,500 B1   Page 1 of 1
DATED        : May 7, 2002
INVENTOR(S)  : Karen L. Wooley, K. Bruce Thurmond, II and Haiyong Huang It is certified that error appears in the above-identified patent and that said Letters Patent is hereby corrected as shown below:

Column 17,
Lines 60-65, delete the unlabeled chemical structure on the left.

Column 91,
Line 18, "claim 68" should read -- claim 56 --.

Signed and Sealed this

Twenty-third Day of December, 2003

JAMES E. ROGAN
*Director of the United States Patent and Trademark Office*